(12) United States Patent
Szallasi et al.

(10) Patent No.: US 10,308,986 B2
(45) Date of Patent: Jun. 4, 2019

(54) CANCER DIAGNOSIS, TREATMENT SELECTION AND TREATMENT

(71) Applicants: CHILDREN'S MEDICAL CENTER CORPORATION, Boston, MA (US); THE BRIGHAM AND WOMEN'S HOSPITAL, INC., Boston, MA (US); DANA-FARBER CANCER INSTITUTE, INC., Boston, MA (US); THE TECHNICAL UNIVERSITY OF DENMARK, Lyngby (DK)

(72) Inventors: Zoltan I. Szallasi, Boston, MA (US); Andrea L. Richardson, Chestnut Hill, MA (US); Nicolai J. Birkbak, København Ø (DK); Zhigang Wang, Newton, MA (US)

(73) Assignees: CHILDREN'S MEDICAL CENTER CORPORATION, Boston, MA (US); THE BRIGHAM AND WOMEN'S HOSPITAL, INC., Boston, MA (US); DANA-FARBER CANCER INSTITUTE, INC., Boston, MA (US); THE TECHNICAL UNIVERSITY OF DENMARK, KGS, Lyngby (DK)

( * ) Notice: Subject to any disclaimer, the term of this patent is extended or adjusted under 35 U.S.C. 154(b) by 239 days.

(21) Appl. No.: 14/774,772

(22) PCT Filed: Mar. 13, 2014

(86) PCT No.: PCT/US2014/025774
§ 371 (c)(1),
(2) Date: Sep. 11, 2015

(87) PCT Pub. No.: WO2014/160080
PCT Pub. Date: Oct. 2, 2014

(65) Prior Publication Data
US 2016/0122827 A1    May 5, 2016

Related U.S. Application Data

(60) Provisional application No. 61/784,234, filed on Mar. 14, 2013.

(51) Int. Cl.
| | |
|---|---|
| *A61K 31/282* | (2006.01) |
| *A61K 33/24* | (2006.01) |
| *C12Q 1/6886* | (2018.01) |
| *G01N 33/574* | (2006.01) |
| *A61K 31/704* | (2006.01) |

(52) U.S. Cl.
CPC .......... *C12Q 1/6886* (2013.01); *A61K 31/704* (2013.01); *A61K 33/24* (2013.01); *G01N 33/57415* (2013.01); *C12Q 2600/106* (2013.01); *C12Q 2600/156* (2013.01); *C12Q 2600/158* (2013.01)

(58) Field of Classification Search
CPC ............................. A61K 31/282; A61K 33/24
See application file for complete search history.

(56) References Cited

U.S. PATENT DOCUMENTS

| | | |
|---|---|---|
| 3,590,028 A | 6/1971 | Arcamone |
| 3,892,790 A | 7/1975 | Tobe |
| 3,904,663 A | 9/1975 | Tobe |
| 4,138,480 A | 2/1979 | Gosalvez |
| 4,946,954 A | 8/1990 | Talebian |
| 4,950,738 A | 8/1990 | King |
| 4,996,337 A | 2/1991 | Bitha |
| 5,091,521 A | 2/1992 | Kolar |
| 5,177,075 A | 1/1993 | Suto |
| 5,295,944 A | 3/1994 | Teicher |
| 5,434,256 A | 7/1995 | Khokhar |
| 5,445,934 A | 8/1995 | Fodor |
| 5,510,270 A | 4/1996 | Fodor |
| 5,527,905 A | 6/1996 | Sugimura |
| 5,539,083 A | 7/1996 | Cook |
| 5,556,752 A | 9/1996 | Lockhart |
| 5,578,832 A | 11/1996 | Trulson |
| 5,633,016 A | 5/1997 | Johnson |
| 5,633,243 A | 5/1997 | Sugimura |
| 5,744,305 A | 4/1998 | Fodor |
| RE36,397 E | 11/1999 | Zhang |
| 6,040,138 A | 3/2000 | Lockhart |

(Continued)

FOREIGN PATENT DOCUMENTS

| | | |
|---|---|---|
| EP | 0430402 A2 | 6/1991 |
| KR | 100925337 B1 | 10/2009 |

(Continued)

OTHER PUBLICATIONS

Abkevich et al., "Patterns of genomic loss of heterozygosity predict homologous recombination repair defects in epithelial ovarian cancer", Br J Cancer 107(10) 1776-1782 (2012).

(Continued)

*Primary Examiner* — Rachael E Bredefeld
*Assistant Examiner* — Chris E Simmons
(74) *Attorney, Agent, or Firm* — Nixon Peabody LLP; David S. Resnick; Mark J. FitzGerald

(57) ABSTRACT

The present invention provides assays, methods and systems for selecting an effective therapy for a subset of cancer patients having cancer cells with increased expression of BML and FANCI genes and/or having copy number increase in chromosome location 15q26 in the cancer cells and for treatment of such patients with the effective therapy of cancer patients based on the personalized cancer cell expression profile.

4 Claims, 26 Drawing Sheets
Specification includes a Sequence Listing.

(56) References Cited

U.S. PATENT DOCUMENTS

| | | | |
|---|---|---|---|
| 6,087,340 | A | 7/2000 | Gatti |
| 6,210,891 | B1 | 4/2001 | Nyren |
| 6,214,821 | B1 | 4/2001 | Daoud |
| 6,258,568 | B1 | 7/2001 | Nyren |
| 6,274,320 | B1 | 8/2001 | Rothberg |
| 6,403,563 | B1 | 6/2002 | Geroni |
| 6,455,258 | B2 | 9/2002 | Bastian |
| 6,465,177 | B1 | 10/2002 | Hoon |
| 6,534,293 | B1 | 3/2003 | Barany |
| 7,351,701 | B2 | 4/2008 | Helleday |
| 7,485,707 | B2 | 2/2009 | Matvienko |
| 7,732,491 | B2 | 6/2010 | Sherman |
| 7,754,684 | B2 | 7/2010 | Stewart |
| 7,759,488 | B2 | 7/2010 | Xiao |
| 7,759,510 | B2 | 7/2010 | Kay |
| 7,858,331 | B2 | 12/2010 | D'Andrea et al. |
| 7,868,040 | B2 | 1/2011 | Wilson |
| 7,915,280 | B2 | 3/2011 | Ferraris |
| 9,279,156 | B2 | 3/2016 | Gutin |
| 2003/0049613 | A1 | 3/2003 | Perucho |
| 2005/0112604 | A1 | 5/2005 | Fujimoto |
| 2006/0088870 | A1 | 4/2006 | Finkelstein |
| 2007/0004621 | A1 | 1/2007 | Shridhar |
| 2007/0070349 | A1 | 3/2007 | Harris |
| 2008/0108057 | A1 | 5/2008 | Griffith |
| 2009/0081237 | A1 | 3/2009 | D'Andrea et al. |
| 2009/0246789 | A1 | 10/2009 | Buckhaults |
| 2010/0145894 | A1 | 6/2010 | Semizarov |
| 2010/0159466 | A1 | 6/2010 | Eng |
| 2012/0015050 | A1 | 1/2012 | Abkevich |
| 2013/0281312 | A1 | 10/2013 | Richardson |
| 2015/0080260 | A1 | 3/2015 | Abkevich |

FOREIGN PATENT DOCUMENTS

| | | |
|---|---|---|
| WO | 1995/020952 A1 | 8/1995 |
| WO | 1998/041531 A2 | 9/1998 |
| WO | 1999/054498 A1 | 10/1999 |
| WO | 2000/024933 A1 | 5/2000 |
| WO | 2003/074723 A2 | 9/2003 |
| WO | 2004/042032 A2 | 5/2004 |
| WO | 2006/098978 A1 | 9/2006 |
| WO | 2006/110855 A2 | 10/2006 |
| WO | 2006/116341 A1 | 11/2006 |
| WO | 2006/128195 A2 | 11/2006 |
| WO | 2007/035893 A2 | 3/2007 |
| WO | 2009/033178 A1 | 3/2009 |
| WO | 2009/073869 A1 | 6/2009 |
| WO | 2009/148528 A2 | 12/2009 |
| WO | 2010/051318 A2 | 5/2010 |
| WO | 2011/048495 A1 | 4/2011 |
| WO | 2011/106541 A2 | 9/2011 |
| WO | 2011/160063 A2 | 12/2011 |
| WO | 2012-019000 | 2/2012 |
| WO | 2012/027224 A1 | 3/2012 |
| WO | 2013/130347 A1 | 9/2013 |
| WO | 2013/182645 A1 | 12/2013 |

OTHER PUBLICATIONS

Abkevich et al., "Supplemental Material: Table S1: Validation of copy number determinations by Real Time PCR SNP ID Adjacent Gene Sample Copy Number By CCNT SNP A", Cancer Research (2006). (14 pages).

Al-Mulla et al., "Metastatic recurrence of early-stage colorectal cancer is linked to loss of heterozygosity on chromosomes 4 and 14q" J Clin Pathol 59(6) 624-630 (2006).

Anonymous, "Myriads HRD Test Significantly Predicts Response to Cisplatin Treatment in Patients With Triple Negative Breast Cancer in Second Research Study", Myriad, Dec. 2013.

Argos et al., "Genomewide scan for loss of heterozygosity and chromosomal amplification in breast carcinoma using single-nucleotide polymorphism arrays", Cancer Genet Cytogenet 182(2) 69-74 (2008).

Arlt et al., "BRCA1 is required for common-fragile-site stability via its G2/M checkpoint function", Mol Cell Biol 24(15)6701-6709 (2004).

Ashworth et al., "A synthetic lethal therapeutic approach: poly(ADP) ribose polymerase inhibitors for the treatment of cancers deficient in DNA double-strand break repair", J Clin Oncol 26(22) 3785-3790 (2008).

Bamford et al., "The COSMIC (Catalogue of Somatic Mutations in Cancer) database and website", Br J Cancer 91 (2) 355-358 (2004).

Beder et al., "Genome-wide analyses on loss of heterozygosity in head and neck squamous cell carcinomas", Lab Invest 83(1) 99-105 (2003).

The Cancer Genome Atlas Research Network, "Integrated genomic analyses of ovarian carcinoma", Nature 474(7353) 609-615 (2011).

Bengtsson et al., "A single-array preprocessing method for estimating full-resolution raw copy numbers from all Affymetrix genotyping arrays including GenomeWideSNP 5 & 6", Bioinformatics 25(17) 2149-2156 (2009).

Bengtsson et al., "TumorBoost: normalization of allele-specific tumor copy numbers from a single pair of tumor-normal genotyping microarrays", BMC Bioinformatic 11; 245 (2010).

Beroukhim et al., "Inferring loss-of-heterozygosity from unpaired tumors using high-density oligonucleotide SNP arrays", PLoS Comput Biol 2(5) e41 (2006).

Birkbak et al., "Abstract 4823: Copy number gain and increased expression of BLM and FANCI is associated with sensitivity to genotoxic chemotherapy in triple negative breast and serous ovarian cancer", Cancer Research 72(8) Abstract (2012).

Birkbak et al., "Telomeric allelic imbalance indicates defective DNA repair and sensitivity to DNA-damaging agents", Cancer Discov 2(4) 366-375 (2010).

Bouwman et al., "53BP1 loss rescues BRCA1 deficiency and is associated with triple-negative and BRCA-mutated breast cancers", Nat Struct Mol Biol 17(6) 688-695 (2010).

Bryant et al., "Specific killing of BRCA2-deficient tumours with inhibitors of poly(ADP-ribose) polymerase", Nature 434(7035) 913-917 (2005).

Buch et al., "Prediction of recurrence of nonfunctioning pituitary tumours by loss of heterozygosity analysis", Clin Endocrinol (oxf) 61(1) 19-25 (2004).

Bunting et al., "53BP1 inhibits homologous recombination in Brca1-deficient cells by blocking resection of DNA breaks", Cell 141(2) 243-254 (2010).

Burger et al., "Drug transporters of platinum-based anticancer agents and their clinical significance", Drug Resist Updat 14(1) 22-34 (2011).

Byrski et al., "Response to neoadjuvant therapy with cisplatin in BRCA1-positive breast cancer patients", Breast Cancer Res Treat 115(2) 359-363 (2009).

Calvert et al. "245: PARP inhibitors in cancer treatment", European Journal of Cancer Supplements 6(12) 80 (2008).

Canadian Office Action from Application No. 2,802,882, dated Feb. 24, 2017.

Carr et al., "High-resolution analysis of allelic imbalance in neuroblastoma cell lines by single nucleotide polymorphism arrays", Cancer Genet Cytogenet 172(2) 127-138 (2007).

Cass et al., "Improved survival in women with BRCA-associated ovarian carcinoma", Cancer 97(9) 2187-2195 (2003).

Cerbinskaite et al., "Defective homologous recombination in human cancers", Cancer Treat Rev 38(2) 89-100 (2012).

Cha et al., "ATR homolog Mec1 promotes fork progression, thus averting breaks in replication slow zones", Science 297(5581) 602-606 (2002).

Chang et al., "Assessment of plasma DNA levels, allelic imbalance, and CA 125 as diagnostic tests for cancer", J Natl Cancer Inst 94(22) 1697-1703 (2002).

Cheung et al., "Clinicopathologic significance of loss of heterozygosity on chromosome 1 in cervical cancer", Gynecol Oncol 96(2) 510-515 (2005).

(56) References Cited

OTHER PUBLICATIONS

Dann et al., "BRCA1/2 mutations and expression: response to platinum chemotherapy in patients with advanced stage epithelial ovarian cancer", Gynecol Oncol 125(3) 677-682 (2012).
De Preter et al., "Application of laser capture microdissection in genetic analysis of neuroblastoma and neuroblastoma precursor cells", Cancer Lett 197(1-2) 53-61 (2003).
De Soto et al., "The inhibition and treatment of breast cancer with poly (ADP-ribose) polymerase (PARP-1) Inhibitors", Int J Biol Sci 2(4) 179-185 (2006).
Edwards et al., "Resistance to therapy caused by intragenic deletion in BRCA2", Nature 451(7182) 1111-1115 (2008).
Etemadmoghadam et al., "Integrated genome-wide DNA copy number and expression analysis identifies distinct mechanisms of primary chemoresistance in ovarian carcinomas", Clin Cancer Res 15(4) 1417-1427 (2009).
European Communication from Application No. 12801070.9, dated Dec. 22, 2016.
European Communication Response for Application No. 11757992.0, dated Mar. 21, 2014.
European Communication Response for Application 11757992.0, dated Dec. 9, 2014.
European Communication Response for Application 11796544.2, dated Sep. 28, 2015.
European Communication Response for Application No. 15189527.3, dated Sep. 30, 2016.
European Communication Response for Application No. 11796544.2, dated Feb. 1, 2016.
European Communication Response for Application No. 11796544.2, dated Aug. 3, 2015.
European Communication Response for Application No. 12860530.0, dated Feb. 10, 2016.
European Communication Response for Application No. 12860530.0, dated Mar. 17, 2017.
European Communication for Application No. 11757992.0, dated Aug. 5, 2014.
European Communication for Application No. 11757992.0, dated Dec. 10, 2013.
European Communication for Application No. 11796544.2, dated Jan. 20, 2016.
European Communication for Application No. 11796544.2, dated May 11, 2015.
European Communication for Application No. 11796544.2, dated Sep. 11, 2015.
European Communication for Application No. 12801070.9, dated Apr. 1, 2016.
European Intention to Grant for Application 11757992.0, dated Jul. 28, 2015.
Sang-Wook et al., "Genetic classification of colorectal cancer based on chromosomal loss and microsatellite instability predicts survival", Clin Cancer Res 9(7) 2311-2322 (2002).
Santana-Davila et al., "Treatment options for patients with triple-negative breast cancer", J Hematol Oncol 3;42 (2010).
Schouten et al., "Challenges in the Use of DNA Repair Deficiency As a Biomarker in Breast Cancer", J Clin Oncol 33(17) 1867-1869 (2015).
Schwartz et al., "Homologous recombination and nonhomologous end-joining repair pathways regulate fragile site stability", Genes Dev 19(22) 2715-2726 (2005).
Sebat et al., "Large-scale copy number polymorphism in the human genome", Science 305(5683) 525-528 (2004).
Silva et al., "Loss of heterozygosity in BRCA1 and BRCA2 markers and high-grade malignancy in breast cancer", Breast Cancer Res Treat 53(1) 9-17 (1999).
Silver et al., "Further evidence for BRCA1 communication with the inactive X chromosome", Cell 128(5) 991-1002 (2007).
Smid et al., "Patterns and incidence of chromosomal instability and their prognostic relevance in breast cancer subtypes", Breast Cancer Res Treat 128(1) 23-30 (2011).
Sorlie et al., "Repeated observation of breast tumor subtypes in independent gene expression data sets", Proc Natl Acord Sci USA 100(14) 8418-8423 (2003).
Soule et al., "Isolation and characterization of a spontaneously immortalized human breast epithelial cell line, MCF-10", Cancer Res 50(18) 6075-6086 (1990).
Stankiewicz et al., "Genome architecture catalyzes nonrecurrent chromosomal rearrangements", Am J Hum Genet 72(5) 1101-1116 (2003).
Stefansson et al., "Genomic profiling of breast tumours in relation to BRCA abnormalities and phenotypes", Breast Cancer Res 11(4) R47 (2009).
Swisher et al., "Secondary BRCA1 mutations in BRCA1-mutated ovarian carcinomas with platinum resistance", Cancer Res 68(8) 2581-2586 (2008).
Tai et al., "High-throughput loss-of-heterozygosity study of chromosome 3p in lung cancer using single-nucleotide polymorphism markers", Canccer REs 66(8) 4133-4138 (2006).
Takahashi et al., "Clonal and parallel evolution of primary lung cancers and their metastases revealed by molecular dissection of cancer cells", Clin Cancer Res 13(1) 111-120 (2007).
Tan et al., ""BRCAness" syndrome in ovarian cancer: a case-control study describing the clinical features and outcome of patients with epithelial ovarian cancer associated with BRCA1 and BRCA2 mutations", J Clin Oncol 26(34) 5530-5536 (2008).
Tassone et al., "BRCA1 expression modulates chemosensitivity of BRCA1-defective HCC1937 human breast cancer cells", Br J Cancer 88(8) 1285-1291 (2003).
Teh et al., "Genomewide single nucleotide polymorphism microarray mapping in basal cell carcinomas unveils uniparental disomy as a key somatic event", Cancer Res 65(19) 8597-8603 (2005).
Telli et al., "Abstract PD09-04: Homologous Recombination Deficiency (HRD) score predicts pathological response following neoadjuvant platinum-based therapy in triple-negative and BRCA1/2 mutation-associated breast cancer (BBC)", Cancer Research 72(24) (2012).
Telli et al., "Phase II Study of Gemcitabine, Carboplatin, and Iniparib As Neoadjuvant Therapy for Triple-Negative and BRCA1/2 Mutation-Associated Breast Cancer With Assessment of a Tumor-Based Measure of Genomic Instability: PrECOG 0105", J Clin Oncol 33(17) 1895-1901 (2015).
Tseng et al., "Genomewide loss of heterozygosity and its clinical associations in non small cell lung cancer", Int J Cancer 117(2) 241-247 (2005).
Tuna et al., "Association between acquired uniparental disomy and homozygous mutations and HER2/ER/PR status in breast cancer", PLoS One 5(11) e15094 (2010).
Turner et al., "BRCA1 dysfunction in sporadic basal-like breast cancer", Oncogene 26(14) 2126-2132 (2007).
Valeri et al., "High frequency of allelic losses in high-grade prostate cancer is associated with biochemical progression after radical prostatectomy", Urol Oncol 23(2) 87-92 (2005).
Van Loo et al., "Allele-specific copy number analysis of tumors", Proc Natl Acad Sci USA 107(39) 16910-16915 (2010).
Valchenboum et al., "Comparison of primary neuroblastoma tumors and derivative early-passage cell lines using genome-wide single nucleotide polymorphism array analysis", Cancer Res 69(10) 4143-4149 (2009).
Vollebergh et al., "Genomic instability in breast and ovarian cancers: translation into clinical predictive biomarkers", Cell Mol Life Sci 69(2) 223-245 (2012).
Vrieling et al., "Mitotic maneuvers in the light", Nat Genet 28(2) 101-102 (2001).
Walsh et al., "Genome-wide loss of heterozygosity and uniparental disomy in BRCA1/2-associated ovarian carcinomas", Clin Cancer Res 14(23) 7645-7651 (2008).
Wang et al., "Loss of heterozygosity and its correlation with expression profiles in subclasses of invasive breast cancers", Cancer Res 64(1) 64-71 (2004).
Wang et al., "Analysis of molecular inversion probe performance for allele copy number determination", Genome Biol 8(11) R246 (2007).

(56) References Cited

OTHER PUBLICATIONS

Wilcox et al., "High-resolution methylation analysis of the BRCA1 promoter in ovarian tumors", Cancer Genet Cytogenet 159(2) 114-122 (2005).
Wilcoxen et al., "Homologous recombination deficiency (HRD) score enriches for niraparib sensitive high grade ovarian tumors", J Clinc Oncol, Supplemental Abstract 5532 (2015).
Xiao et al., "The XIST noncoding RNA functions independently of BRCA1 in X inactivation", Cell 128(5) 977-989 (2007).
Xu et al., "Centrosome amplification and a defective G2-M cell cycle checkpoint induce genetic instability in BRCA1 exon 11 isoform-deficient cells", Mol Cell 3(3) 389-395 (1999).
Yang et al., "Reconstitution of caspase 3 sensitizes MCF-7 breast cancer cells to doxorubicin- and etoposide-induced apoptosis", Cancer Res 61(1) 348-354 (2001).
Yaris et al., "Primary cerebral neuroblastoma: a case treated with adjuvant chemotherapy and radiotherapy", Turk J Pediatr 46(2) 182-185 (2004).
Zhao et al., "Systematic detection of putative tumor suppressor genes through the combined use of exome and transcriptome sequencing", Genome Biology 11(11) R114 (2010).
Wilcoxen et al., "Use of Homologous recombination deficiency (HRD) score enriches for niraparib sensitive high grade ovarian tumors" J Clin Oncol Supplemental Abstract 5532 (2015).
Kalb et al., "Fanconi anemia: causes and consequences of genetic instability", Genome Dyn 1; 218-242 (2006).
Kerangueven et al., "Genome-wide search for loss of heterozygosity shows extensive genetic diversity of human breast carcinomas", Cancer Res 57(24) 5469-5474 (1997).
Ko et al., "Frequent loss of heterozygosity on multiple chromosomes in Chinese esophageal squamous cell carcinomas", Cancer Lee 170(2) 131-138 (2001).
Kolmietz et al., "The role of Alu repeat clusters as mediators of recurrent chromosomal aberrations in tumors", Genes Chromosomes Cancer 35(2) 97-112 (2002).
Kujawski et al., "Genomic complexity identifies patients with aggressive chronic lymphocytic leukemia", Blood 112(5) 1993-2003 (2008).
Lakhani et al., "Prediction of BRCA1 status in patients with breast cancer using estrogen receptor and basal phenotype", Clin Cancer Res 11(14) 5175-5180 (2005).
Lemeta et al., "Loss of heterozygosity at 6q is frequent and concurrent with 3p loss in sporadic and familial capillary hemangioblastomas", J Neuropathol Exp Neurol 63(10) 1072-1079 (2004).
Leunen et al., "Recurrent copy number alterations in BRCA1-mutated ovarian tumors alter biological pathways", Hum Mutat 30(12) 1693-1702 (2009).
Li et al., "Amplification of LAPTM4B and YWHAZ contributes to chemotherapy resistance and recurrence of breast cancer", Nat Med 16(2) 214-218 (2010).
Li et al., "Jetset: selecting the optimal microarray probe set to represent a gene", BMC Bioinformatics 12;474 (2011) (7 pages).
Li et al., "Major copy proportion analysis of tumor samples using SNP arrays", BMC Bioinformatice 9;204 (2008) (16 pages).
Lin et al., "Integrated analysis of copy number alterations and loss of heterozygosity in human pancreatic cancer using a high-resolution, single nucleotide polymorphism array", Oncology 75(1-2) 102-112 (2008).
Loveday et al., "Germline mutations in RAD51D confer susceptibility to ovarian cancer", Nat Genet 43(9) 879-882 (2011).
Luo et al., "Cancer predisposition caused by elevated mitotic recombination in Bloom mice", Nat Genet 26(4) 424-429 (2000).
Maeck et al., "Genetic instability in myelodysplastic syndrome: detection of microsatellite instability and loss of heterozygosity in bone marrow samples with karyotype alterations", Br J Haematol 109(4) 842-846 (2000).
Marsit et al., "Inactivation of the Fanconi anemia/BRCA pathway in lung and oral cancers: implications for treatment and survival", Oncogene 23(4) 1000-1004 (2004).

Mateo et al., "Appraising iniparib, the PARP inhibitor that never was—what must we learn?", Nat Rev Clin Oncol 10 (12) 688-696 (2013).
Matsumoto et al. "Allelic imbalance at 1p36 may predict prognosis of chemoradiation therapy for bladder preservation in patients with invasive bladder cancer." British Journal of Cancer 91(6)1025-1031 (2004).
McVean et al., "What drives recombination hotspots to repeat DNA in humans?", Philos Trans R Soc Lond B Biol Sci 365(1544) 1213-1218 (2010).
Meadows et al., "Genome-wide analysis of loss of heterozygosity and copy number amplification in uterine leiomyomas using the 100K single nucleotide polymorphism array", Exp Mol Pathol 91(1) 434-439 (2011).
Medri et al., "Prognostic relevance of mitotic activity in patients with node-negative breast cancer", Mod Pathol 16(11) 1067-1075 (2003).
Mei et al., "Genome-wide detection of allelic imbalance using human SNPs and high-density DNA arrays", Genome Res 10(8) 1126-1137 (2000).
Meindl et al., "Germline mutations in breast and ovarian cancer pedigrees establish RAD51C as a human cancer susceptibility gene", Nat Genet 42(5) 410-414 (2010).
Mendes-Periera et al., "Synthetic lethal targeting of PTEN mutant cells with PARP inhibitors", EMBO Mol Med 1 (6-7) 315-322 (2009).
Mukhopadhyay et al., "Clinicopathological features of homologous recombination-deficient epithelial ovarian cancers: sensitivity to PARP inhibitors, platinum, and survival", Cancer Res 72(22) 5675-5782 (2012).
Murayama-Hosokawa et al., "Genome-wide single-nucleotide polymorphism arrays in endometrial carcinomas associate extensive chromosomal instability with poor prognosis and unveil frequent chromosomal imbalances involved in the PI3-kinase pathway", Oncogene 29(13) 1897-1908 (2010).
Nannya et al., "A robust algorithm for copy number detection using high-density oligonucleotide single nucleotide polymorphism genotyping arrays", Cancer Res 65(14) 6071-6079 (2005).
Narayan et al., "Frequent Promoter Methylation of CDH1, DAPK, RARB, and HIC1 Genes in Carcinoma of Cervix Uteri: Its Relationship to Clinical Outcome", Mol Cancer 2; 24 (2003) (12 pages).
Norquist et al., "Secondary somatic mutations restoring BRCA1/2 predict chemotherapy resistance in hereditary ovarian carcinomas", J Clin Oncol 29(22) 3008-3015 (2011).
Novak et al. "A high-resolution allelotype of B-cell chronic lymphocytic leukemia (B-CLL).", Blood 100(5) 1781-1794 (2002).
Ogston et al., "A new histological grading system to assess response of breast cancers to primary chemotherapy: prognostic significance and survival", Breast 12(5) 320-327 (2003).
Osborne et al., "A genome-wide map showing common regions of loss of heterozygosity/allelic imbalance in breast cancer", Cancer Res 60(14) 3706-3712 (2000).
O'Shaughnessy et al., "Iniparib plus chemotherapy in metastatic triple-negative breast cancer", N Engl J Med 364 (3) 205-214 (2011).
Ott et al., "Chromosomal instability rather than p53 mutation is associated with response to neoadjuvant cisplatin-based chemotherapy in gastric carcinoma", Clinc Cancer Res 9(6) 2307-2315 (2003).
Patel et al., "Failure of iniparib to inhibit poly(ADP-Ribose) polymerase in vitro", Clin Cancer Res 18(6) 155-1662 (2012).
Patocs et al., "Breast-cancer stromal cells with TP53 mutations and nodal metastases", N Engld J Med 357(25) 2543-2551 (2007).
Peng et al., "Genome-wide transcriptome profiling of homologous recombination DNA repair", Nat Commun 5;3361 (2014) (11 pages).
Penning et al., "Discovery and SAR of 2-(1-propylpiperidin-4-yl)-1H-benzimidazole-4-carboxamide: a potent inhibitor of poly (ADP-ribose) polymerase (PARP) for the treatment of cancer", Bioorganic & Medicinal Chemistry 16(14) 6965-6975 (2008).
Pfeifer et al., "Genome-wide analysis of DNA copy number changes and LOH in CLL using high-density SNP arrays", Blood 109(3) 1202-1210 (2007).

(56) References Cited

OTHER PUBLICATIONS

Popova et al., "Genome Alteration Print (GAP): a tool to visualize and mine complex cancer genomic profiles obtained by SNP arrays", Genome Biol 10(11) R128 (2009) (14 pages).

Popova et al., "Ploidy and large-scale genomic instability consistently identify basal-like breast carcinomas with BRCA1/2 inactivation", Cancer Research 72(21) 5454-5462 (2012).

Puliti et al., "Low-copy repeats on chromosome 22q11.2 show replication timing switches, DNA flexibility peaks and stress inducible asynchrony, sharing instability features with fragile sites", Mutat Res 686(1-2) 74-83 (2010).

Rakha et al., "Basal-like breast cancer: a critical review", J Clin Oncol 26(15) 2568-2581 (2008).

Ramirez et al., "Loss of 1p, 19q, and 10q heterozygosity prospectively predicts prognosis of oligodendroglial tumors—towards individualized tumor treatment?", Neuro Oncol 12(5) 490-499 (2010).

Richard et al., "Comparative genomics and molecular dynamics of DNA repeats in eukaryotes", Microbiol Mol Biol Rev 72(4) 686-727 (2008).

Richardson et al., "X chromosomal abnormalities in basal-like human breast cancer", Cancer Cell 9(2) 121-132 (2006).

Ryan et al., 2009 ASCO Annual Meeting, http://meetinglibrary.asco.org/content/34135-65, (2009). "Neoadjuvant cisplatin and bevacizumab in triple negative breast cancer (TNBC): Safety and efficacy."

Sakai et al., "Functional restoration of BRCA2 protein by secondary BRCA2 mutations in BRCA2-mutated ovarian carcinoma", Cancer Res 69(16) 6381-6386 (2009).

Sakai et al., "Secondary mutations as a mechanism of cisplatin resistance in BRCA2-mutated cancers", Nature 451 (7182) 1116-1120 (2008).

Samouelian et al., "Chemosensitivity and radiosensitivity profiles of four new human epithelial ovarian cancer cell lines exhibiting genetic alterations in BRCA2, TGFbeta-RII, KRAS2, TP53 and/or CDNK2A", Cancer Chemother Pharmacol 54(6) 497-504 (2004).

Birkbak et al, "Abstract 4823: Copy number gain and increased expression of BLM and FANCI is associated with sensitivity to genotoxic chemotherapy in triple negative breast and serous ovarian cancer." Cancer Research, vol. 72, Issue 8, Supplement 1, p. 1, 2012, Abstract only.

Silver et al, "Efficacy of Neoadjuvant Cisplatin in triple-negative breast cancer", Journal of Clinical Oncology, vol. 27, No. 7, pp. 1145-1153, 2010.

European Intention to Grant for Application No. 11796544.2, dated Mar. 31, 2016.

European Patent Office Communication for Application No. 12860530.0, dated Nov. 28, 2016.

European Search Report from Application No. 12801070.9, dated Dec. 3, 2014.

European Search Report from Application No. 12860530.0, dated Jul. 24, 2015.

Extended European Search Report from Application No. 14779403.6, dated Oct. 28, 2016.

Extended European Search Report for Application No. 16166825.6, dated Nov. 11, 2016.

Extended European Search Report for Application No. 11796544.2, dated Nov. 18, 2013.

Extended European Search Report for Application No. 151895273, dated Mar. 31, 2016.

Extended European Search Report for Application No. 11748075.6, dated Jul. 29, 2013.

Fang et al., "Genomic differences between estrogen receptor (ER)-positive and ER-negative human breast carcinoma identified by single nucleotide polymorphism array comparative genome hybridization analysis", Cancer 117(10) 2024-2034 (2011).

Farmer et al., "Targeting the DNA repair defect in BRCA mutant cells as a therapeutic strategy", Nature 434(7035) 317-921 (2005).

Feltmate et al., "Whole-genome allelotyping identified distinct loss-of-heterozygosity patterns in mucinous ovarian and appendiceal carcinomas", Clin Cancer Res 11(21) 7651-7657 (2005).

Ferreira et al., "Array CGH and gene-expression profiling reveals distinct genomic instability patterns associated with DNA repair and cell-cycle checkpoint pathways in Ewing's sarcoma", Oncogene 27(14) 2084-2090 (2008).

Filopanti et al., "Loss of heterozygosity at the SS receptor type 5 locus in human GH- and TSH-secreting pituitary adenomas", J Endocrinol Invest 27(10) 937-942 (2004).

Fontanillas et al., "Key considerations for measuring allelic expression on a genomic scale using high-throughput sequencing", Mol Ecol 19(Suppl 1) 212-227 (2010).

Franko et al., "Loss of heterozygosity predicts poor survival after resection of pancreatic adenocarcinoma", J Gastrointest Surg 12(10) 1664-1672 (2008).

Friedenson, "BRCA1 and BRCA2 pathways and the risk of cancers other than breast or ovarian", MedGenMed 7(2) 60 (2005). (25 pages).

Gelmon et al., "Olaparib in patients with recurrent high-grade serous or poorly differentiated ovarian carcinoma or triple-negative breast cancer: a phase 2, multicentre, open-label, non-randomised study", Lancet Oncol 12(9) 852-861 (2011).

Goransson et al., "Quantification of normal cell fraction and copy number neutral LOH in clinical lung cancer samples using SNP array data", PLoS One 4(6) e6057 (2009).

Gorringe et al., "Are there any more ovarian tumor suppressor genes? A new perspective using ultra high-resolution copy number and loss of heterozygosity analysis", Genes Chromosomes Cancer 48(10) 931-942 (2009).

Graziani et al., "PARP-1 inhibition to treat cancer, ischemia, inflammation", Pharmacol Res 52(1) 1-4 (2005).

Gudmundsdottir et al., "The roles of BRCA1 and BRCA2 and associated proteins in the maintenance of genomic stability", Oncogene 25(43) 5864-5874 (2006).

Gunnarsson et al., "Large but not small copy-number alterations correlate to high-risk genomic aberrations and survival in chronic lymphocytic leukemia: a high-resolution genomic screening of newly diagnosed patients", Lukemia 24(1) 211-216 (2010).

Hampton et al., "Simultaneous assessment of loss of heterozygosity at multiple microsatellite loci using semi-automated fluorescence-based detection: subregional mapping of chromosome 4 in cervical carcinoma", Proc Natl cad Sci USA 93(13) 6704-6709 (1996).

Hastings et al., "A microhomology-mediated break-induced replication model for the origin of human copy number variation", PLoS Genet 5(1) e1000327 (2009).

Hastings et al., "Mechanisms of change in gene copy number", Nat Rev Genet 10(8) 551-564 (2009).

Heap et al., "Genome-wide analysis of allelic expression imbalance in human primary cells by high-throughput transcriptome resequencing", Hum Mol Genet 19(1) 122-134 (2010).

Heinsohn et al., "Determination of the prognostic value of loss of heterozygosity at the retinoblastoma gene in osteosarcoma", Int J Oncol 30(5) 1205-1214 (2007).

Heiser et al., "Subtype and pathway specific responses to anticancer compounds in breast cancer", Proc Natl Acad Sci USA 109(8) 2724-2729 (2012).

Hendricks et al., ""Recombomice": the past, present, and future of recombination-detection in mice", DNA Repair (Amst) 3(10) 1255-1261 (2004).

Hennessy et al., "Somatic mutations in BRCA1 and BRCA2 could expand the number of patients that benefit from poly (ADP ribose) polymerase inhibitors in ovarian cancer", J Clin Oncol 28(22) 3570-3576 (2010).

Holstege et al., "BRCA1-mutated and basal-like breast cancers have similar aCGH profiles and a high incidence of protein truncating TP53 mutations", BMC Cancer 10; 654 (2010).

Iafrate et al., "Detection of large-scale variation in the human genome", Nat Genet 36(9) 949-951 (2004).

International Preliminary Report on Patentability for Application No. PCT/US2012/071380. dated Jun. 24, 2014.

International Search Report for Application No. PCT/EP2013/061707, dated Jul. 29, 2013.

International Search Report for Application No. PCT/EP2014/076786, dated Feb. 27, 2015.

(56) References Cited

OTHER PUBLICATIONS

International Search Report for Application No. PCT/US2011/026098, dated Nov. 25, 2011.
International Search Report for Application No. PCT/US2011/040953, dated Feb. 27, 2012.
International Search Report for Application No. PCT/US2011/048427, dated Jul. 11, 2011.
International Search Report for Application No. PCT/US2012/042668, dated Feb. 1, 2013.
International Search Report for Application No. PCT/US2012/071380, dated Apr. 12, 2013.
International Search Report for Application No. PCT/US2013/027295, dated Jun. 10, 2013.
International Search Report for Application No. PCT/US2015/045561, dated Nov. 9, 2015.
Isakoff et al., "TBCRC009: A Multicenter Phase II Clinical Trial of Platinum Monotherapy With Biomarker Assessment in Metastatic Triple-Negative Breast Cancer", J Clin Oncol 33(17) 1902-1909 (2015).
Janne et al., "High-resolution single-nucleotide polymorphism array and clustering analysis of loss of heterozygosity in human lung cancer cell lines", Oncogene 23(15) 2716-2726 (2004).
Johansson et al., "Abstract 4833: A genomic portrait of tumor progression using next-generation sequencing", Cancer Research 71:4833 (2011).
Joosse et al., "Prediction of BRCA1-association in hereditary non-BRCA1/2 breast carcinomas with array-CGH", Breast Cancer Res Treat 116(3) 479-489 (2009).
Juul et al., "A Genomic-Profile Derived Summary Measure of Chromosomal Breakpoints Predicts Response to Treatment with the DNA-Damaging Agent Cisplatin", Cancer Research 69(24) 509S-510S (2009).
Juul et al., "33P: Amount of Allelic Imbalance Predicts Response to Cisplatin in Breast and Ovarian Cancer", Annals of Oncology 21(4) Abstract (2010).
Kaklamani et al., "Phase II neoadjuvant clinical trial of carboplatin and eribulin in women with triple negative early-stage breast cancer (NCT01372579)" Breast Cancer Res Treat 151(3) 629-638 (2015).

Correlation between copy number and mRNA expression, Genes on 15q26.1–2

| ABHD2 | MAN2A2 |
|---|---|
| AEN | MFGE8 |
| BLM | MRPL46 |
| C15orf42 | MRPS11 |
| CIB1 | NGRN |
| CRTC3 | POLG |
| DET1 | PRC1 |
| FAM174B | RCCD1 |
| FANCI | SEMA4B |
| HDDC3 | UNC45A |
| IDH2 | VPS33B |
| IQGAP1 | |

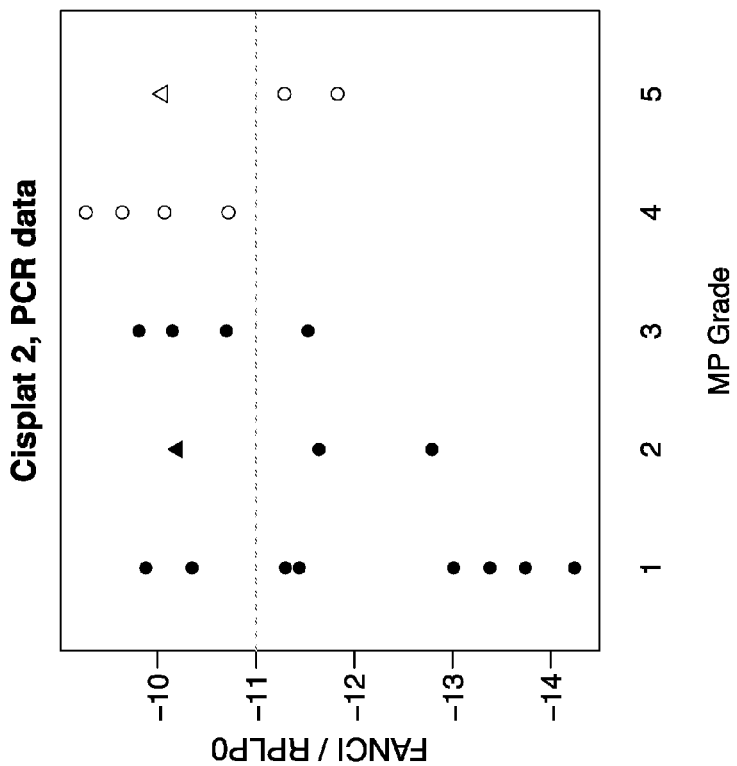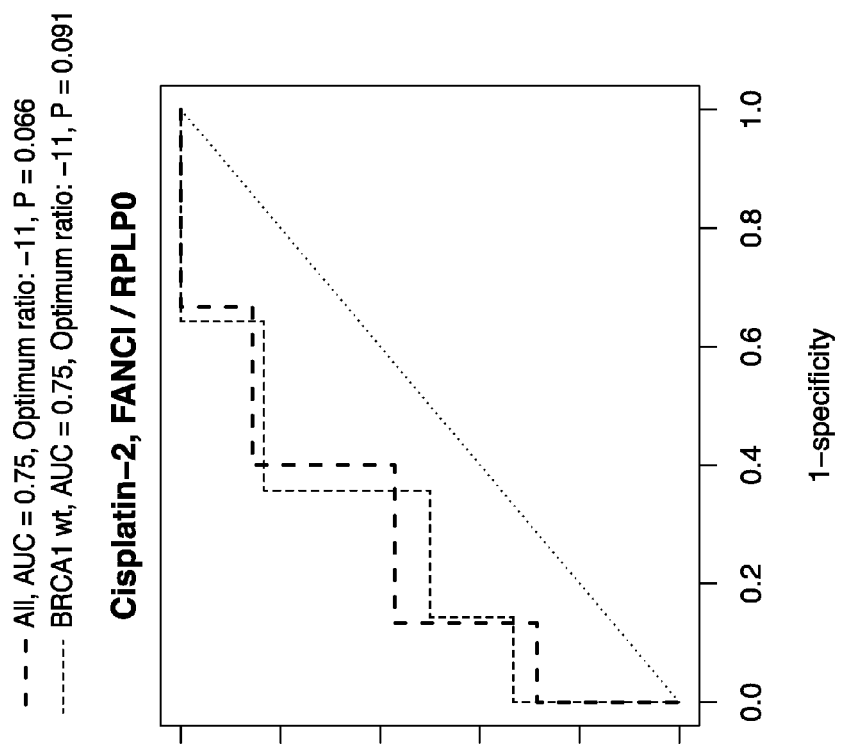
FIG. 19

SEQUENCE LISTING

```
<160> NUMBER OF SEQ ID NOS: 1

<210> SEQ ID NO 1
<211> LENGTH: 4
<212> TYPE: PRT
<213> ORGANISM: Homo sapiens

<400> SEQUENCE: 1

Lys Asp Glu Leu
1
```

CANCER DIAGNOSIS, TREATMENT SELECTION AND TREATMENT

CROSS-REFERENCE TO RELATED APPLICATIONS

This application is a 35 U.S.C. § 371 National Phase Entry Application of International Application No. PCT/US2014/025774 filed Mar. 13, 2014, which designates the U.S., and which claims benefit under 35 U.S.C. § 119(e) of U.S. Provisional Application No. 61/784,234, filed Mar. 14, 2013, the content of which is incorporated herein in their entireties.

STATEMENT REGARDING FEDERALLY-SPONSORED RESEARCH

This invention was made with government support under Grant No. 2P50 CA89393-06 awarded by the National Cancer Institute. The Government has certain rights in the invention.

SEQUENCE LISTING

The instant application contains a Sequence Listing which has been submitted electronically in ASCII format and is hereby incorporated by reference in its entirety. Said ASCII copy, created on Nov. 18, 2015, is named 701039-075882-US_SL.txt and is 512 bytes in size.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Breast cancer is recognized as a collection of malignancies that all arise in the breast but are remarkably heterogeneous. Gene expression array experiments have defined at least 4 major subtypes: 1) Luminal A; 2) Luminal B; 3) HER2+; and 4) Basal. There is a strong correlation between clinically defined triple negative breast cancer "TNBC", as defined by the absence of ER, PgR, and HER2 by standard immunohistochemical staining, and the molecularly defined basal subtype.

TN breast cancer accounts for only 10-15% of all incident breast cancer cases in the U.S., but results in a disproportionate number of breast cancer deaths. Women who are destined to develop metastatic TN disease typically experience a short disease free interval and have a higher degree of lung and brain involvement than patients with luminal breast cancers. Furthermore, TN breast cancer is overrepresented among patients who carry a deleterious BRCA1 germline alteration, and among women of African ancestry.

From a clinical perspective, despite substantial efforts to develop novel targeted agents, chemotherapy remains the mainstay of therapy for TN breast cancer, as trials evaluating a number of agents either in lieu of chemotherapy or in addition to chemotherapy have failed to produce any new agent that is capable of convincingly changing the natural history of the disease. In the adjuvant setting, polychemotherapy regimens have been demonstrated to improve both disease-free survival and overall survival. In the neoadjuvant setting, a favorable response to chemotherapy is associated with a low chance of relapse at 5 years. In contrast, women who have a significant amount of residual disease after a course of neoadjuvant chemotherapy have a particularly poor prognosis, with at least half experiencing a recurrence and death from TN breast cancer within 5 years. In the metastatic setting, although patients may respond to chemotherapy, the responses tend to be brief, and resistance tends to appear quickly.

Given the curative potential of chemotherapy in patients presenting with stage I-III TN breast cancer, and the initial responses (albeit often brief) seen with chemotherapy in the metastatic setting, the general direction of targeted therapy development for TN breast cancer has been to combine targeted agents with chemotherapy. Thus, even with a growing number of targeted therapies under investigation for TN breast cancer, chemotherapy is likely to be a significant component of the treatment of TN breast cancer for many years to come.

Across breast cancers as a whole, hormone receptor dependence and tumor proliferation appear to be associated with generic "chemosensitivity". Using the 70 gene signature as an example, the current classifiers typically assign a "high-risk" status to the vast majority of TN tumors, and are also unable to define whether there may be differential benefit with one class of chemotherapeutic agents over another. Thus, in both clinical practice and in conventionally designed clinical trials, the tendency is to layer new therapies directly atop existing standards, increasing the risk of both overtreatment (because some, but not all of the administered therapies are efficacious) or undertreatment (because the tumor is not sensitive to any of the specific chemotherapeutic agents contained in the treatment regimen).

Accordingly, there exists a need in the art to identify the best chemotherapy for each patient and to eliminate agents that are inert and result in toxicity without benefit.

SUMMARY OF THE INVENTION

We provide novel methods, assays, systems and kits for determining if a cancer patient is responsive to platinum-comprising therapy or anthracyclin therapy. These methods, assays, systems and kits provide a significant improvement to the "trial-and-error"—therapies used in cancer therapy. The methods allow one to personalize the treatment of a cancer patient based on the cancer cells' specific protein/gene expression profile. In other words, the methods apply the novel findings of a cancer cells responses to cancer treatment methods and allow selection of the most likely effective therapy without delay and thus significantly improve the patient's quality of life. Avoiding use of ineffective drugs will also provide a significant saving for the cost of treatment for the cancer patient, as well avoiding exposure to side effects of ineffective drugs.

The invention is based, at least in part, on the discovery that patients having increased expression of BLM and/or FANCI genes compared to a housekeeping gene or wild-type BRCA1 gene in their cancer cells are likely to respond to platinum-comprising or anthracyclin-comprising cancer therapy.

The following embodiments and aspects thereof are described and illustrated in conjunction with compositions and methods which are meant to be exemplary and illustrative, not limiting in scope.

We provide an assay for selecting a therapy for a subject having cancer, and optionally administering the therapy, the assay comprising: subjecting a sample comprising a cancer cell taken from the subject to an analysis for BLM and FANCI expression; comparing the BLM and FANCI expression to a reference value; and selecting a platinum-comprising cancer therapy for the subject when the BLM and FANCI expression is increased compared to the reference value based on the recognition that platinum-comprising cancer therapy is effective in subjects whose cancer has increased expression of BLM and FANCI, or selecting a non-platinum-comprising cancer therapy for the subject when the BLM and FANCI expression is not increased compared to the reference value based on the recognition that platinum-comprising cancer therapy is not effective in subjects whose cancer does not have increased BLM and FANCI expression compared to the reference value.

The assay may further comprise assaying the BRCA1 and/or BRCA2 status of the subject; and selecting the platinum-comprising cancer therapy for the subject when the subject is negative for BRCA1 and/or BRCA2 mutations, and the BLM and FANCI expression is increased compared to the reference value based on the recognition that platinum-comprising cancer therapy is effective in subjects whose cancer has increased expression of BLM and FANCI and who are negative for BRCA1 and/or BRCA2 mutations.

In some aspects of all the embodiments of the invention, the subject is known to be or is determined to be negative for BRCA1 and/or BRCA2 mutations.

In some aspects of all the embodiments of the invention, the assay further comprises assaying the estrogen receptor (ER), progesterone receptor (PgR), and HER2 receptor status of the subject's cancer; and selecting the platinum-comprising cancer therapy for the subject when the subject's cancer does not express a detectable quantity of ER, PgR, and HER2 receptor, and when the BLM and FANCI expression is increased compared to the reference value based on the recognition that platinum-comprising cancer therapy is effective in subjects whose cancer has increased expression of BLM and FANCI and whose cancer does not express a detectable quantity of ER, PgR, and HER2 receptor.

In some aspects of all the embodiments of the invention, the subject's cancer or cancer cell is known to not or is determined to not express a detectable quantity of ER, PgR, and HER2 receptor.

In some aspects of all the embodiments of the invention, the assay further comprises administering the selected therapy to the subject.

In some aspects of all the embodiments of the invention, the cancer is selected from breast cancer, ovarian cancer and lung cancer.

In some aspects of all the embodiments of the invention, the reference value is BRCA1 expression in the sample and the BLM and/or FANCI expression is increased by at least two-fold compared to BRCA1 expression.

In some aspects of all the embodiments of the invention, the reference value is based on at least BRCA1 gene expression in the cancer cell.

In some aspects of all the embodiments of the invention, the reference value is based on at least one housekeeping gene expression in the cancer cell.

We also provide a method for selecting platinum-comprising therapy for a subject having cancer, and optionally administering the platinum-comprising therapy, the method comprising: subjecting a sample comprising a cancer cell taken from the subject to an analysis for BLM and FANCI expression; detecting the BLM and FANCI expression in the sample compared to a reference value; and electing a platinum-comprising cancer therapy for the subject when the BLM and FANCI expression compared to a reference value is increased based on the recognition that platinum-comprising cancer therapy is effective in patients whose cancer has increased BLM and FANCI expression compared to the reference value.

In some aspects of all the embodiments of the invention, the method further comprises administering to the subject the platinum-comprising cancer therapy when the platinum-comprising cancer therapy is selected. One can further select a therapy other than platinum-comprising therapy when it is determined using the assay that the cancer is not likely responsive to platinum-comprising therapy.

In some aspects of all the embodiments of the invention, the subject is known to be or is determined to be negative for BRCA1 and/or BRCA2 mutations.

In some aspects of all the embodiments of the invention, the subject's cancer or cancer cell is known to not or determined to not express a detectable quantity of ER, PgR, and HER2 receptor.

In some aspects of all the embodiments of the invention, the cancer is selected from breast cancer, ovarian cancer and lung cancer.

In some aspects of all the embodiments of the invention, the reference value is BRCA1 expression in the sample, and the BLM and/or FANCI expression is increased by at least two-fold compared to BRCA1 expression.

In some aspects of all the embodiments of the invention, the reference value is based on at least BRCA1 gene expression in the cancer cell.

In some aspects of all the embodiments of the invention, the reference value is based on at least one housekeeping gene expression in the cancer cell.

In some aspects of all the embodiments of the invention, the housekeeping gene is selected from beta-actin, GAPDH, RPLP0, GUS, TFRC and any combination thereof.

In some aspects of all the embodiments of the invention, the housekeeping gene is RPLP0, and the BLM and/or FANCI expression is increased by at least six-fold.

We further provide a method for selecting a non-platinum-comprising therapy, and optionally administering the non-platinum-comprising therapy, for a subject having cancer comprising: subjecting a sample comprising a cancer cell taken from the subject to an analysis for BLM and FANCI expression; detecting the BLM and FANCI expression in the sample compared to a reference value; and selecting the non-platinum-comprising cancer therapy for the subject when the BLM and FANCI expression compared to the reference value is not increased based on the recognition that non-platinum-comprising cancer therapy is effective in patients whose cancer does not have increased gene expression of BLM and FANCI compared to the reference value.

In some aspects of all the embodiments of the invention, the method further comprises administering to the subject the non-platinum-comprising cancer therapy when non-platinum-comprising cancer therapy is selected.

In some aspects of all the embodiments of the invention, the cancer is selected from breast cancer, ovarian cancer and lung cancer.

In some aspects of all the embodiments of the invention, the reference value is BRCA1 expression in the sample, and the BLM and/or FANCI expression is increased by at least two-fold compared to BRCA1 expression.

In some aspects of all the embodiments of the invention, the reference value is based on at least BRCA1 gene expression in the cancer cell.

In some aspects of all the embodiments of the invention, the reference value is based on at least one housekeeping gene expression in the cancer cell.

We provide an assay for selecting a therapy for a subject having cancer, comprising: subjecting a sample comprising a cancer cell taken from the subject to an analysis for BLM and FANCI expression; comparing the BLM and FANCI expression to a reference value; and selecting an anthracycline-comprising cancer therapy for the subject when the BLM and FANCI expression is increased compared to a reference value based on the recognition that anthracycline-comprising cancer therapy is effective in subjects whose cancer has increased expression of BLM and FANCI, or selecting a non-anthracycline-comprising cancer therapy for the subject when the BLM and FANCI expression is not increased compared to a reference value based on the recognition that anthracycline-comprising cancer therapy is not effective in subjects whose cancer does not have increased BLM expression compared to a reference value.

In some aspects of all the embodiments of the invention, the reference value is BRCA1 expression in the sample, and the BLM and/or FANCI expression is increased by at least two-fold compared to BRCA1 expression.

We provide a method for selecting an anthracycline-comprising cancer therapy for a subject having cancer and determined to be negative for BRCA1 and/or BRCA2 mutations, comprising: subjecting a sample comprising a cancer cell taken from the subject to an analysis for BLM and FANCI expression; comparing the BLM and FANCI expression to a reference value; and selecting the anthracycline-comprising cancer therapy for the subject when the BLM and FANCI expression compared to the reference value is increased based on the recognition that anthracycline-comprising cancer therapy is effective in patients whose cancer has increased expression of BLM and FANCI compared to the reference value.

In some aspects of all the embodiments of the invention, wherein the reference value is BRCA1 expression in the sample, and the BLM and/or FANCI expression is increased by at least two-fold compared to BRCA1 expression.

We further provide a method of treating cancer in a human subject, comprising: detecting BLM and FANCI expression in a sample comprising a cancer cell taken from the human subject; and comparing the BLM and FANCI expression to a reference value; and administering a platinum-comprising cancer therapy to the human subject wherein an increase of BLM and FANCI expression compared to the reference value is detected.

In some aspects of all the embodiments of the invention, the human subject's cancer or cancer cell is known to not or is determined to not express detectable quantities of estrogen receptor (ER), progesterone receptor (PgR) and HER2 receptor.

In some aspects of all the embodiments of the invention, the cancer is selected from breast, ovarian, and lung cancers.

In some aspects of all the embodiments of the invention, the reference value is BRCA1 expression in the sample, and the BLM and/or FANCI expression is increased by at least two-fold compared to BRCA1 expression.

In some aspects of all the embodiments of the invention, the reference value is based on BRCA1 gene expression in the cancer cell.

In some aspects of all the embodiments of the invention, the reference value is based on a housekeeping gene expression in the cancer cell.

We provide method of treating cancer in a human subject, comprising: detecting BLM and FANCI expression in a sample comprising a cancer cell taken from the human subject; and comparing the BLM and FANCI expression to a reference value; and administering an anthracycline-comprising cancer therapy to the human subject wherein an increase of BLM and FANCI expression compared to the reference value is detected.

In some aspects of all the embodiments of the invention, the human subject's cancer or cancer cell is known to not or is determined to not to express detectable quantities of estrogen receptor (ER), progesterone receptor (PgR) and HER2 receptor.

In some aspects of all the embodiments of the invention, the cancer is selected from breast, ovarian, and lung cancers.

In some aspects of all the embodiments of the invention, the reference value is BRCA1 expression in the sample, and the BLM and/or FANCI expression is increased by at least two-fold compared to BRCA1 expression.

In some aspects of all the embodiments of the invention, the reference value is based on BRCA1 gene expression in the cancer cell.

In some aspects of all the embodiments of the invention, the reference value is based on a housekeeping gene expression in the cancer cell.

We provide a method for assessing responsiveness of a cancer cell to cancer therapy, comprising: assaying, in a cancer cell or mRNA derived therefrom, BLM and FANCI expression; and comparing said BLM and FANCI expression to a reference value, wherein the cancer cell is assessed as responsive to a platinum-comprising therapy if the BLM and FANCI expression is increased compared to the reference value, or wherein the cancer cell is assessed as poorly or not responsive to platinum-comprising cancer therapy cancer if the BLM and FANCI expression is not increased.

In some aspects of all the embodiments of the invention, the step of assaying comprises: contacting the cancer cell or mRNA derived therefrom with at least one detectably labeled probe capable of specifically binding to BLM mRNA, at least one detectably probe capable of specifically binding to FANCI, at least one detectably labeled probe capable of specifically binding to BRCA1 and/or at least one housekeeping gene; and measuring the expression of BLM and FANCI compared to the BRCA1 and/or the at least one housekeeping gene.

In some aspects of all the embodiments of the invention, the reference value is BRCA1 expression in the sample, and the BLM and/or FANCI expression is increased by at least two-fold compared to BRCA1 expression.

We provide a method of predicting a cancer patient's response to a cancer treatment regimen comprising platinum or anthracycline, comprising: determining, in a cancer cell from the cancer patient, BLM and FANCI expression; and correlating the expression to a reference value, wherein when the expression is increased the patient is predicted to respond well to a cancer treatment regimen comprising platinum or anthracycline.

In some aspects of all the embodiments of the invention, the reference value is BRCA1 expression in the sample, and the BLM and/or FANCI expression is increased by at least two-fold compared to BRCA1 expression.

We also provide a method of predicting a cancer patient's response to a cancer treatment regimen comprising platinum or anthracycline, comprising: determining, in a cancer cell or mRNA derived therefrom from said cancer patient, BLM and FANCI expression; and correlating the expression to a reference value, wherein when the expression is not increased the patient is predicted to respond poorly to a cancer treatment regimen comprising platinum or anthracycline.

In some aspects of all the embodiments of the invention, the reference value is BRCA1 expression in the sample, and the BLM and/or FANCI expression is increased by at least two-fold compared to BRCA1 expression.

We provide a method of treating cancer, comprising: assaying, in a cancer cell from a cancer patient or mRNA obtained therefrom, the BLM and FANCI expression compared to a reference value; and administering to the cancer patient a cancer treatment regimen comprising platinum or anthracycline if the BLM and FANCI expression is increased compared to the reference value.

In some aspects of all the embodiments of the invention, the reference value is BRCA1 expression in the sample, and the BLM and/or FANCI expression is increased by at least two-fold compared to BRCA1 expression.

We also provide a use of platinum comprising cancer therapy for treating a cancer patient that has been determined to have a tumor comprising cancer cells wherein BLM and FANCI expression is increased compared to a reference value.

In some aspects of all the embodiments of the invention, the cancer patient has been determined to be negative for BRCA1 and/or BRCA2 mutations.

In some aspects of all the embodiments of the invention, the cancer patient's cancer or cancer cell is known to not or is determined to not express detectable quantities of estrogen receptor (ER), progesterone receptor (PgR) and HER2 receptor.

In some aspects of all the embodiments of the invention, the reference value is BRCA1 expression in the sample, and the BLM and/or FANCI expression is increased by at least two-fold compared to BRCA1 expression.

We provide a system for determining responsiveness of a cancer cell to platinum-comprising therapy from a cancer cell of a cancer patient, comprising: a sample analyzer configured to produce a signal for the mRNA from each one of BLM and FANCI from a cancer cell sample of a cancer patient; and a computer sub-system programmed to calculate, based on the mRNA whether the signal is greater or not than a reference value.

In some aspects of all the embodiments of the invention, said computer sub-system is programmed to compare the mRNA to determine a likelihood of responsiveness of said cancer cell to platinum-comprising cancer therapy based on an algorithm that classifies the patient as likely to respond to a platinum-comprising therapy if the BLM and FANCI expression is increased and as unlikely to respond to the platinum-comprising therapy if the BLM and FANCI expression is not increased; or a likelihood of responsiveness of said cancer cell to anthracycline-comprising cancer therapy based on an algorithm that classifies the patient as likely to respond to a anthracycline-comprising therapy if the BLM and FANCI expression is increased and as unlikely to respond to the anthracycline-comprising therapy if the BLM and FANCI expression is not increased.

In some aspects of all the embodiments of the invention, the reference value is BRCA1 expression, and the BLM and/or FANCI expression is increased by at least two-fold compared to BRCA1 expression.

We provide a computer program product embodied in a computer readable medium that, when executing on a computer, performs steps comprising: detecting the BLM and FANCI gene expression in sample comprising a cancer cell from a cancer patient; and comparing the BLM and FANCI expression to a reference value.

In some aspects of all the embodiments of the invention, the reference value is BRCA1 expression, and the BLM and/or FANCI expression is increased by at least two-fold compared to BRCA1 expression.

We provide a diagnostic kit for detecting a likelihood of a cancer patient to respond to platinum- or anthracycline-comprising comprising cancer therapy, comprising: no more than 10 probes comprising a combination of detectably labeled probes or primers for BLM and FANCI, and optionally for BRCA1 and/or at least one housekeeping gene; and a computer program product as described herein.

We provide use of a plurality of oligonucleotides comprising no more than 10 oligonucleotides capable of hybridizing to BLM and FANCI, and optionally to BRCA1 and/or at least one housekeeping gene, in a diagnostic kit for determining an increased likelihood that a cancer patient will respond to cancer treatment regimen comprising a platinum and/or anthracycline.

In some aspects of all the embodiments of the invention, said anthracycline is epirubincin or doxorubicin.

In some aspects of all the embodiments of the invention, said platinum comprising cancer therapy comprises cisplatinum or cis-diamminedichloroplatinum, phenanthriplatin, carboplatin, oxaliplatin, or a platinum complex that is activated by ultraviolet A light.

We provide an assay for selecting a therapy for a subject having cancer, and optionally administering the therapy, the assay comprising: assaying a sample comprising a cancer cell taken from the subject for a chromosome 15q26 copy number; comparing the chromosome 15q26 copy number to a reference value; and selecting a platinum-comprising cancer therapy for the subject if there is a chromosome 15q26 copy number gain compared to the reference value, or selecting a non-platinum-comprising cancer therapy for the subject if there is not a chromosome 15q26 copy number gain, or if there is a chromosome 15q26 copy number loss.

In some aspects of all the embodiments of the invention, the assay further comprises: assaying the BRCA1 and/or BRCA2 status of the subject; and selecting the platinum-comprising cancer therapy for the subject when the subject is negative for BRCA1 and/or BRCA2 mutations, and there is a chromosome 15q26 copy number gain based on the recognition that platinum-comprising cancer therapy is effective in subjects who have a chromosome 15q26 copy number gain who are negative for BRCA1 and/or BRCA2 mutations.

In some aspects of all the embodiments of the invention, the subject is known to be or is determined to be negative for BRCA1 and/or BRCA2 mutations.

In some aspects of all the embodiments of the invention, the assay further comprises: assaying the estrogen receptor (ER), progesterone receptor (PgR), and HER2 receptor status of the subject's cancer; and selecting the platinum-comprising cancer therapy for the subject when the subject's cancer does not express a detectable quantity of ER, PgR, and HER2 receptor, and when there is a chromosome 15q26 copy number gain based on the recognition that platinum-comprising cancer therapy is effective in subjects who have a chromosome 15q26 copy number gain and whose cancer does not express a detectable quantity of ER, PgR, and HER2 receptor.

In some aspects of all the embodiments of the invention, the subject's cancer or cancer cell is known to not or is determined to not express a detectable quantity of ER, PgR, and HER2 receptor.

In some aspects of all the embodiments of the invention, the assay further comprises administering the selected therapy to the subject.

In some aspects of all the embodiments of the invention, the cancer is selected from breast cancer, ovarian cancer and lung cancer.

In some aspects of all the embodiments of the invention, the reference value is chromosome 15 centromere copy number in the sample.

We provide an assay for selecting a therapy for a subject having cancer, and optionally administering the therapy, the assay comprising: assaying a sample comprising a cancer cell taken from the subject for a chromosome 15q26 copy number; comparing the chromosome 15q26 copy number to a reference value; and selecting an anthracycline-comprising cancer therapy for the subject if there is a chromosome 15q26 copy number gain compared to the reference value, or selecting a non-anthracycline-comprising cancer therapy for the subject if there is not a chromosome 15q26 copy number gain, or if there is a chromosome 15q26 copy number loss.

In some aspects of all the embodiments of the invention, the assay further comprises: assaying the BRCA1 and/or BRCA2 status of the subject; and selecting the anthracycline-comprising cancer therapy for the subject when the subject is negative for BRCA1 and/or BRCA2 mutations, and there is a chromosome 15q26 copy number gain based on the recognition that anthracycline-comprising cancer therapy is effective in subjects who have a chromosome 15q26 copy number gain who are negative for BRCA1 and/or BRCA2 mutations.

In some aspects of all the embodiments of the invention, the subject is known to be or is determined to be negative for BRCA1 and/or BRCA2 mutations.

In some aspects of all the embodiments of the invention, the assay further comprises assaying the estrogen receptor (ER), progesterone receptor (PgR), and HER2 receptor status of the subject's cancer; and selecting the anthracycline-comprising cancer therapy for the subject when the subject's cancer does not express a detectable quantity of ER, PgR, and HER2 receptor, and when there is a chromosome 15q26 copy number gain based on the recognition that anthracycline-comprising cancer therapy is effective in subjects who have a chromosome 15q26 copy number gain and whose cancer does not express a detectable quantity of ER, PgR, and HER2 receptor.

In some aspects of all the embodiments of the invention, the subject's cancer or cancer cell is known to not or is determined to not express a detectable quantity of ER, PgR, and HER2 receptor.

In some aspects of all the embodiments of the invention, the assay further comprises administering the selected therapy to the subject.

In some aspects of all the embodiments of the invention, the cancer is selected from breast cancer, ovarian cancer and lung cancer.

In some aspects of all the embodiments of the invention, the reference value is chromosome 15 centromere copy number in the sample.

We provide a method of treating cancer in a human subject, comprising: detecting a chromosome 15q26 copy number in a sample comprising a cancer cell taken from the subject; comparing the chromosome 15q26 copy number to a reference value; and administering an platinum-comprising cancer therapy for the subject if there is a chromosome 15q26 copy number gain compared to the reference value, or administering a non-platinum-comprising cancer therapy for the subject if there is not a chromosome 15q26 copy number gain, or if there is a chromosome 15q26 copy number loss.

In some aspects of all the embodiments of the invention, the cancer is selected from breast cancer, ovarian cancer and lung cancer.

In some aspects of all the embodiments of the invention, the reference value is chromosome 15 centromere copy number in the sample.

In some aspects of all the embodiments of the invention, the subject's cancer is known to not express a detectable quantity of ER, PgR, and HER2 receptor.

We provide a method of treating cancer in a human subject, comprising: detecting a chromosome 15q26 copy number in a sample comprising a cancer cell taken from the subject; comparing the chromosome 15q26 copy number to a reference value; and administering an anthracycline-comprising cancer therapy for the subject if there is a chromosome 15q26 copy number gain compared to the reference value, or administering a non-anthracycline-comprising cancer therapy for the subject if there is not a chromosome 15q26 copy number gain, or if there is a chromosome 15q26 copy number loss.

In some aspects of all the embodiments of the invention, the cancer is selected from breast cancer, ovarian cancer and lung cancer.

In some aspects of all the embodiments of the invention, the reference value is chromosome 15 centromere copy number in the sample.

In some aspects of all the embodiments of the invention, the subject's cancer or cancer cell is known to not or is determined to not express a detectable quantity of ER, PgR, and HER2 receptor.

We provide a method for assessing responsiveness of a cancer cell to a cancer therapy, and optionally administering the cancer therapy, comprising: assaying a sample comprising a cancer cell taken from the subject for a chromosome 15q26 copy number; and comparing the chromosome 15q26 copy number to a reference value, wherein the cancer cell is assessed as responsive to a platinum-comprising therapy if there is a chromosome 15q26 copy number gain compared to the reference value, or wherein the cancer cell is assessed as poorly or not responsive to platinum-comprising cancer therapy cancer if there is not a chromosome 15q26 copy number gain or if there is a chromosome 15q26 copy number loss.

In some aspects of all the embodiments of the invention, the reference value is copy number of chromosome 15.

In some aspects of all the embodiments of the invention, the cancer is selected from breast cancer, ovarian cancer and lung cancer.

In some aspects of all the embodiments of the invention, the method further comprises administering the platinum-comprising therapy if there is a chromosome 15q26 copy number gain.

We provide a method of predicting a cancer patient's response to a cancer treatment regimen comprising platinum or anthracycline, comprising: determining, in a cancer cell from the cancer patient, chromosome 15q26 copy number; and correlating the chromosome 15q26 copy number to a reference value, wherein when there is a chromosome 15q26 copy number gain, the patient is predicted to respond well to a cancer treatment comprising platinum or anthracycline, or wherein when there is not a chromosome 15q26 copy number gain or a chromosome 15q26 copy number loss, the patient is predicted respond poorly to a cancer treatment comprising platinum or anthracycline.

In some aspects of all the embodiments of the invention, the reference value is chromosome 15 centromere copy number in the sample.

We provide use of platinum comprising cancer therapy for treating a cancer patient that has been determined to have a tumor comprising cancer cells wherein a chromosome 15q26 copy gain is detected compared to a reference value.

In some aspects of all the embodiments of the invention, the cancer patient is known to be or is determined to be negative for BRCA1 and/or BRCA2 mutations.

In some aspects of all the embodiments of the invention, the cancer patient's cancer or cancer cell is known to not or is determined to not express detectable quantities of estrogen receptor (ER), progesterone receptor (PgR) and HER2 receptor.

In some aspects of all the embodiments of the invention, the reference value is chromosome 15 centromere copy number in the sample.

We provide a system for determining responsiveness of a cancer cell to platinum-comprising therapy from a cancer cell of a cancer patient, comprising: a sample analyzer configured to produce a signal for chromosome 15q26 copy number from a cancer cell sample of a cancer patient; and a computer sub-system programmed to calculate, based on the mRNA whether the signal is greater or not than a reference value.

In some aspects of all the embodiments of the invention, said computer sub-system is programmed to compare the mRNA to determine a likelihood of responsiveness of said cancer cell to platinum-comprising cancer therapy and/or or a anthracycline-comprising cancer therapy based on an algorithm that classifies the patient as likely to respond to a platinum-comprising therapy if there is a chromosome 15q26 copy number gain and as unlikely to respond to the platinum-comprising therapy if there is not a chromosome 15q26 copy number gain or if there is a chromosome 15q26 copy number loss.

In some aspects of all the embodiments of the invention, the reference value is chromosome 15 centromere copy number in the sample.

We provide a computer program product embodied in a computer readable medium that, when executing on a computer, performs steps comprising: detecting chromosome 15q26 copy number in sample comprising a cancer cell from a cancer patient; and comparing the chromosome 15q26 copy number to a reference value.

In some aspects of all the embodiments of the invention, the reference value is chromosome 15 centromere copy number in the sample.

We provide a diagnostic kit for detecting a likelihood of a cancer patient to respond to platinum- or anthracycline-comprising cancer therapy, comprising: no more than 10 probes comprising a combination of detectably labeled probes or primers for chromosome 15q26, and optionally for chromosome 15 centromere; and a computer program as described herein.

We provide us of a plurality of oligonucleotides comprising no more than 10 oligonucleotides capable of hybridizing to chromosome 15q26, and optionally for chromosome 15 centromere, in a diagnostic kit for determining an increased likelihood that a cancer patient will respond to cancer treatment regimen comprising a platinum and/or anthracycline.

In some aspects of all the embodiments of the invention, said anthracycline is epirubincin or doxorubicin.

In some aspects of all the embodiments of the invention, said platinum comprising cancer therapy comprises cisplatinum or cis-diamminedichloroplatinum, phenanthriplatin, carboplatin, oxaliplatin, or a platinum complex that is activated by ultraviolet A light.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

This patent or application file contains at least one drawing executed in color. Copies of this patent or patent application publication with color drawings will be provided by the Office upon request and payment of the necessary fee.

Exemplary embodiments are illustrated in referenced figures. It is intended that the embodiments and figures disclosed herein are to be considered illustrative rather than restrictive.

FIG. 10A shows receiver operating characteristic curves showing the ability of the BRCA1-BLM-FANCI RNA 3-gene signature to predict for response to cisplatin in the two cisplatin trials. FIG. 10B shows ROC curves showing the ability of number of telomeric allelic imbalance (NtAI)+3-gene mRNA signature to predict for sensitivity to cisplatin in the combined trials.

FIG. 19 shows FANCI/RPLP0 signature. FANCI is compared to a housekeeping gene, RPLP0. The optimum ratio is higher than BRCA1 alone.

DETAILED DESCRIPTION

Figure 1A:
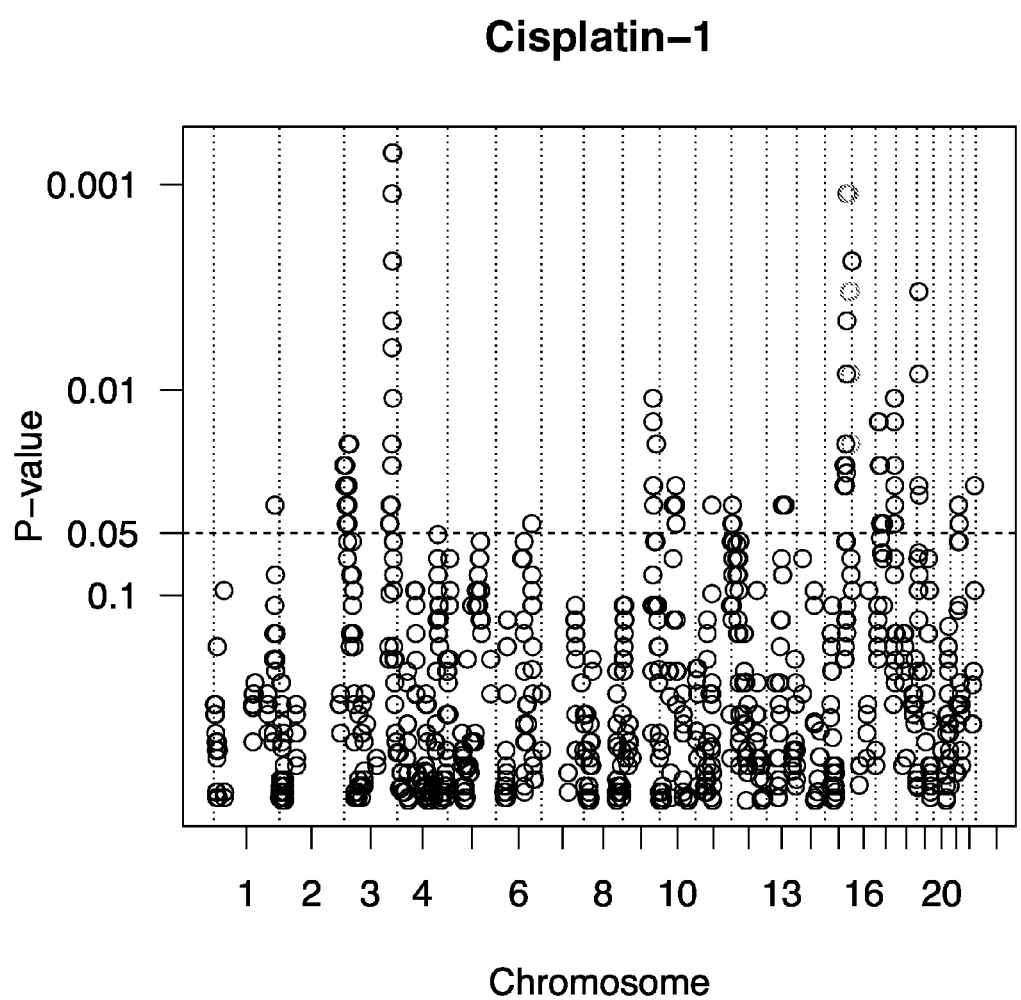
FIGS. 1A and 1B show that GISTIC identifies 169 chromosomal regions as either gained or lost. Several contained genes with significantly different copy number between sensitive and resistant cases.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application. For references on how to prepare antibodies, see D. Lane, *Antibodies: A Laboratory Manual* (Cold Spring Harbor Press, Cold Spring Harbor N.Y., 1988); Kohler and Milstein, (1976) Eur. J. Immunol. 6: 511; Queen et al. U.S. Pat. No. 5,585,089; and Riechmann et al., Nature 332: 323 (1988).

One skilled in the art will recognize many methods and materials similar or equivalent to those described herein, which could be used in the practice of the present invention. Indeed, the present invention is in no way limited to the methods and materials described.

To investigate whether specific genomic aberrations may affect cancer sensitivity to cisplatin, the inventors generated tumor DNA copy number profiles of 21 and 24 TNBC patients who received pre-operative cisplatin-based chemotherapy in two separate clinical trials. Using the GISTIC algorithm (1), the inventors found that only a single region on chromosome 15q26 showed consistent significant differential copy number in responders versus non-responders, being preferentially lost in non-responders, but preferentially gained in responders in both trials.

To see if genes on 15q26 were associated with platinum sensitivity, the inventors acquired gene expression data from the cisplatin TNBC trial (2), and from the carboplatin-only arm of an ovarian cancer trial (3). The inventors then performed a leave-one-out analysis, and found 9 genes significantly associated with platinum response in at least 75% of all rounds in both cohorts. These included BLM and FANCI located in the 15q26 region, both showing higher expression in sensitive tumors, and known to be involved in related DNA repair processes. To investigate if BLM and FANCI were specifically associated with genotoxic chemotherapy sensitivity, the inventors analyzed their expression in TNBCs from three neoadjuvant trials of epirubicin alone (4) or taxane-containing combination therapy (5, 6) and in ovarian cancers from the taxane-only treatment arm (3). In the epirubicin trial, BLM and FANCI expression was again significantly associated with increased sensitivity to therapy. In contrast, there was no association between either BLM or FANCI expression and TNBC response to the taxane-containing regimen or ovarian cancer response to single agent taxane treatment. These data suggest that high expression of BLM and FANCI are associated with improved response to DNA damaging agents, but not with response to other types of chemotherapeutics. Furthermore, it suggests that the patient subpopulations that respond to drugs such as anthracyclines and taxanes are not overlapping, and that it will therefore be difficult to robustly identify predictors of single agent response based on multi-drug trials.

While not wishing to be bound by any particular theory, the inventors believe that FANCI and BLM functions in multiple DNA repair processes; increased FANCI and BLM is associated with response to platinum-comprising therapy and anthracycline-comprising therapy; low copy gain might be a compensatory mechanism of HR deficient cells, trying to rescue some DNA repair capacity; and if so, FANCI/BLM expression is a marker for DNA repair deficiency, and increased sensitivity to genotoxic chemotherapy drugs, such as platinum-comprising therapy and anthracycline-comprising therapy.

Therefore, while the cancers specifically investigated for their responses in the particular studies, such as breast cancer, such as triple negative breast cancer, ovarian cancer and lung cancer, Applicants believe that the finding of the association between increased FANCI and BLM expression and responsiveness to platinum-comprising therapy and anthracycline-comprising therapy is applicable to most cancers.

The present invention is based, at least in part, on these findings, and those further described herein and in the figures and examples.

Selecting Therapy

Various embodiments provide for assays, methods and systems for selecting an appropriate therapy for a subject based on an analysis of the subject's BLM and FANCI expression, or based on the subject's 15q26 copy number.

In various embodiments, the invention provide for an assay for selecting a therapy, and optionally administering the therapy, for a subject having cancer, the assay comprising: subjecting a sample comprising a cancer cell taken from the subject to an analysis for BLM and FANCI expression; comparing the BLM and FANCI expression to a reference value; and selecting a platinum-comprising cancer therapy for the subject when the BLM and FANCI expression is increased compared to the reference value based on the recognition that platinum-comprising cancer therapy is effective in subjects whose cancer has increased expression of BLM and FANCI, or selecting a non-platinum-comprising cancer therapy for the subject when the BLM and FANCI expression is not increased compared to the reference value based on the recognition that platinum-comprising cancer therapy is not effective in subjects whose cancer does not have increased BLM and FANCI expression compared to the reference value.

In various embodiments, the assay further comprises: assaying the BRCA1 and/or BRCA2 status of the subject; and selecting the platinum-comprising cancer therapy for the subject when the subject is negative for BRCA1 and/or BRCA2 mutations, and the BLM and FANCI expression is increased compared to the reference value based on the recognition that platinum-comprising cancer therapy is effective in subjects whose cancer has increased expression of BLM and FANCI and who are negative for BRCA1 and/or BRCA2 mutations. In various embodiments, the subject is known to be or is determined to be negative for BRCA1 and/or BRCA2 mutations. The determination can be made before, concurrently with, or after the analysis for BLM and FANCI expression.

In some aspects of all the embodiments of the invention, a mutation that inactivates BRCA2 is highly predictive of response.

In various embodiments, the assay further comprises: assaying the estrogen receptor (ER), progesterone receptor (PgR), and HER2 receptor status of the subject's cancer; and selecting the platinum-comprising cancer therapy for the subject when the subject's cancer does not express a detectable quantity of ER, PgR, and HER2 receptor, and when the BLM and FANCI expression is increased compared to the reference value based on the recognition that platinum-comprising cancer therapy is effective in subjects whose cancer has increased expression of BLM and FANCI and whose cancer does not express a detectable quantity of ER, PgR, and HER2 receptor. In various embodiments, the subject's cancer or cancer cell is known to not or is determined to not express a detectable quantity of ER, PgR, and HER2 receptor. The determination can be made before, concurrently with, or after analysis for BLM and FANCI expression.

In various embodiments, the assay further comprises administering the selected therapy to the subject.

In various embodiments, the cancer is selected from breast cancer, ovarian cancer and lung cancer.

In various embodiments, the reference value is based on BRCA1 gene expression in the cancer cell. In various embodiments, the reference value is BRCA1 expression, and the BLM and/or FANCI expression is increased by at least or about 10, 20, 30, 40, 50, 60, 70, 80, or 90% compared to BRCA1 expression.

In various embodiments, the reference value is BRCA1 expression, and the BLM and/or FANCI expression is increased by at least or about 1-fold, 1.1-fold, 1.2-fold, 1.3-fold, 1.4-fold, 1.5-fold, 1.6-fold, 1.7-fold, 1.8-fold, 1.9-fold, 2-fold, 2.1-fold 2.2-fold 2.3-fold 2.4-fold 2.5-fold, 2.6-fold, 2.7-fold, 2.8-fold, 2.9-fold, 3-fold, 4-fold, 5-fold, or 6-fold, 10-20 fold, 20-50 fold or higher, depending on the expression level of the gene used as a standard, such as one or more housekeeping genes or BRCA1.

Typically, an increase in expression of at least 1.5 or at least 2 fold is considered as a cut-off point for increased expression if BRCA1 gene expression is used as a standard. Thus, in certain embodiments, the reference value is BRCA1 expression, and the BLM and/or FANCI expression is increased by at least two-fold compared to BRCA1 expression.

For example, in our examples, we calculated the ratios, and in cells expressing wild type BRCA1 (wtBRCA1) the ratio was around 6.6 for BLM+FANCI/BRCA1. Thus, is some aspects, the expression level can be over 5, or over 6 or over 7 times that of BRCA1.

For analysis with qPCR, each of the analyzed genes is first normalized to a housekeeping gene, such as RPLP0. For example, with 6 cycles of PCT, we calculated the optimum for BRCA1/BLM/FANCI normalized to RPLP0, expression of which is typically very low. All values are log2, which means that a ratio of 6 reflects an amount of 64 times higher than the reference gene, namely RPLP0.

In various embodiments, the reference value is based on a housekeeping gene expression in the cancer cell. Examples of useful housekeeping genes are described herein, e.g., in Table 1.

Various embodiments of the present invention provide for a method for selecting platinum-comprising therapy, and optionally administering the platinum-comprising therapy, for a subject having cancer, comprising: subjecting a sample comprising a cancer cell taken from the subject to an analysis for BLM and FANCI expression; detecting the BLM and FANCI expression in the sample compared to a reference value; and selecting a platinum-comprising cancer therapy for the subject when the BLM and FANCI expression compared to a reference value is increased based on the recognition that platinum-comprising cancer therapy is effective in patients whose cancer has increased BLM and FANCI expression compared to the reference value.

In various embodiments, the method further comprises administering to the subject the platinum-comprising cancer therapy when the platinum-comprising cancer therapy is selected.

In various embodiments, the subject is known to be or is determined to be negative for BRCA1 and/or BRCA2 mutations. The determination can be made before, concurrently with, or after the analysis for BLM and FANCI expression. In various embodiments, the subject's cancer or cancer cell is known to not or is determined to not express a detectable quantity of ER, PgR, and HER2 receptor. The determination can be made before, concurrently with, or after analysis for BLM and FANCI expression.

In various embodiments, the reference value is based on BRCA1 gene expression in the cancer cell. In various embodiments, the reference value is BRCA1 expression, and the BLM and/or FANCI expression is increased by at least or about 10, 20, 30, 40, 50, 60, 70, 80, or 90% compared to BRCA1 expression.

In various embodiments, the reference value is BRCA1 expression, and the BLM and/or FANCI expression is increased by at least or about 1-fold, 1.1-fold, 1.2-fold, 1.3-fold, 1.4-fold, 1.5-fold, 1.6-fold, 1.7-fold, 1.8-fold, 1.9-fold, 2-fold, 2.1-fold 2.2-fold 2.3-fold 2.4-fold 2.5-fold, 2.6-fold, 2.7-fold 2.8-fold 2.9-fold or 3-fold compared to BRCA1 expression. In certain embodiments, the reference value is BRCA1 expression, and the BLM and/or FANCI expression is increased by at least or about two-fold compared to BRCA1 expression. In certain embodiments, the BLM and/or FANCI expression is increased by at least or about 6-fold compared to BRCA1 expression.

In various embodiments, the reference value is based on a housekeeping gene expression in the cancer cell. Housekeeping genes are described herein.

In certain embodiments, the cancer is selected from breast cancer, ovarian cancer and lung cancer.

Various embodiments of the present invention provide for a method for selecting a non-platinum-comprising therapy, and optionally administering the non-platinum-comprising therapy, for a subject having cancer comprising: subjecting a sample comprising a cancer cell taken from the subject to an analysis for BLM and FANCI expression; detecting the BLM and FANCI expression in the sample compared to a reference value; and selecting the non-platinum-comprising cancer therapy for the subject when the BLM and FANCI expression compared to the reference value is not increased based on the recognition that non-platinum-comprising cancer therapy is effective in patients whose cancer does not have increased gene expression of BLM and FANCI compared to the reference value.

In some aspects of all the embodiments of the invention a dual assay allowing analysis of both BLM and FANCI expression to be compared in the same assay is used. The dual assay may be based on detecting RNA or protein. The assay may be specific for the dual analysis of BLM and FANCI or may comprise reagents for assaying one, two, three or more other biomolecules as well. In some aspects of all the embodiments of the invention the one other biomolecule is BRCA1.

In various embodiments, the method further comprises administering to the subject the non-platinum-comprising cancer therapy when non-platinum-comprising cancer therapy is selected.

In various embodiments, the reference value is based on BRCA1 gene expression in the cancer cell. In various embodiments, the reference value is BRCA1 expression, and the BLM and/or FANCI expression is increased by at least or about 10, 20, 30, 40, 50, 60, 70, 80, or 90% compared to BRCA1 expression.

In various embodiments, the reference value is BRCA1 expression, and the BLM and/or FANCI expression is increased by at least or about 1-fold, 1.1-fold, 1.2-fold, 1.3-fold, 1.4-fold, 1.5-fold, 1.6-fold, 1.7-fold, 1.8-fold, 1.9-fold, 2-fold, 2.1-fold 2.2-fold 2.3-fold 2.4-fold 2.5-fold, 2.6-fold, 2.7-fold 2.8-fold 2.9-fold or 3-fold compared to BRCA1 expression. In certain embodiments, the reference value is BRCA1 expression, and the BLM and/or FANCI expression is increased by at least two-fold compared to BRCA1 expression.

In various embodiments, the reference value is based on a housekeeping gene expression in the cancer cell. Examples of housekeeping genes are described herein although these genes are well known to one of ordinary skill in the art.

In various embodiments, the cancer is selected from breast cancer, ovarian cancer and lung cancer.

Various embodiments of the present invention provide for an assay for selecting a therapy for a subject having cancer, comprising: subjecting a sample comprising a cancer cell taken from the subject to an analysis for BLM and FANCI expression; comparing the BLM and FANCI expression, optionally in a dual assay, to a reference value; and selecting an anthracycline-comprising cancer therapy for the subject when the BLM and FANCI expression is increased compared to a reference value based on the recognition that anthracycline-comprising cancer therapy is effective in subjects whose cancer has increased expression of BLM and FANCI, or selecting a non-anthracycline-comprising cancer therapy for the subject when the BLM and FANCI expression is not increased compared to a reference value based on the recognition that anthracycline-comprising cancer therapy is not effective in subjects whose cancer does not have increased BLM expression compared to a reference value.

Various embodiments of the present invention provide for a method for selecting an anthracycline-comprising cancer therapy for a subject having cancer and determined to be negative for BRCA1 and BRCA2 mutations, comprising: subjecting a sample comprising a cancer cell taken from the subject to an analysis for BLM and FANCI expression comparing the BLM and FANCI expression to a reference value; and selecting the anthracycline-comprising cancer therapy for the subject when the BLM and FANCI expression compared to the reference value is increased based on the recognition that anthracycline-comprising cancer therapy is effective in patients whose cancer has increased expression of BLM and FANCI compared to the reference value.

Various embodiments provide for an assay for selecting a therapy for a subject having cancer, and optionally administering the therapy, the assay comprising: assaying a sample comprising a cancer cell taken from the subject for a chromosome 15q26 copy number; comparing the chromosome 15q26 copy number to a reference value; and selecting a platinum-comprising cancer therapy for the subject if there is a chromosome 15q26 copy number gain compared to the reference value, or selecting a non-platinum-comprising cancer therapy for the subject if there is not a chromosome 15q26 copy number gain, or if there is a chromosome 15q26 copy number loss.

In various embodiments, the assay further comprises assaying the BRCA1 and/or BRCA2 status of the subject; and selecting the platinum-comprising cancer therapy for the subject when the subject is negative for BRCA 1 and/or BRCA2 mutations, and there is a chromosome 15q26 copy number gain based on the recognition that platinum-comprising cancer therapy is effective in subjects who have a chromosome 15q26 copy number gain who are negative for BRCA1 and/or BRCA2 mutations. In various embodiments, the subject is known to be or is determined to be negative for BRCA1 and/or BRCA2 mutations. The determination can be made before, concurrently with, or after the analysis for BLM and FANCI expression.

In various embodiments, the assay further comprises assaying the estrogen receptor (ER), progesterone receptor (PgR), and HER2 receptor status of the subject's cancer; and selecting the platinum-comprising cancer therapy for the subject when the subject's cancer does not express a detectable quantity of ER, PgR, and HER2 receptor, and when there is a chromosome 15q26 copy number gain based on the recognition that platinum-comprising cancer therapy is effective in subjects who have a chromosome 15q26 copy number gain and whose cancer does not express a detectable quantity of ER, PgR, and HER2 receptor. In various embodiments, the subject's cancer or cancer cell is known to not or is determined to not express a detectable quantity of ER, PgR, and HER2 receptor. The determination can be made before, concurrently with, or after analysis for chromosome 15q26 copy number.

In various embodiments, the assay further comprises administering the selected therapy to the subject.

In various embodiments, the cancer is selected from breast cancer, ovarian cancer and lung cancer.

In various embodiments, the reference value is chromosome 15 centromere copy number.

Various embodiments of the present invention provide for an assay for selecting a therapy for a subject having cancer, and optionally administering the therapy, the assay comprising: assaying a sample comprising a cancer cell taken from the subject for a chromosome 15q26 copy number; comparing the chromosome 15q26 copy number to a reference value; and selecting an anthracycline-comprising cancer therapy for the subject if there is a chromosome 15q26 copy number gain compared to the reference value, or selecting a non-anthracycline-comprising cancer therapy for the subject if there is not a chromosome 15q26 copy number gain, or if there is a chromosome 15q26 copy number loss.

In various embodiments, the assay further comprises assaying the BRCA1 and/or BRCA2 status of the subject; and selecting the anthracycline-comprising cancer therapy for the subject when the subject is negative for BRCA1 and/or BRCA2 mutations, and there is a chromosome 15q26 copy number gain based on the recognition that anthracycline-comprising cancer therapy is effective in subjects who have a chromosome 15q26 copy number gain and who are negative for BRCA1 and/or BRCA2 mutations. In various embodiments, the subject is known to be or is determined to be negative for BRCA1 and/or BRCA2 mutations. In some aspects of all the embodiments of the invention, a mutation that inactivates BRCA2 is highly predictive of response to platinum-comprising cancer therapy. The determination can be made before, concurrently with, or after analysis for chromosome 15q26 copy number.

In various embodiments, the assay further comprises assaying the estrogen receptor (ER), progesterone receptor (PgR), and HER2 receptor status of the subject's cancer; and selecting the anthracycline-comprising cancer therapy for the subject when the subject's cancer does not express a detectable quantity of ER, PgR, and HER2 receptor, and when there is a chromosome 15q26 copy number gain based on the recognition that anthracycline-comprising cancer therapy is effective in subjects who have a chromosome 15q26 copy number gain and whose cancer does not express a detectable quantity of ER, PgR, and HER2 receptor. In various embodiments, the subject's cancer or cancer cell is known to not or is determined to not express a detectable quantity of ER, PgR, and HER2 receptor. The determination can be made before, concurrently with, or after analysis for chromosome 15q26 copy number.

In various embodiments, the assay further comprises administering the selected therapy to the subject.

In various embodiments, the cancer is selected from breast cancer, ovarian cancer and lung cancer.

In various embodiments, the reference value is chromosome 15 centromere copy number.

Cancer Treatment

Various embodiments of the present invention provide for a method of treating cancer in a human subject, comprising: detecting BLM and FANCI expression in a sample comprising a cancer cell taken from the human subject; and comparing the BLM and FANCI expression to a reference value; and administering a platinum-comprising cancer therapy to the human subject wherein an increase of BLM and FANCI expression compared to the reference value is detected.

In various embodiments, the cancer is selected from breast, ovarian, and lung cancers.

In various embodiments, the reference value is based on BRCA1 gene expression in the cancer cell. In various embodiments, the reference value is BRCA1 expression, and the BLM and/or FANCI expression is increased by at least or about 10, 20, 30, 40, 50, 60, 70, 80, or 90% compared to BRCA1 expression.

In various embodiments, the reference value is BRCA1 expression, and the BLM and/or FANCI expression is increased by at least or about 1-fold, 1.1-fold, 1.2-fold, 1.3-fold, 1.4-fold, 1.5-fold, 1.6-fold, 1.7-fold, 1.8-fold, 1.9-fold, 2-fold, 2.1-fold 2.2-fold 2.3-fold 2.4-fold 2.5-fold, 2.6-fold, 2.7-fold 2.8-fold 2.9-fold or 3-fold compared to BRCA1 expression. In certain embodiments, the reference value is BRCA1 expression, and the BLM and/or FANCI expression is increased by at least two-fold compared to BRCA1 expression.

In various embodiments, the reference value is based on a housekeeping gene expression in the cancer cell. Housekeeping genes are described herein.

In certain embodiments, the human subject's cancer or cancer cell is known to not or determined not to express detectable quantities of estrogen receptor (ER), progesterone receptor (PgR) and HER2 receptor. The determination can be made before, concurrently with, or after analysis for chromosome 15q26 copy number.

Various embodiments of the present invention provide for a method of treating cancer in a human subject, comprising: detecting BLM and FANCI expression in a sample comprising a cancer cell taken from the human subject; and comparing the BLM and FANCI expression to a reference value; and administering an anthracycline-comprising cancer therapy to the human subject wherein an increase of BLM and FANCI expression compared to the reference value is detected.

In various embodiments, the human subject's cancer is known to not or determined to not express detectable quantities of estrogen receptor (ER), progesterone receptor (PgR) and HER2 receptor. The determination can be made before, concurrently with, or after analysis for chromosome 15q26 copy number.

In various embodiments, the cancer is selected from breast, ovarian, and lung cancers.

In various embodiments, the reference value is based on BRCA1 gene expression in the cancer cell. In various embodiments, the reference value is BRCA1 expression, and the BLM and/or FANCI expression is increased by at least or about 10, 20, 30, 40, 50, 60, 70, 80, or 90% compared to BRCA1 expression.

In various embodiments, the reference value is BRCA1 expression, and the BLM and/or FANCI expression is increased by at least or about 1-fold, 1.1-fold, 1.2-fold, 1.3-fold, 1.4-fold, 1.5-fold, 1.6-fold, 1.7-fold, 1.8-fold, 1.9-fold, 2-fold, 2.1-fold 2.2-fold 2.3-fold 2.4-fold 2.5-fold, 2.6-fold, 2.7-fold 2.8-fold 2.9-fold or 3-fold compared to BRCA1 expression. In certain embodiments, the reference value is BRCA1 expression, and the BLM and/or FANCI expression is increased by at least two-fold compared to BRCA1 expression.

In various embodiments, the reference value is based on a housekeeping gene expression in the cancer cell. Housekeeping genes are described herein, e.g., in Table 1.

Various embodiments of the present invention provide for a method of treating cancer, comprising: assaying, in a cancer cell from a cancer patient or mRNA obtained therefrom, the BLM and FANCI expression compared to a reference value; and administering to the cancer patient a cancer treatment regimen comprising platinum or anthracycline if the BLM and FANCI expression is increased compared to the reference value.

Various embodiments provide for a use of platinum comprising cancer therapy for treating a cancer patient that has been determined to have a tumor comprising cancer cells wherein BLM and FANCI expression is increased compared to a reference value.

In various embodiments, the cancer patient is known to be or is determined to be negative for BRCA1 and/or BRCA2 mutations. The determination can be made before, concurrently with, or after the analysis for BLM and FANCI expression. In certain embodiments, the cancer patient's cancer or cancer cell is known to not or is determined to not express detectable quantities of estrogen receptor (ER), progesterone receptor (PgR) and HER2 receptor. The determination can be made before, concurrently with, or after analysis of BLM and FANCI expression.

Various embodiments of the present invention provide for a method of treating cancer in a human subject whose cancer has increased BLM and FANCI expression, comprising: identifying the human subject whose cancer has increased BLM and FANCI expression; and administering a platinum-comprising cancer therapy or an anthracycline-comprising therapy to the human subject. In certain embodiments, the human subject's cancer is known to not or is determined to not express detectable quantities of estrogen receptor (ER), progesterone receptor (PgR) and HER2 receptor. In various embodiments, the human subject is known to be or is determined to be negative for BRCA1 and/or BRCA2 mutations. These determinations can be made before, concurrently with, or after analysis of BLM and FANCI expression.

Various embodiments of the present invention provide for a method of treating cancer in a human subject, comprising: detecting a chromosome 15q26 copy number in a sample comprising a cancer cell taken from the subject; comparing the chromosome 15q26 copy number to a reference value; and administering an platinum-comprising cancer therapy for the subject if there is a chromosome 15q26 copy number gain compared to the reference value, or administering a non-platinum-comprising cancer therapy for the subject if there is not a chromosome 15q26 copy number gain, or if there is a chromosome 15q26 copy number loss.

In various embodiments, the cancer is selected from breast cancer, ovarian cancer and lung cancer. In various embodiments, the reference value is chromosome 15 centromere copy number. In various embodiments, the subject's cancer or cancer cell is known to not or is determined to not express a detectable quantity of ER, PgR, and HER2 receptor. The determination can be made before, concurrently with, or after analysis of chromosome 15q26 copy number.

Various embodiments of the present invention provide for a method of treating cancer in a human subject, comprising: detecting a chromosome 15q26 copy number in a sample comprising a cancer cell taken from the subject; comparing the chromosome 15q26 copy number to a reference value; and administering an anthracycline-comprising cancer therapy for the subject if there is a chromosome 15q26 copy number gain compared to the reference value, or administering a non-anthracycline-comprising cancer therapy for the subject if there is not a chromosome 15q26 copy number gain, or if there is a chromosome 15q26 copy number loss.

In various embodiments, the cancer is selected from breast cancer, ovarian cancer and lung cancer. In various embodiments, the reference value is chromosome 15 centromere copy number. In various embodiments, the subject's cancer or cancer cell is known to not or is determined to not express a detectable quantity of ER, PgR, and HER2 receptor. The determination can be made before, concurrently with, or after analysis of chromosome 15q26 copy number.

Assessing and Predicting Responsiveness to Cancer Therapy

Various embodiments of the present invention provide for a method for assessing responsiveness of a cancer cell to cancer therapy, comprising: assaying, in a cancer cell or mRNA derived therefrom, BLM and FANCI expression; and comparing said BLM and FANCI expression to a reference value, wherein the cancer cell is assessed as responsive to a platinum-comprising therapy if the BLM and FANCI expression is increased compared to the reference value, or wherein the cancer cell is assessed as poorly or not responsive to platinum-comprising cancer therapy cancer if the BLM and FANCI expression is not increased.

In various embodiments, the step of assaying comprises: contacting the cancer cell or mRNA derived therefrom with at least one detectably labeled probe capable of specifically binding to BLM mRNA, at least one detectably probe capable of specifically binding to FANCI, at least one detectably labeled probe capable of specifically binding to BRCA1 and/or at least one housekeeping gene; and measuring the expression of BLM and FANCI compared to the BRCA1 and/or the at least one housekeeping gene.

In various embodiments, the reference value is based on BRCA1 gene expression in the cancer cell. In various embodiments, the reference value is BRCA1 expression, and the BLM and/or FANCI expression is increased by at least or about 10, 20, 30, 40, 50, 60, 70, 80, or 90% compared to BRCA1 expression.

In various embodiments, the reference value is BRCA1 expression, and the BLM and/or FANCI expression is increased by at least or about 1-fold, 1.1-fold, 1.2-fold, 1.3-fold, 1.4-fold, 1.5-fold, 1.6-fold, 1.7-fold, 1.8-fold, 1.9-fold, 2-fold, 2.1-fold 2.2-fold 2.3-fold 2.4-fold 2.5-fold, 2.6-fold, 2.7-fold 2.8-fold 2.9-fold or 3-fold compared to BRCA1 expression. In certain embodiments, the reference value is BRCA1 expression, and the BLM and/or FANCI expression is increased by at least two-fold compared to BRCA1 expression.

In various embodiments, the reference value is based on a housekeeping gene expression in the cancer cell. Housekeeping genes are described herein, e.g., in Table 1.

Various embodiments of the present invention provide for a method of predicting a cancer patient's response to a cancer treatment regimen comprising platinum or anthracycline, comprising: determining, in a cancer cell from the cancer patient, BLM and FANCI expression; and correlating the expression to a reference value, wherein when the expression is increased the patient is predicted to respond well to a cancer treatment regimen comprising platinum or anthracycline.

In various embodiments, the reference value is based on BRCA1 gene expression in the cancer cell. In various embodiments, the reference value is BRCA1 expression, and the BLM and/or FANCI expression is increased by at least or about 10, 20, 30, 40, 50, 60, 70, 80, or 90% compared to BRCA1 expression.

In various embodiments, the reference value is BRCA1 expression, and the BLM and/or FANCI expression is increased by at least or about 1-fold, 1.1-fold, 1.2-fold, 1.3-fold, 1.4-fold, 1.5-fold, 1.6-fold, 1.7-fold, 1.8-fold, 1.9-fold, 2-fold, 2.1-fold 2.2-fold 2.3-fold 2.4-fold 2.5-fold, 2.6-fold, 2.7-fold 2.8-fold 2.9-fold or 3-fold compared to BRCA1 expression. In certain embodiments, the reference value is BRCA1 expression, and the BLM and/or FANCI expression is increased by at least two-fold compared to BRCA1 expression.

In various embodiments, the reference value is based on a housekeeping gene expression in the cancer cell. Housekeeping genes are described herein, e.g., in Table 1.

Various embodiments of the present invention provide for a method of predicting a cancer patient's response to a cancer treatment regimen comprising platinum or anthracycline, comprising: determining, in a cancer cell or mRNA derived therefrom from said cancer patient, BLM and FANCI expression; and correlating the expression to a reference value, wherein when the expression is not increased the patient is predicted to respond poorly to a cancer treatment regimen comprising platinum or anthracycline.

In various embodiments, the reference value is based on BRCA1 gene expression in the cancer cell. In various embodiments, the reference value is BRCA1 expression, and the BLM and/or FANCI expression is increased by at least or about 10, 20, 30, 40, 50, 60, 70, 80, or 90% compared to BRCA1 expression.

In various embodiments, the reference value is BRCA1 expression, and the BLM and/or FANCI expression is increased by at least or about 1-fold, 1.1-fold, 1.2-fold, 1.3-fold, 1.4-fold, 1.5-fold, 1.6-fold, 1.7-fold, 1.8-fold, 1.9-fold, 2-fold, 2.1-fold 2.2-fold 2.3-fold 2.4-fold 2.5-fold, 2.6-fold, 2.7-fold 2.8-fold 2.9-fold or 3-fold compared to BRCA1 expression. In certain embodiments, the reference value is BRCA1 expression, and the BLM and/or FANCI expression is increased by at least two-fold compared to BRCA1 expression.

In various embodiments, the reference value is based on a housekeeping gene expression in the cancer cell. Housekeeping genes are described herein.

Various embodiments provide for a method for assessing responsiveness of a cancer cell to a cancer therapy, and optionally administering the cancer therapy, comprising: assaying a sample comprising a cancer cell taken from the subject for a chromosome 15q26 copy number; and comparing the chromosome 15q26 copy number to a reference value, wherein the cancer cell is assessed as responsive to a platinum-comprising therapy if there is a chromosome 15q26 copy number gain compared to the reference value, or wherein the cancer cell is assessed as poorly or not responsive to platinum-comprising cancer therapy cancer if there is not a chromosome 15q26 copy number gain or if there is a chromosome 15q26 copy number loss.

In various embodiments, the reference value is chromosome 15 centromere copy number. In various embodiments, the cancer is selected from breast cancer, ovarian cancer and lung cancer.

In various embodiments, the method further comprises administering the platinum-comprising therapy if there is a chromosome 15q26 copy number gain.

Various embodiments provide for a method of predicting a cancer patient's response to a cancer treatment regimen comprising platinum or anthracycline, comprising: determining, in a cancer cell from the cancer patient, chromosome 15q26 copy number; and correlating the chromosome 15q26 copy number to a reference value, wherein when there is a chromosome 15q26 copy number gain, the patient is predicted to respond well to a cancer treatment comprising platinum or anthracycline, or wherein when there is not a chromosome 15q26 copy number gain or a chromosome 15q26 copy number loss, the patient is predicted respond poorly to a cancer treatment comprising platinum or anthracycline.

In various embodiments, the reference value is chromosome 15 centromere copy number.

Various embodiments provide for the use of platinum comprising cancer therapy for treating a cancer patient that has been determined to have a tumor comprising cancer cells wherein a chromosome 15q26 copy gain is detected compared to a reference value. In various embodiments, cancer patient is known to be or is determined to be negative for BRCA1 and/or BRCA2 mutations. The determination can be made before, concurrently with, or after the analysis for BLM and FANCI expression. In various embodiments, the cancer patient is known to not or is determined to not express detectable quantities of estrogen receptor (ER), progesterone receptor (PgR) and HER2 receptor. In various embodiments, the reference value is chromosome 15 centromere copy number.

Systems, Computers, Kits and Uses

Various embodiments of the present invention provide for a system for determining responsiveness of a cancer cell to platinum-comprising therapy from a cancer cell of a cancer patient, comprising: a sample analyzer configured to produce a signal for the mRNA from each one of BLM and FANCI from a cancer cell sample of a cancer patient; and a computer sub-system programmed to calculate, based on the mRNA whether the signal is greater or not than a reference value.

In various embodiments, said computer sub-system is programmed to compare the mRNA to determine a likelihood of responsiveness of said cancer cell to platinum-comprising cancer therapy based on an algorithm that classifies the patient as likely to respond to a platinum-comprising therapy if the BLM and FANCI expression is increased and as unlikely to respond to the platinum-comprising therapy if the BLM and FANCI expression is not increased; or a likelihood of responsiveness of said cancer cell to anthracycline-comprising cancer therapy based on an algorithm that classifies the patient as likely to respond to a anthracycline-comprising therapy if the BLM and FANCI expression is increased and as unlikely to respond to the anthracycline-comprising therapy if the BLM and FANCI expression is not increased.

Various embodiments of the present invention provide for a system for determining responsiveness of a cancer cell to platinum-comprising therapy from a cancer cell of a cancer patient, comprising: a sample analyzer configured to produce a signal for the protein from each one of BLM and FANCI from a cancer cell sample of a cancer patient; and a computer sub-system programmed to calculate, based on the protein whether the signal is greater or not than a reference value.

In various embodiments, said computer sub-system is programmed to compare the protein to determine a likelihood of responsiveness of said cancer cell to platinum-comprising cancer therapy based on an algorithm that classifies the patient as likely to respond to a platinum-comprising therapy if the BLM and FANCI expression is increased and as unlikely to respond to the platinum-comprising therapy if the BLM and FANCI expression is not increased; or a likelihood of responsiveness of said cancer cell to anthracycline-comprising cancer therapy based on an algorithm that classifies the patient as likely to respond to a anthracycline-comprising therapy if the BLM and FANCI expression is increased and as unlikely to respond to the anthracycline-comprising therapy if the BLM and FANCI expression is not increased.

Various embodiments of the present invention provide for a computer program product embodied in a computer readable medium that, when executing on a computer, performs steps comprising: detecting the BLM and FANCI expression in sample comprising a cancer cell from a cancer patient; and comparing the BLM and FANCI expression to a reference value.

Various embodiments of the present invention provide for a diagnostic kit for detecting a likelihood of a cancer patient to respond to platinum- or anthracycline-comprising comprising cancer therapy, comprising: no more than 10 probes comprising a combination of detectably labeled probes or primers for BLM and FANCI, and optionally for BRCA1 and/or at least one housekeeping gene; and the computer program product.

Various embodiments of the present invention provide for the use of a plurality of oligonucleotides comprising no more than 10 oligonucleotides capable of hybridizing to BLM and FANCI, and optionally to BRCA1 and/or at least one housekeeping gene, in a diagnostic kit for determining an increased likelihood that a cancer patient will respond to cancer treatment regimen comprising a platinum and/or anthracycline.

Various embodiments provide for a system for determining responsiveness of a cancer cell to platinum-comprising therapy from a cancer cell of a cancer patient, comprising: a sample analyzer configured to produce a signal for chromosome 15q26 copy number from a cancer cell sample of a cancer patient; and a computer sub-system programmed to calculate, based on the mRNA whether the signal is greater or not than a reference value.

In various embodiments, the computer sub-system is programmed to compare the mRNA to determine a likelihood of responsiveness of said cancer cell to platinum-comprising cancer therapy and/or or a anthracycline-comprising cancer therapy based on an algorithm that classifies the patient as likely to respond to a platinum-comprising therapy if there is a chromosome 15q26 copy number gain and as unlikely to respond to the platinum-comprising therapy if there is not a chromosome 15q26 copy number gain or if there is a chromosome 15q26 copy number loss. In various embodiments, the reference value is chromosome 15 centromere copy number.

Various embodiments of the present invention provide for a computer program product embodied in a computer readable medium that, when executing on a computer, performs steps comprising: detecting chromosome 15q26 copy number in sample comprising a cancer cell from a cancer patient; and comparing the chromosome 15q26 copy number to a reference value. In various embodiments, the reference value is chromosome 15 centromere copy number.

Various embodiments of the present invention provide for a diagnostic kit for detecting a likelihood of a cancer patient to respond to platinum- or anthracycline-comprising cancer therapy, comprising: no more than 10 probes comprising a combination of detectably labeled probes or primers for chromosome 15q26, and optionally for chromosome 15 centromere; and the computer program product of described herein.

Various embodiments of the present invention provide for the use of a plurality of oligonucleotides comprising no more than 10 oligonucleotides capable of hybridizing to chromosome 15q26, and optionally for chromosome 15 centromere, in a diagnostic kit for determining an increased likelihood that a cancer patient will respond to cancer treatment regimen comprising a platinum and/or anthracycline.

Reference Values

In various embodiments of the present invention, the reference value is based on BRCA1 gene expression in the cancer cell.

In various embodiments, the reference value for BLM expression or FANCI expression is BRCA1 expression.

In various embodiments, the reference value is BRCA1 expression, and the BLM and/or FANCI expression is increased by at least or about 10, 20, 30, 40, 50, 60, 70, 80, or 90% compared to BRCA1 expression.

In various embodiments, the reference value is BRCA1 expression, and the BLM and/or FANCI expression is increased by at least or about 1-fold, 1.1-fold, 1.2-fold, 1.3-fold, 1.4-fold, 1.5-fold, 1.6-fold, 1.7-fold, 1.8-fold, 1.9-fold, 2-fold, 2.1-fold 2.2-fold 2.3-fold 2.4-fold 2.5-fold, 2.6-fold, 2.7-fold, 2.8-fold, 2.9-fold, or 3-fold, 4-fold, 5-fold, 6-fold, 7-fold, 8-fold, 9-fold or 10-fold compared to BRCA1 expression. In certain embodiments, the reference value is BRCA1 expression, and the BLM and/or FANCI expression is increased by at least or about two-fold to about 7-fold compared to BRCA1 expression.

In various embodiments of the present invention, the reference value can be one or more housekeeping gene as described herein. In certain embodiments, one or more housekeeping gene as described herein, and the BLM and/or FANCI expression is increased by at least or about 10, 20, 30, 40, 50, 60, 70, 80, or 90% compared to the one or more housekeeping gene expression.

In certain embodiments, one or more housekeeping gene as described herein, and the BLM and/or FANCI expression is increased by at least or about 1-fold, 1.1-fold, 1.2-fold, 1.3-fold, 1.4-fold, 1.5-fold, 1.6-fold, 1.7-fold, 1.8-fold, 1.9-fold, 2-fold, 2.1-fold 2.2-fold 2.3-fold 2.4-fold 2.5-fold, 2.6-fold, 2.7-fold 2.8-fold 2.9-fold or 3-fold, 4-fold, 5-fold, 6-fold, 7-fold, 8-fold, 9-fold, 10-fold, 20-fold, 30-fold, 40-fold, 50-fold, 60-fold or higher compared to the one or more housekeeping gene expression depending on the level of the expression of the housekeeping gene in the cell.

In various embodiments, the housekeeping gene can be selected from the group consisting of beta-actin, GAPDH, RPLP0, GUS, TFRC and combinations thereof. (See e.g., Cronin et al., Clinical Chemistry 53:6, 1084-1091 (2007), and ONCOTYPE DX ASSAY®, herein incorporated by reference in its entirety.) Thus, in some embodiments, the house keeping gene is one of these genes, and in other embodiments, the housekeeping gene is a combination of 2, 3, 4, or all 5 of these genes. In particular embodiments, the housekeeping gene is RPLP0, also called 36b4.

In various embodiments, the house keeping gene can be selected from the genes listed in Table 1. Accordingly, in some embodiments, the housekeeping gene is one of the genes from Table 1, and in other embodiments, the housekeeping gene is a combination of any number or all of the genes from Table 1. (See e.g., Eisenberg and Levanon, Human housekeeping genes are compact. Trends in Genetics, Volume 19, Issue 7, 362-365, 1 Jul. 2003). Each gene name/description is followed by its geometric average expression level according to the data published by Su et al. Thus, based on our experimental data on the RPLP0 housekeeping gene as a reference gene, one of ordinary skill in the art can easily determine what the cut-off points for increased expression for any one of these genes is. For example, genes designated by asterisk are in popular use as reference in real-time PCR or quantitative PCR (qPCR), which is most often used in gene expression analysis.

In some aspects of all the embodiments on the invention, the assays, methods, kits, and systems incorporate qPCR as the gene expression analysis method to determine the amount compared to a reference value.

TABLE 1

Housekeeping Genes.

| Accession No. | Description |
|---|---|
| *NM_001101 | *Homo sapiens* actin, beta (ACTB), mRNA 6988 |
| *NM_000034 | *Homo sapiens* aldolase A,fructose-bisphosphate (ALDOA), mRNA 3425 |
| *NM_002046 | *Homo sapiens* glyceraldehyde-3-phosphate dehydrogenase (GAPD), mRNA 828 |
| *NM_000291 | *Homo sapiens* phosphoglycerate kinase 1 (PGK1), mRNA 2727 |
| *NM_005566 | *Homo sapiens* lactate dehydrogenase A (LDHA), mRNA 2105 |
| *NM_002954 | *Homo sapiens* ribosomal protein S27a (RPS27A), mRNA 4156 |
| *NM_000981 | *Homo sapiens* ribosomal protein L19 (RPL19), mRNA 6997 |
| *NM_000975 | *Homo sapiens* ribosomal protein L11 (RPL11), mRNA 6060 |
| *NM_007363 | *Homo sapiens* non-POU domain containing, octamer-binding (NONO), mRNA 1708 |
| *NM_004309 | *Homo sapiens* Rho GDP dissociation inhibitor (GDI) alpha (ARHGDIA), mRNA 1358 |
| *NM_000994 | *Homo sapiens* ribosomal protein L32 (RPL32), mRNA 9523 |
| *NM_022551 | *Homo sapiens* ribosomal protein S18 (RPS18), mRNA 11261 |
| *NM_007355 | *Homo sapiens* heat shock 90 kDa protein 1, beta (HSPCB), mRNA 4119 |
| NM_004515 | *Homo sapiens* interleukin enhancer binding factor 2, 45 kDa (ILF2), mRNA 1000 |
| NM_004651 | *Homo sapiens* ubiquitin specific protease 11 (USP11), mRNA 1950 |
| NM_004888 | *Homo sapiens* ATPase, H+ transporting, lysosomal 13 kDa, V1 subunit G isoform 1 (ATP6V1G1), mRNA 928 |
| NM_003334 | *Homo sapiens* ubiquitin-activating enzyme E1 (A1S9T and BN75 temperature sensitivity complementing) (UBE1), transcript variant 1, mRNA 1351 |
| NM_001320 | *Homo sapiens* casein kinase 2, beta polypeptide (CSNK2B), mRNA 1233 |
| NM_003915 | *Homo sapiens* copine I (CPNE1), transcript variant 3, mRNA 698 |
| NM_001250 | *Homo sapiens* tumor necrosis factor receptor superfamily, member 5 (TNFRSF5), transcript variant 1, mRNA 524 |
| NM_001904 | *Homo sapiens* catenin (cadherin-associated protein), beta 1, 88 kDa (CTNNB1), mRNA 1165 |
| NM_003753 | *Homo sapiens* eukaryotic translation initiation factor 3, subunit 7 zeta, 66/67 kDa (EIF3S7), mRNA 1363 |
| NM_004541 | *Homo sapiens* NADH dehydrogenase (ubiquinone) 1 alpha subcomplex, 1, 7.5 kDa (NDUFA1), nuclear gene encoding mitochondrial protein, mRNA 2307 |
| NM_001654 | *Homo sapiens* v-raf murine sarcoma 3611 viral oncogene homolog 1 (ARAF1), mRNA 846 |
| NM_002967 | *Homo sapiens* scaffold attachment factor B (SAFB), mRNA 545 |
| NM_001183 | *Homo sapiens* ATPase, H+ transporting, lysosomal interacting protein 1 (ATP6IP1), mRNA 1089 |
| NM_003526 | *Homo sapiens* H2B histone family, member L (H2BFL), mRNA 2232 |
| NM_004718 | *Homo sapiens* cytochrome c oxidase subunit VIIa polypeptide 2 like (COX7A2L), nuclear gene encoding mitochondrial protein, mRNA 1013 |
| NM_004436 | *Homo sapiens* endosulfine alpha (ENSA), mRNA 659 |
| NM_001207 | *Homo sapiens* basic transcription factor 3 (BTF3), mRNA 3348 |
| NM_004907 | *Homo sapiens* immediate early protein (ETR101), mRNA 1249 |
| NM_004889 | *Homo sapiens* ATP synthase, H+ transporting, mitochondrial F0 complex, subunit f, isoform 2 (ATP5J2), mRNA 1513 |
| NM_003769 | *Homo sapiens* splicing factor, arginine/serine-rich 9 (SFRS9), mRNA 1207 |
| NM_003910 | *Homo sapiens* maternal G10 transcript (G10), mRNA 696 |
| NM_000100 | *Homo sapiens* cystatin B (stefin B) (CSTB), mRNA 1422 |
| NM_004785 | *Homo sapiens* solute carrier family 9 (sodium/hydrogen exchanger), isoform 3 regulatory factor 2 (SLC9A3R2), mRNA 455 |
| NM_001120 | *Homo sapiens* tetracycline transporter-like protein (TETRAN), mRNA 935 |
| NM_000182 | *Homo sapiens* hydroxyacyl-Coenzyme A dehydrogenase/3-ketoacyl-Coenzyme A thiolase/enoyl-Coenzyme A hydratase (trifunctional protein), alpha subunit (HADHA), mRNA 609 |
| NM_003377 | *Homo sapiens* vascular endothelial growth factor B (VEGFB), mRNA 649 |
| NM_003576 | *Homo sapiens* serine/threonine kinase 24 (STE20 homolog, yeast) (STK24), mRNA 769 |
| NM_000918 | *Homo sapiens* procollagen-proline, 2-oxoglutarate 4-dioxygenase (proline 4-hydroxylase), beta polypeptide (protein disulfide isomerase; thyroid hormone binding protein p55) (P4HB), mRNA 2719 |
| NM_004584 | *Homo sapiens* RAD9 homolog (*S. pombe*) (RAD9), mRNA 860 |
| NM_004952 | *Homo sapiens* ephrin-A3 (EFNA3), mRNA 505 |
| NM_004308 | *Homo sapiens* Rho GTPase activating protein 1 (ARHGAP1), mRNA 893 |

TABLE 1-continued

Housekeeping Genes.

| Accession No. | Description |
|---|---|
| NM_003190 | *Homo sapiens* TAP binding protein (tapasin) (TAPBP), mRNA 1213 |
| NM_004640 | *Homo sapiens* HLA-B associated transcript 1 (BAT1), transcript variant 1, mRNA 1022 |
| NM_001064 | *Homo sapiens* transketolase (Wernicke-Korsakoff syndrome) (TKT), mRNA 1139 |
| NM_002117 | *Homo sapiens* major histocompatibility complex, class I, C (HLA-C), mRNA 4696 |
| NM_004161 | *Homo sapiens* RAB1A, member RAS oncogene family (RAB1A), mRNA 2163 |
| NM_003339 | *Homo sapiens* ubiquitin-conjugating enzyme E2D 2 (UBC4/5 homolog, yeast) (UBE2D2), mRNA 514 |
| NM_003969 | *Homo sapiens* ubiquitin-conjugating enzyme E2M (UBC12 homolog, yeast) (UBE2M), mRNA 1197 |
| NM_000516 | *Homo sapiens* GNAS complex locus (GNAS), transcript variant 1, mRNA 4358 |
| NM_002819 | *Homo sapiens* polypyrimidine tract binding protein 1 (PTBP1), transcript variant 1, mRNA 1138 |
| NM_001001 | *Homo sapiens* ribosomal protein L36a-like (RPL36AL), mRNA 1740 |
| NM_004649 | *Homo sapiens* chromosome 21 open reading frame 33 (C21orf33), mRNA 585 |
| NM_000175 | *Homo sapiens* glucose phosphate isomerase (GPI), mRNA 1633 |
| NM_001867 | *Homo sapiens* cytochrome c oxidase subunit VIIc (COX7C), nuclear gene encoding mitochondrial protein, mRNA 3004 |
| NM_001967 | *Homo sapiens* eukaryotic translation initiation factor 4A, isoform 2 (EIF4A2), mRNA 2935 |
| NM_001863 | *Homo sapiens* cytochrome c oxidase subunit VIb (COX6B), nuclear gene encoding mitochondrial protein, mRNA 1719 |
| NM_001997 | *Homo sapiens* Finkel-Biskis-Reilly murine sarcoma virus (FBR-MuSV) ubiquitously expressed (fox derived); ribosomal protein S30 (FAU), mRNA 3898 |
| NM_002088 | *Homo sapiens* glutamate receptor, ionotropic, kainate 5 (GRIK5), mRNA 535 |
| NM_001862 | *Homo sapiens* cytochrome c oxidase subunit Vb (COX5B), nuclear gene encoding mitochondrial protein, mRNA 1087 |
| NM_004255 | *Homo sapiens* cytochrome c oxidase subunit Va (COX5A), nuclear gene encoding mitochondrial protein, mRNA 853 |
| NM_001788 | *Homo sapiens* CDC10 cell division cycle 10 homolog (S. cerevisiae) (CDC10), mRNA 1340 |
| NM_004781 | *Homo sapiens* vesicle-associated membrane protein 3 (cellubrevin) (VAMP3), mRNA 684 |
| NM_003801 | *Homo sapiens* GPAA1P anchor attachment protein 1 homolog (yeast) (GPAA1), mRNA 776 |
| NM_004643 | *Homo sapiens* poly(A) binding protein, nuclear 1 (PABPN1), mRNA 502 |
| NM_001537 | *Homo sapiens* heat shock factor binding protein 1 (HSBP1), mRNA 874 |
| NM_003680 | *Homo sapiens* tyrosyl-tRNA synthetase (YARS), mRNA 535 |
| NM_003345 | *Homo sapiens* ubiquitin-conjugating enzyme E2I (UBC9 homolog, yeast) (UBE2I), mRNA 1283 |
| NM_002568 | *Homo sapiens* poly(A) binding protein, cytoplasmic 1 (PABPC1), mRNA 3199 |
| NM_001487 | *Homo sapiens* GCN5 general control of amino-acid synthesis 5-like 1 (yeast) (GCN5L1), mRNA 313 |
| NM_001861 | *Homo sapiens* cytochrome c oxidase subunit IV isoform 1 (COX4I1), nuclear gene encoding mitochondrial protein, mRNA 2738 |
| NM_004890 | *Homo sapiens* sperm associated antigen 7 (SPAG7), mRNA 618 |
| NM_002812 | *Homo sapiens* proteasome (prosome, macropain) 26S subunit, non-ATPase, 8 (PSMD8), mRNA 942 |
| NM_004926 | *Homo sapiens* zinc finger protein 36, C3H type-like 1 (ZFP36L1), mRNA 1168 |
| NM_002539 | *Homo sapiens* ornithine decarboxylase 1 (ODC1), mRNA 1361 |
| NM_000979 | *Homo sapiens* ribosomal protein L18 (RPL18), mRNA 4417 |
| NM_000977 | *Homo sapiens* ribosomal protein L13 (RPL13), transcript variant 1, mRNA 6407 |
| NM_001015 | *Homo sapiens* ribosomal protein S11 (RPS11), mRNA 7614 |
| NM_001760 | *Homo sapiens* cyclin D3 (CCND3), mRNA 676 |
| NM_003973 | *Homo sapiens* ribosomal protein L14 (RPL14), mRNA 3135 |
| NM_002815 | *Homo sapiens* proteasome (prosome, macropain) 26S subunit, non-ATPase, 11 (PSMD11), mRNA 536 |
| NM_000367 | *Homo sapiens* thiopurine S-methyltransferase (TPMT), mRNA 1574 |
| NM_000973 | *Homo sapiens* ribosomal protein L8 (RPL8), transcript variant 1, mRNA 8138 |
| NM_004689 | *Homo sapiens* metastasis associated 1 (MTA1), mRNA 506 |

TABLE 1-continued

Housekeeping Genes.

| Accession No. | Description |
|---|---|
| NM_001848 | *Homo sapiens* collagen, type VI, alpha 1 (COL6A1), mRNA 757 |
| NM_004068 | *Homo sapiens* adaptor-related protein complex 2, mu 1 subunit (AP2M1), mRNA 2188 |
| NM_001687 | *Homo sapiens* ATP synthase, H+ transporting, mitochondrial F1 complex, delta subunit (ATP5D), mRNA 1167 |
| NM_004197 | *Homo sapiens* serine/threonine kinase 19 (STK19), transcript variant 1, mRNA 574 |
| NM_001028 | *Homo sapiens* ribosomal protein S25 (RPS25), mRNA 4683 |
| NM_001022 | *Homo sapiens* ribosomal protein S19 (RPS19), mRNA 6683 |
| NM_004759 | *Homo sapiens* mitogen-activated protein kinase-activated protein kinase 2 (MAPKAPK2), transcript variant 1, mRNA 641 |
| NM_001623 | *Homo sapiens* allograft inflammatory factor 1 (AIF1), transcript variant 3, mRNA 497 |
| NM_004894 | *Homo sapiens* chromosome 14 open reading frame 2 (C14orf2), mRNA 704 |
| NM_002375 | *Homo sapiens* microtubule-associated protein 4 (MAP4), transcript variant 1, mRNA 717 |
| NM_001013 | *Homo sapiens* ribosomal protein S9 (RPS9), mRNA 6868 |
| NM_003779 | *Homo sapiens* UDP-Gal:betaGlcNAc beta 1,4-galactosyltransferase, polypeptide 3 (B4GALT3), mRNA 565 |
| NM_001296 | *Homo sapiens* chemokine binding protein 2 (CCBP2), mRNA 394 |
| NM_001009 | *Homo sapiens* ribosomal protein S5 (RPS5), mRNA 6739 |
| NM_003021 | *Homo sapiens* small glutamine-rich tetratricopeptide repeat (TPR)-containing (SGT), mRNA 488 |
| NM_004285 | *Homo sapiens* hexose-6-phosphate dehydrogenase (glucose 1-dehydrogenase) (H6PD), mRNA 646 |
| NM_004142 | *Homo sapiens* matrix metalloproteinase-like 1 (MMPL1), mRNA 695 |
| NM_001950 | *Homo sapiens* E2F transcription factor 4, p107/p130-binding (E2F4), mRNA 956 |
| NM_003815 | *Homo sapiens* a disintegrin and metalloproteinase domain 15 (metargidin) (ADAM15), mRNA 771 |
| NM_001119 | *Homo sapiens* adducin 1 (alpha) (ADD1), transcript variant 1, mRNA 1356 |
| NM_001111 | *Homo sapiens* adenosine deaminase, RNA-specific (ADAR), transcript variant ADAR-a, mRNA 1036 |
| NM_003466 | *Homo sapiens* paired box gene 8 (PAX8), transcript variant PAX8A, mRNA 901 |
| NM_001155 | *Homo sapiens* annexin A6 (ANXA6), transcript variant 1, mRNA 718 |
| NM_003465 | *Homo sapiens* chitinase 1 (chitotriosidase) (CHIT1), mRNA 561 |
| NM_003186 | *Homo sapiens* transgelin (TAGLN), mRNA 1209 |
| NM_000802 | *Homo sapiens* folate receptor 1 (adult) (FOLR1), transcript variant 2, mRNA 514 |
| NM_004924 | *Homo sapiens* actinin, alpha 4 (ACTN4), mRNA 1187 |
| NM_002931 | *Homo sapiens* ring finger protein 1 (RING1), mRNA 576 |
| NM_000020 | *Homo sapiens* activin A receptor type II-like 1 (ACVRL1), mRNA 849 |
| NM_001785 | *Homo sapiens* cytidine deaminase (CDA), mRNA 391 |
| NM_004339 | *Homo sapiens* pituitary tumor-transforming 1 interacting protein (PTTG1IP), mRNA 1200 |
| NM_003860 | *Homo sapiens* Breakpoint cluster region protein, uterine leiomyoma, 1; barrier to autointegration factor (BCRP1), mRNA 1303 |
| NM_000214 | *Homo sapiens* jagged 1 (Alagille syndrome) (JAG1), mRNA 536 |
| NM_002167 | *Homo sapiens* inhibitor of DNA binding 3, dominant negative helix-loop-helix protein (ID3), mRNA 1192 |
| NM_001664 | *Homo sapiens* ras homolog gene family, member A (ARHA), mRNA 4050 |
| NM_003166 | *Homo sapiens* sulfotransferase family, cytosolic, 1A, phenol-preferring, member 3 (SULT1A3), mRNA 461 |
| NM_001746 | *Homo sapiens* calnexin (CANX), mRNA 1923 |
| NM_001662 | *Homo sapiens* ADP-ribosylation factor 5 (ARF5), mRNA 724 |
| NM_001660 | *Homo sapiens* ADP-ribosylation factor 4 (ARF4), mRNA 1014 |
| NM_001658 | *Homo sapiens* ADP-ribosylation factor 1 (ARF1), mRNA 2195 |
| NM_003313 | *Homo sapiens* tissue specific transplantation antigen P35B (TSTA3), mRNA 440 |
| NM_001494 | *Homo sapiens* GDP dissociation inhibitor 2 (GDI2), mRNA 1352 |
| NM_003145 | *Homo sapiens* signal sequence receptor, beta (translocon-associated protein beta) (SSR2), mRNA 1265 |
| NM_001619 | *Homo sapiens* adrenergic, beta, receptor kinase 1 (ADRBK1), mRNA 695 |
| NM_001420 | *Homo sapiens* ELAV (embryonic lethal, abnormal vision, *Drosophila*)-like 3 (Hu antigen C) (ELAVL3), mRNA 1070 |
| NM_004930 | *Homo sapiens* capping protein (actin filament) muscle Z-line, beta (CAPZB), mRNA 1183 |
| NM_004596 | *Homo sapiens* small nuclear ribonucleoprotein polypeptide A (SNRPA), mRNA 734 |

TABLE 1-continued

Housekeeping Genes.

| Accession No. | Description |
|---|---|
| NM_004168 | *Homo sapiens* succinate dehydrogenase complex, subunit A, flavoprotein (Fp) (SDHA), nuclear gene encoding mitochondrial protein, mRNA 1106 |
| NM_004156 | *Homo sapiens* protein phosphatase 2 (formerly 2A), catalytic subunit, beta isoform (PPP2CB), mRNA 1195 |
| NM_004910 | *Homo sapiens* phosphatidylinositol transfer protein, membrane-associated (PITPNM), mRNA 869 |
| NM_004517 | *Homo sapiens* integrin-linked kinase (ILK), mRNA 654 |
| NM_004494 | *Homo sapiens* hepatoma-derived growth factor (high-mobility group protein 1-like) (HDGF), mRNA 1385 |
| NM_004121 | *Homo sapiens* gamma-glutamyltransferase-like activity 1 (GGTLA1), mRNA 412 |
| NM_004404 | *Homo sapiens* neural precursor cell expressed, developmentally down-regulated 5 (NEDD5), mRNA 1571 |
| NM_004394 | *Homo sapiens* death-associated protein (DAP), mRNA 623 |
| NM_004383 | *Homo sapiens* c-src tyrosine kinase (CSK), mRNA 899 |
| NM_004074 | *Homo sapiens* cytochrome c oxidase subunit VIII (COX8), nuclear gene encoding mitochondrial protein, mRNA 3188 |
| NM_004039 | *Homo sapiens* annexin A2 (ANXA2), mRNA 2417 |
| NM_001053 | *Homo sapiens* somatostatin receptor 5 (SSTR5), mRNA 423 |
| NM_001328 | *Homo sapiens* C-terminal binding protein 1 (CTBP1), mRNA 798 |
| NM_001273 | *Homo sapiens* chromodomain helicase DNA binding protein 4 (CHD4), mRNA 775 |
| NM_003430 | *Homo sapiens* zinc finger protein 91 (HPF7, HTF10) (ZNF91), mRNA 716 |
| NM_003314 | *Homo sapiens* tetratricopeptide repeat domain 1 (TTC1), mRNA 651 |
| NM_003217 | *Homo sapiens* testis enhanced gene transcript (TEGT), mRNA 1766 |
| NM_003132 | *Homo sapiens* spermidine synthase (SRM), mRNA 1093 |
| NM_000199 | *Homo sapiens* N-sulfoglucosamine sulfohydrolase (sulfamidase) (SGSH), mRNA 565 |
| NM_002818 | *Homo sapiens* proteasome (prosome, macropain) activator subunit 2 (PA28 beta) (PSME2), mRNA 697 |
| NM_002733 | *Homo sapiens* protein kinase, AMP-activated, gamma 1 non-catalytic subunit (PRKAG1), mRNA 497 |
| NM_002631 | *Homo sapiens* phosphogluconate dehydrogenase (PGD), mRNA 1009 |
| NM_002574 | *Homo sapiens* peroxiredoxin 1 (PRDX1), mRNA 2241 |
| NM_002512 | *Homo sapiens* non-metastatic cells 2, protein (NM23B) expressed in (NME2), nuclear gene encoding mitochondrial protein, mRNA 2553 |
| NM_002455 | *Homo sapiens* metaxin 1 (MTX1), mRNA 845 |
| NM_002444 | *Homo sapiens* moesin (MSN), mRNA 1798 |
| NM_000529 | *Homo sapiens* melanocortin 2 receptor (adrenocorticotropic hormone) (MC2R), mRNA 420 |
| NM_003573 | *Homo sapiens* latent transforming growth factor beta binding protein 4 (LTBP4), mRNA 740 |
| NM_002315 | *Homo sapiens* LIM domain only 1 (rhombotin 1) (LMO1), mRNA 469 |
| NM_000884 | *Homo sapiens* IMP (inosine monophosphate) dehydrogenase 2 (IMPDH2), mRNA 1288 |
| NM_003641 | *Homo sapiens* interferon induced transmembrane protein 1 (9-27) (IFITM1), mRNA 4898 |
| NM_000841 | *Homo sapiens* glutamate receptor, metabotropic 4 (GRM4), mRNA 1369 |
| NM_002070 | *Homo sapiens* guanine nucleotide binding protein (G protein), alpha inhibiting activity polypeptide 2 (GNAI2), mRNA 1877 |
| NM_001493 | *Homo sapiens* GDP dissociation inhibitor 1 (GDI1), mRNA 1387 |
| NM_002048 | *Homo sapiens* growth arrest-specific 1 (GAS1), mRNA 940 |
| NM_002032 | *Homo sapiens* ferritin, heavy polypeptide 1 (FTH1), mRNA 2616 |
| NM_001418 | *Homo sapiens* eukaryotic translation initiation factor 4 gamma, 2 (EIF4G2), mRNA 3646 |
| NM_001350 | *Homo sapiens* death-associated protein 6 (DAXX), mRNA 510 |
| NM_001843 | *Homo sapiens* contactin 1 (CNTN1), mRNA 535 |
| NM_001728 | *Homo sapiens* basigin (BSG), mRNA 1508 |
| NM_001667 | *Homo sapiens* ADP-ribosylation factor-like 2 (ARL2), mRNA 965 |
| NM_001659 | *Homo sapiens* ADP-ribosylation factor 3 (ARF3), mRNA 1327 |
| NM_003746 | *Homo sapiens* dynein, cytoplasmic, light polypeptide 1 (DNCL1), mRNA 2758 |
| NM_002127 | *Homo sapiens* HLA-G histocompatibility antigen, class I, G (HLA-G), mRNA 1090 |
| NM_004712 | *Homo sapiens* hepatocyte growth factor-regulated tyrosine kinase substrate (HGS), mRNA 505 |

TABLE 1-continued

Housekeeping Genes.

| Accession No. | Description |
|---|---|
| NM_003475 | *Homo sapiens* chromosome 11 open reading frame 13 (C11orf13), mRNA 413 |
| NM_004046 | *Homo sapiens* ATP synthase, H+ transporting, mitochondrial F1 complex, alpha subunit, isoform 1, cardiac muscle (ATP5A1), mRNA 1348 |
| NM_001894 | *Homo sapiens* casein kinase 1, epsilon (CSNK1E), transcript variant 2, mRNA 613 |
| NM_003795 | *Homo sapiens* sorting nexin 3 (SNX3), transcript variant 1, mRNA 1426 |
| NM_001909 | *Homo sapiens* cathepsin D (lysosomal aspartyl protease) (CTSD), mRNA 1512 |
| NM_002792 | *Homo sapiens* proteasome (prosome, macropain) subunit, alpha type, 7 (PSMA7), transcript variant 1, mRNA 728 |
| NM_002799 | *Homo sapiens* proteasome (prosome, macropain) subunit, beta type, 7 (PSMB7), mRNA 545 |
| NM_002300 | *Homo sapiens* lactate dehydrogenase B (LDHB), mRNA 4144 |
| NM_004176 | *Homo sapiens* sterol regulatory element binding transcription factor 1 (SREBF1), mRNA 632 |
| NM_002796 | *Homo sapiens* proteasome (prosome, macropain) subunit, beta type, 4 (PSMB4), mRNA 1229 |
| NM_002794 | *Homo sapiens* proteasome (prosome, macropain) subunit, beta type, 2 (PSMB2), mRNA 1304 |
| NM_002793 | *Homo sapiens* proteasome (prosome, macropain) subunit, beta type, 1 (PSMB1), mRNA 2084 |
| NM_002473 | *Homo sapiens* myosin, heavy polypeptide 9, non-muscle (MYH9), mRNA 1381 |
| NM_001810 | *Homo sapiens* centromere protein B, 80 kDa (CENPB), mRNA 532 |
| NM_002624 | *Homo sapiens* prefoldin 5 (PFDN5), transcript variant 1, mRNA 1718 |
| NM_004710 | *Homo sapiens* synaptogyrin 2 (SYNGR2), mRNA 1414 |
| NM_001127 | *Homo sapiens* adaptor-related protein complex 1, beta 1 subunit (AP1B1), transcript variant 1, mRNA 873 |
| NM_002107 | *Homo sapiens* H3 histone, family 3A (H3F3A), mRNA 9328 |
| NM_003899 | *Homo sapiens* Rho guanine nucleotide exchange factor (GEF) 7 (ARHGEF7), transcript variant 1, mRNA 558 |
| NM_003406 | *Homo sapiens* tyrosine 3-monooxygenase/tryptophan 5-monooxygenase activation protein, zeta polypeptide (YWHAZ), transcript variant 1, mRNA 2008 |
| NM_002419 | *Homo sapiens* mitogen-activated protein kinase kinase kinase 11 (MAP3K11), mRNA 535 |
| NM_001130 | *Homo sapiens* amino-terminal enhancer of split (AES), mRNA 2395 |
| NM_003379 | *Homo sapiens* villin 2 (ezrin) (VIL2), mRNA 1356 |
| NM_002636 | *Homo sapiens* PHD finger protein 1 (PHF1), transcript variant 1, mRNA 640 |
| NM_002622 | *Homo sapiens* prefoldin 1 (PFDN1), mRNA 658 |
| NM_001823 | *Homo sapiens* creatine kinase, brain (CKB), mRNA 1407 |
| NM_003405 | *Homo sapiens* tyrosine 3-monooxygenase/tryptophan 5-monooxygenase activation protein, eta polypeptide (YWHAH), mRNA 2195 |
| NM_002939 | *Homo sapiens* ribonuclease/angiogenin inhibitor (RNH), mRNA 726 |
| NM_003562 | *Homo sapiens* solute carrier family 25 (mitochondrial carrier; oxoglutarate carrier), member 11 (SLC25A11), mRNA 517 |
| NM_001916 | *Homo sapiens* cytochrome c-1 (CYC1), mRNA 895 |
| NM_002823 | *Homo sapiens* prothymosin, alpha (gene sequence 28) (PTMA), mRNA 3723 |
| NM_003096 | *Homo sapiens* small nuclear ribonucleoprotein polypeptide G (SNRPG), mRNA 687 |
| NM_003321 | *Homo sapiens* Tu translation elongation factor, mitochondrial (TUFM), mRNA 1543 |
| NM_003404 | *Homo sapiens* tyrosine 3-monooxygenase/tryptophan 5-monooxygenase activation protein, beta polypeptide (YWHAB), transcript variant 1, mRNA 1144 |
| NM_002946 | *Homo sapiens* replication protein A2, 32 kDa (RPA2), mRNA 537 |
| NM_004356 | *Homo sapiens* CD81 antigen (target of antiproliferative antibody 1) (CD81), mRNA 3638 |
| NM_001743 | *Homo sapiens* calmodulin 2 (phosphorylase kinase, delta) (CALM2), mRNA 4675 |
| NM_004231 | *Homo sapiens* ATPase, H+ transporting, lysosomal 14 kDa, V1 subunit F (ATP6V1F), mRNA 997 |
| NM_004893 | *Homo sapiens* H2A histone family, member Y (H2AFY), transcript variant 2, mRNA 788 |
| NM_004146 | *Homo sapiens* NADH dehydrogenase (ubiquinone) 1 beta subcomplex, 7, 18 kDa (NDUFB7), mRNA 967 |
| NM_002128 | *Homo sapiens* high-mobility group box 1 (HMGB1), mRNA 1295 |

TABLE 1-continued

Housekeeping Genes.

| Accession No. | Description |
| --- | --- |
| NM_002002 | *Homo sapiens* Fc fragment of IgE, low affinity II, receptor for (CD23A) (FCER2), mRNA 969 |
| NM_000858 | *Homo sapiens* guanylate kinase 1 (GUK1), mRNA 1166 |
| NM_001469 | *Homo sapiens* thyroid autoantigen 70 kDa (Ku antigen) (G22P1), mRNA 1684 |
| NM_003766 | *Homo sapiens* beclin 1 (coiled-coil, myosin-like BCL2 interacting protein) (BECN1), mRNA 948 |
| NM_003906 | *Homo sapiens* MCM3 minichromosome maintenance deficient 3 (*S. cerevisiae*) associated protein (MCM3AP), mRNA 430 |
| NM_000757 | *Homo sapiens* colony stimulating factor 1 (macrophage) (CSF1), mRNA 797 |
| NM_002149 | *Homo sapiens* hippocalcin-like 1 (HPCAL1), transcript variant 1, mRNA 1026 |
| NM_001694 | *Homo sapiens* ATPase, H+ transporting, lysosomal 16 kDa, V0 subunit c (ATP6V0C), mRNA 2105 |
| NM_004047 | *Homo sapiens* ATPase, H+ transporting, lysosomal 21 kDa, V0 subunit c" (ATP6V0B), mRNA 1212 |
| NM_001696 | *Homo sapiens* ATPase, H+ transporting, lysosomal 31 kDa, V1 subunit E isoform 1 (ATP6V1E1), mRNA 784 |
| NM_001865 | *Homo sapiens* cytochrome c oxidase subunit VIIa polypeptide 2 (liver) (COX7A2), nuclear gene encoding mitochondrial protein, mRNA 1818 |
| NM_004373 | *Homo sapiens* cytochrome c oxidase subunit VIa polypeptide 1 (COX6A1), nuclear gene encoding mitochondrial protein, mRNA 5529 |
| NM_000801 | *Homo sapiens* FK506 binding protein 1A, 12 kDa (FKBP1A), transcript variant 12B, mRNA 4273 |
| NM_000992 | *Homo sapiens* ribosomal protein L29 (RPL29), mRNA 6060 |
| NM_000988 | *Homo sapiens* ribosomal protein L27 (RPL27), mRNA 6101 |
| NM_001004 | *Homo sapiens* ribosomal protein, large P2 (RPLP2), mRNA 5924 |
| NM_001003 | *Homo sapiens* ribosomal protein, large, P1 (RPLP1), mRNA 10300 |
| NM_000405 | *Homo sapiens* GM2 ganglioside activator protein (GM2A), mRNA 1250 |
| NM_000967 | *Homo sapiens* ribosomal protein L3 (RPL3), mRNA 7416 |
| NM_001428 | *Homo sapiens* enolase 1, (alpha) (ENO1), mRNA 3668 |
| NM_000999 | *Homo sapiens* ribosomal protein L38 (RPL38), mRNA 8302 |
| NM_000997 | *Homo sapiens* ribosomal protein L37 (RPL37), mRNA 6689 |
| NM_000995 | *Homo sapiens* ribosomal protein L34 (RPL34), transcript variant 1, mRNA 5424 |
| NM_002948 | *Homo sapiens* ribosomal protein L15 (RPL15), mRNA 5450 |
| NM_002952 | *Homo sapiens* ribosomal protein S2 (RPS2), mRNA 8825 |
| NM_001026 | *Homo sapiens* ribosomal protein S24 (RPS24), transcript variant 2, mRNA 5701 |
| NM_001020 | *Homo sapiens* ribosomal protein S16 (RPS16), mRNA 7477 |
| NM_001018 | *Homo sapiens* ribosomal protein S15 (RPS15), mRNA 6261 |
| NM_001017 | *Homo sapiens* ribosomal protein S13 (RPS13), mRNA 5430 |
| NM_000969 | *Homo sapiens* ribosomal protein L5 (RPL5), mRNA 4653 |
| NM_000985 | *Homo sapiens* ribosomal protein L17 (RPL17), mRNA 4369 |
| NM_000937 | *Homo sapiens* polymerase (RNA) II (DNA directed) polypeptide A, 220 kDa (POLR2A), mRNA 753 |
| NM_001016 | *Homo sapiens* ribosomal protein S12 (RPS12), mRNA 8265 |
| NM_002140 | *Homo sapiens* heterogeneous nuclear ribonucleoprotein K (HNRPK), transcript variant 1, mRNA 2429 |
| NM_002138 | *Homo sapiens* heterogeneous nuclear ribonucleoprotein D (AU-rich element RNA binding protein 1, 37 kDa) (HNRPD), transcript variant 3, mRNA 1157 |
| NM_004499 | *Homo sapiens* heterogeneous nuclear ribonucleoprotein A/B (HNRPAB), transcript variant 2, mRNA 654 |
| NM_001014 | *Homo sapiens* ribosomal protein S10 (RPS10), mRNA 8074 |
| NM_002383 | *Homo sapiens* MYC-associated zinc finger protein (purine-binding transcription factor) (MAZ), mRNA 2580 |
| NM_002467 | *Homo sapiens* v-myc myelocytomatosis viral oncogene homolog (avian) (MYC), mRNA 537 |
| NM_001436 | *Homo sapiens* fibrillarin (FBL), mRNA 1408 |
| NM_004069 | *Homo sapiens* adaptor-related protein complex 2, sigma 1 subunit (AP2S1), transcript variant AP17, mRNA 979 |
| NM_001614 | *Homo sapiens* actin, gamma 1 (ACTG1), mRNA 6560 |
| NM_002355 | *Homo sapiens* mannose-6-phosphate receptor (cation dependent) (M6PR), mRNA 388 |
| NM_004597 | *Homo sapiens* small nuclear ribonucleoprotein D2 polypeptide 16.5 kDa (SNRPD2), mRNA 1136 |
| NM_002308 | *Homo sapiens* lectin, galactoside-binding, soluble, 9 (galectin 9) (LGALS9), transcript variant short, mRNA 888 |

TABLE 1-continued

Housekeeping Genes.

| Accession No. | Description |
|---|---|
| NM_000398 | *Homo sapiens* diaphorase (NADH) (cytochrome b-5 reductase) (DIA1), nuclear gene encoding mitochondrial protein, transcript variant M, mRNA 2190 |
| NM_000754 | *Homo sapiens* catechol-O-methyltransferase (COMT), transcript variant MB-COMT, mRNA 845 |
| NM_002406 | *Homo sapiens* mannosyl (alpha-1,3-)-glycoprotein beta-1,2-N-acetylglucosaminyltransferase (MGAT1), mRNA 893 |
| NM_003752 | *Homo sapiens* eukaryotic translation initiation factor 3, subunit 8, 110 kDa (EIF3S8), mRNA 1871 |
| NM_001355 | *Homo sapiens* D-dopachrome tautomerase (DDT), mRNA 631 |
| NM_004960 | *Homo sapiens* fusion, derived from t(12;16) malignant liposarcoma (FUS), mRNA 1019 |
| NM_004729 | *Homo sapiens* Ac-like transposable element (ALTE), mRNA 963 |
| NM_004587 | *Homo sapiens* ribosome binding protein 1 homolog 180 kDa (dog) (RRBP1), mRNA 658 |
| NM_004552 | *Homo sapiens* NADH dehydrogenase (ubiquinone) Fe-S protein 5, 15 kDa (NADH-coenzyme Q reductase) (NDUFS5), mRNA 936 |
| NM_004450 | *Homo sapiens* enhancer of rudimentary homolog (*Drosophila*) (ERH), mRNA 1028 |
| NM_004048 | *Homo sapiens* beta-2-microglobulin (B2M), mRNA 4992 |
| NM_000239 | *Homo sapiens* lysozyme (renal amyloidosis) (LYZ), mRNA 796 |
| NM_000269 | *Homo sapiens* non-metastatic cells 1, protein (NM23A) expressed in (NME1), mRNA 887 |
| NM_000431 | *Homo sapiens* mevalonate kinase (mevalonic aciduria) (MVK), mRNA 753 |
| NM_001247 | *Homo sapiens* ectonucleoside triphosphate diphosphohydrolase 6 (putative function) (ENTPD6), mRNA 495 |
| NM_003365 | *Homo sapiens* ubiquinol-cytochrome c reductase core protein I (UQCRC1), mRNA 1026 |
| NM_003329 | *Homo sapiens* thioredoxin (TXN), mRNA 1002 |
| NM_001069 | *Homo sapiens* tubulin, beta polypeptide (TUBB), mRNA 1013 |
| NM_000356 | *Homo sapiens* Treacher Collins-Franceschetti syndrome 1 (TCOF1), mRNA 673 |
| NM_003134 | *Homo sapiens* signal recognition particle 14 kDa (homologous Alu RNA binding protein) (SRP14), mRNA 2911 |
| NM_003131 | *Homo sapiens* serum response factor (c-fos serum response element-binding transcription factor) (SRF), mRNA 664 |
| NM_000454 | *Homo sapiens* superoxide dismutase 1, soluble (amyotrophic lateral sclerosis 1 (adult)) (SOD1), mRNA 1739 |
| NM_003091 | *Homo sapiens* small nuclear ribonucleoprotein polypeptides B and B1 (SNRPB), mRNA 1609 |
| NM_003089 | *Homo sapiens* small nuclear ribonucleoprotein 70 kDa polypeptide (RNP antigen) (SNRP70), mRNA 1672 |
| NM_003016 | *Homo sapiens* splicing factor, arginine/serine-rich 2 (SFRS2), mRNA 1476 |
| NM_003952 | *Homo sapiens* ribosomal protein S6 kinase, 70 kDa, polypeptide 2 (RPS6KB2), mRNA 476 |
| NM_002950 | *Homo sapiens* ribophorin I (RPN1), mRNA 495 |
| NM_002743 | *Homo sapiens* protein kinase C substrate 80K-H (PRKCSH), mRNA 691 |
| NM_002686 | *Homo sapiens* phenylethanolamine N-methyltransferase (PNMT), mRNA 501 |
| NM_002654 | *Homo sapiens* pyruvate kinase, muscle (PKM2), mRNA 2474 |
| NM_002648 | *Homo sapiens* pim-1 oncogene (PIM1), mRNA 1052 |
| NM_002635 | *Homo sapiens* solute carrier family 25 (mitochondrial carrier; phosphate carrier), member 3 (SLC25A3), nuclear gene encoding mitochondrial protein, transcript variant 1b, mRNA 2310 |
| NM_002494 | *Homo sapiens* NADH dehydrogenase (ubiquinone) 1, subcomplex unknown, 1, 6 kDa (NDUF C1), mRNA 2247 |
| NM_002488 | *Homo sapiens* NADH dehydrogenase (ubiquinone) 1 alpha subcomplex, 2, 8 kDa (NDUFA2), mRNA 689 |
| NM_002434 | *Homo sapiens* N-methylpurine-DNA glycosylase (MPG), mRNA 1808 |
| NM_002415 | *Homo sapiens* macrophage migration inhibitory factor (glycosylation-inhibiting factor) (MIF), mRNA 3774 |
| NM_002227 | *Homo sapiens* Janus kinase 1 (a protein tyrosine kinase) (JAK1), mRNA 990 |
| NM_001536 | *Homo sapiens* HMT1 hnRNP methyltransferase-like 2 (*S. cerevisiae*) (HRMT1L2), mRNA 832 |
| NM_000183 | *Homo sapiens* hydroxyacyl-Coenzyme A dehydrogenase/3-ketoacyl-Coenzyme A thiolase/enoyl-Coenzyme A hydratase (trifunctional protein), beta subunit (HADHB), mRNA 1087 |
| NM_002085 | *Homo sapiens* glutathione peroxidase 4 (phospholipid hydroperoxidase) (GPX4), mRNA 1279 |
| NM_001502 | *Homo sapiens* glycoprotein 2 (zymogen granule membrane) (GP2), mRNA 572 |

TABLE 1-continued

Housekeeping Genes.

| Accession No. | Description |
| --- | --- |
| NM_002080 | *Homo sapiens* glutamic-oxaloacetic transaminase 2, mitochondrial (aspartate aminotransferase 2) (GOT2), nuclear gene encoding mitochondrial protein, mRNA 1000 |
| NM_001440 | *Homo sapiens* exostoses (multiple)-like 3 (EXTL3), mRNA 592 |
| NM_003754 | *Homo sapiens* eukaryotic translation initiation factor 3, subunit 5 epsilon, 47 kDa (EIF3S5), mRNA 1585 |
| NM_003755 | *Homo sapiens* eukaryotic translation initiation factor 3, subunit 4 delta, 44 kDa (EIF3S4), mRNA 1085 |
| NM_003757 | *Homo sapiens* eukaryotic translation initiation factor 3, subunit 2 beta, 36 kDa (EIF3S2), mRNA 622 |
| NM_001360 | *Homo sapiens* 7-dehydrocholesterol reductase (DHCR7), mRNA 653 |
| NM_001344 | *Homo sapiens* defender against cell death 1 (DAD1), mRNA 812 |
| NM_001914 | *Homo sapiens* cytochrome b-5 (CYB5), nuclear gene encoding mitochondrial protein, mRNA 667 |
| NM_001834 | *Homo sapiens* clathrin, light polypeptide (Lcb) (CLTB), transcript variant nonbrain, mRNA 447 |
| NM_001833 | *Homo sapiens* clathrin, light polypeptide (Lca) (CLTA), transcript variant nonbrain, mRNA 1315 |
| NM_001281 | *Homo sapiens* cytoskeleton-associated protein 1 (CKAP1), mRNA 1066 |
| NM_001749 | *Homo sapiens* calpain, small subunit 1 (CAPNS1), mRNA 1308 |
| NM_001697 | *Homo sapiens* ATP synthase, H+ transporting, mitochondrial F1 complex, 0 subunit (oligomycin sensitivity conferring protein) (ATP5O), mRNA 1155 |
| NM_001689 | *Homo sapiens* ATP synthase, H+ transporting, mitochondrial F0 complex, subunit c (subunit 9) isoform 3 (ATP5G3), mRNA 1152 |
| NM_001675 | *Homo sapiens* activating transcription factor 4 (tax-responsive enhancer element B67) (ATF4), mRNA 1392 |
| NM_001642 | *Homo sapiens* amyloid beta (A4) precursor-like protein 2 (APLP2), mRNA 1341 |
| NM_014724 | *Homo sapiens* zinc finger protein 305 (ZNF305), mRNA 719 |
| NM_005494 | *Homo sapiens* DnaJ (Hsp40) homolog, subfamily B, member 6 (DNAJB6), transcript variant 2, mRNA 923 |
| NM_006597 | *Homo sapiens* heat shock 70 kDa protein 8 (HSPA8), transcript variant 1, mRNA 1650 |
| NM_006623 | *Homo sapiens* phosphoglycerate dehydrogenase (PHGDH), mRNA 888 |
| NM_015646 | *Homo sapiens* RAP1B, member of RAS oncogene family (RAP1B), mRNA 736 |
| NM_016532 | *Homo sapiens* skeletal muscle and kidney enriched inositol phosphatase (SKIP), transcript variant 1, mRNA 1529 |
| NM_015292 | *Homo sapiens* likely ortholog of mouse membrane bound C2 domain containing protein (MBC2), mRNA 475 |
| NM_005870 | *Homo sapiens* sin3-associated polypeptide, 18 kDa (SAP18), mRNA 1651 |
| NM_006833 | *Homo sapiens* COP9 subunit 6 (MOV34 homolog, 34 kD) (COPS6), mRNA 1338 |
| NM_005718 | *Homo sapiens* actin related protein 2/3 complex, subunit 4, 20 kDa (ARPC4), mRNA 433 |
| NM_005719 | *Homo sapiens* actin related protein 2/3 complex, subunit 3, 21 kDa (ARPC3), mRNA 949 |
| NM_006372 | *Homo sapiens* NS1-associated protein 1 (NSAP1), mRNA 704 |
| NM_005180 | *Homo sapiens* B lymphoma Mo-MLV insertion region (mouse) (BMI1), mRNA 732 |
| NM_018975 | *Homo sapiens* telomeric repeat binding factor 2, interacting protein (TERF2IP), mRNA 684 |
| NM_005731 | *Homo sapiens* actin related protein 2/3 complex, subunit 2, 34 kDa (ARPC2), transcript variant 2, mRNA 2262 |
| NM_020151 | *Homo sapiens* START domain containing 7 (STARD7), transcript variant 1, mRNA 1562 |
| NM_005103 | *Homo sapiens* fasciculation and elongation protein zeta 1 (zygin I) (FEZ1), transcript variant 1, mRNA 672 |
| NM_012179 | *Homo sapiens* F-box only protein 7 (FBXO7), mRNA 865 |
| NM_020360 | *Homo sapiens* phospholipid scramblase 3 (PLSCR3), mRNA 3645 |
| NM_014891 | *Homo sapiens* PDGFA associated protein 1 (PDAP1), mRNA 1045 |
| NM_005745 | *Homo sapiens* accessory protein BAP31 (DXS1357E), mRNA 1525 |
| NM_005418 | *Homo sapiens* suppression of tumorigenicity 5 (ST5), transcript variant 1, mRNA 2305 |
| NM_006262 | *Homo sapiens* peripherin (PRPH), mRNA 484 |
| NM_133476 | *Homo sapiens* zinc finger protein 384 (ZNF384), mRNA 448 |
| NM_006570 | *Homo sapiens* Ras-related GTP-binding protein (RAGA), mRNA 903 |
| NM_006333 | *Homo sapiens* nuclear DNA-binding protein (C1D), mRNA 740 |

TABLE 1-continued

Housekeeping Genes.

| Accession No. | Description |
|---|---|
| NM_007285 | *Homo sapiens* GABA(A) receptor-associated protein-like 2 (GABARAPL2), mRNA 1265 |
| NM_006354 | *Homo sapiens* transcriptional adaptor 3-like (TADA3L) transcript variant 1, mRNA 1060 |
| NM_014302 | *Homo sapiens* Sec61 gamma (SEC61G), mRNA 644 |
| NM_006118 | *Homo sapiens* HS1 binding protein (HAX1), mRNA 1493 |
| NM_012100 | *Homo sapiens* aspartyl aminopeptidase (DNPEP), mRNA 419 |
| NM_015680 | *Homo sapiens* hypothetical protein CGI-57 (CGI-57), mRNA 976 |
| NM_030796 | *Homo sapiens* hypothetical protein DKFZp564K0822 (DKFZP564K0822), mRNA 572 |
| NM_024069 | *Homo sapiens* hypothetical protein MGC2749 (MGC2749), mRNA 573 |
| NM_013234 | *Homo sapiens* muscle specific gene (M9), mRNA 1056 |
| NM_013310 | *Homo sapiens* hypothetical protein AF038169 (AF038169), mRNA 1319 |
| NM_018507 | *Homo sapiens* hypothetical protein PRO1843 (PRO1843), mRNA 1081 |
| NM_017670 | *Homo sapiens* hypothetical protein FLJ20113 (FLJ20113), mRNA 999 |
| NM_016292 | *Homo sapiens* heat shock protein 75 (TRAP1), mRNA 615 |
| NM_014916 | *Homo sapiens* KIAA1079 protein (KIAA1079), mRNA 772 |
| NM_014696 | *Homo sapiens* KIAA0514 gene product (KIAA0514), mRNA 746 |
| NM_014630 | *Homo sapiens* KIAA0211 gene product (KIAA0211), mRNA 750 |
| NM_014761 | *Homo sapiens* KIAA0174 gene product (KIAA0174), mRNA 679 |
| NM_007286 | *Homo sapiens* synaptopodin (KIAA1029), mRNA 1349 |
| NM_007263 | *Homo sapiens* coatomer protein complex, subunit epsilon (COPE), mRNA 1272 |
| NM_006349 | *Homo sapiens* putative cyclin G1 interacting protein (CG1I), mRNA 591 |
| NM_006004 | *Homo sapiens* ubiquinol-cytochrome c reductase hinge protein (UQCRH), mRNA 1285 |
| NM_005787 | *Homo sapiens* Not56 (*D. melanogaster*)-like protein (NOT56L), mRNA 458 |
| NM_012412 | *Homo sapiens* histone H2A.F/Z variant (H2AV), transcript variant 1, mRNA 1070 |
| NM_012401 | *Homo sapiens* plexin B2 (PLXNB2), mRNA 929 |
| NM_007262 | *Homo sapiens* RNA-binding protein regulatory subunit (DJ-1), mRNA 1514 |
| NM_007273 | *Homo sapiens* repressor of estrogen receptor activity (REA), mRNA 1804 |
| NM_021009 | *Homo sapiens* ubiquitin C (UBC), mRNA 8892 |
| NM_023009 | *Homo sapiens* macrophage myristoylated alanine-rich C kinase substrate (MACMARCKS), mRNA 2025 |
| NM_015456 | *Homo sapiens* cofactor of BRCA1 (COBRA1), mRNA 848 |
| NM_005053 | *Homo sapiens* RAD23 homolog A (*S. cerevisiae*) (RAD23A), mRNA 1015 |
| NM_006830 | *Homo sapiens* ubiquinol-cytochrome c reductase (6.4 kD) subunit (UQCR), mRNA 1489 |
| NM_005682 | *Homo sapiens* G protein-coupled receptor 56 (GPR56), mRNA 742 |
| NM_012102 | *Homo sapiens* arginine-glutamic acid dipeptide (RE) repeats (RERE), mRNA 940 |
| NM_005550 | *Homo sapiens* kinesin family member C3 (KIFC3), mRNA 603 |
| NM_021960 | *Homo sapiens* myeloid cell leukemia sequence 1 (BCL2-related) (MCL1), mRNA 961 |
| NM_021959 | *Homo sapiens* protein phosphatase 1, regulatory (inhibitor) subunit 11 (PPP1R11), mRNA 462 |
| NM_014730 | *Homo sapiens* KIAA0152 gene product (KIAA0152), mRNA 713 |
| NM_014402 | *Homo sapiens* low molecular mass ubiquinone-binding protein (9.5 kD) (QP-C), mRNA 2805 |
| NM_007067 | *Homo sapiens* histone acetyltransferase (HBOA), mRNA 510 |
| NM_006086 | *Homo sapiens* tubulin, beta, 4 (TUBB4), mRNA 2239 |
| NM_014972 | *Homo sapiens* KIAA1049 protein (KIAA1049), mRNA 1011 |
| NM_024092 | *Homo sapiens* hypothetical protein MGC5508 (MGC5508), mRNA 749 |
| NM_021983 | *Homo sapiens* major histocompatibility complex, class II, DR beta 4 (HLA-DRB4), mRNA 1095 |
| NM_006510 | *Homo sapiens* ret finger protein (RFP), transcript variant alpha, mRNA 420 |
| NM_006711 | *Homo sapiens* RNA binding protein S1, serine-rich domain (RNPS1), transcript variant 1, mRNA 1376 |
| NM_006145 | *Homo sapiens* DnaJ (Hsp40) homolog, subfmaily B, member 1 (DNAJB1), mRNA 667 |
| NM_033142 | *Homo sapiens* chorionic gonadotropin, beta polypeptide 7 (CGB7), mRNA 773 |
| NM_006351 | *Homo sapiens* translocase of inner mitochondrial membrane 44 homolog (yeast) (TIMM44), mRNA 717 |
| NM_014281 | *Homo sapiens* fuse-binding protein-interacting repressor (SIAHBP1), transcript variant 2, mRNA 632 |
| NM_012106 | *Homo sapiens* binder of Arl Two (BART1), mRNA 760 |

TABLE 1-continued

Housekeeping Genes.

| Accession No. | Description |
|---|---|
| NM_021975 | *Homo sapiens* v-rel reticuloendotheliosis viral oncogene homolog A, nuclear factor of kappa light polypeptide gene enhancer in B-cells 3, p65 (avian) (RELA), mRNA 767 |
| NM_014874 | *Homo sapiens* mitofusin 2 (MFN2), mRNA 453 |
| NM_006796 | *Homo sapiens* AFG3 ATPase family gene 3-like 2 (yeast) (AFG3L2), nuclear gene encoding mitochondrial protein, mRNA 724 |
| NM_006666 | *Homo sapiens* RuvB-like 2 (*E. coli*) (RUVBL2), mRNA 690 |
| NM_005219 | *Homo sapiens* diaphanous homolog 1 (*Drosophila*) (DIAPH1), mRNA 592 |
| NM_033546 | *Homo sapiens* myosin regulatory light chain (MLC-B), mRNA 1231 |
| NM_032348 | *Homo sapiens* hypothetical protein MGC3047 (MGC3047), mRNA 553 |
| NM_024798 | *Homo sapiens* hypothetical protein FLJ13952 (FLJ13952), mRNA 2142 |
| NM_021103 | *Homo sapiens* thymosin, beta 10 (TMSB10), mRNA 1890 |
| NM_020195 | *Homo sapiens* HCDI protein (HCDI), mRNA 612 |
| NM_017432 | *Homo sapiens* prostate tumor over expressed gene 1 (PTOV1), mRNA 1509 |
| NM_014901 | *Homo sapiens* KIAA1100 protein (KIAA1100), mRNA 1999 |
| NM_014694 | *Homo sapiens* KIAA0605 gene product (KIAA0605), mRNA 532 |
| NM_007369 | *Homo sapiens* G-protein coupled receptor (RE2), mRNA 963 |
| NM_006156 | *Homo sapiens* neural precursor cell expressed, developmentally down-regulated 8 (NEDD8), mRNA 867 |
| NM_006429 | *Homo sapiens* chaperonin containing TCP1, subunit 7 (eta) (CCT7), mRNA 1434 |
| NM_006513 | *Homo sapiens* seryl-tRNA synthetase (SARS), mRNA 1130 |
| NM_005022 | *Homo sapiens* profilin 1 (PFN1), mRNA 2793 |
| NM_014654 | *Homo sapiens* syndecan 3 (N-syndecan) (SDC3), mRNA 1082 |
| NM_007209 | *Homo sapiens* ribosomal protein L35 (RPL35), mRNA 3463 |
| NM_006082 | *Homo sapiens* tubulin, alpha, ubiquitous (K-ALPHA-1), mRNA 4261 |
| NM_006362 | *Homo sapiens* nuclear RNA export factor 1 (NXF1), mRNA 729 |
| NM_014228 | *Homo sapiens* solute carrier family 6 (neurotransmitter transporter, L-proline), member 7 (SLC6A7), mRNA 1037 |
| NM_006411 | *Homo sapiens* 1-acylglycerol-3-phosphate O-acyltransferase 1 (lysophosphatidic acid acyltransferase, alpha) (AGPAT1), mRNA 742 |
| NM_021134 | *Homo sapiens* mitochondrial ribosomal protein L23 (MRPL23), mRNA 771 |
| NM_021974 | *Homo sapiens* polymerase (RNA) II (DNA directed) polypeptide F (POLR2F), mRNA 1169 |
| NM_006808 | *Homo sapiens* protein translocation complex beta (SEC61B), mRNA 679 |
| NM_005617 | *Homo sapiens* ribosomal protein S14 (RPS14), mRNA 7764 |
| NM_005520 | *Homo sapiens* heterogeneous nuclear ribonucleoprotein H1 (H) (HNRPH1), mRNA 2234 |
| NM_006755 | *Homo sapiens* transaldolase 1 (TALDO1), mRNA 874 |
| NM_006010 | *Homo sapiens* arginine-rich, mutated in early stage tumors (ARMET), mRNA 617 |
| NM_005088 | *Homo sapiens* DNA segment on chromosome X and Y (unique) 155 expressed sequence (DXYS155E), mRNA 524 |
| NM_014754 | *Homo sapiens* phosphatidylserine synthase 1 (PTDSS1), mRNA 930 |
| NM_021953 | *Homo sapiens* forkhead box M1 (FOXM1), mRNA 567 |
| NM_006908 | *Homo sapiens* ras-related C3 botulinum toxin substrate 1 (rho family, small GTP binding protein Rac1) (RAC1), transcript variant Rac1, mRNA 1978 |
| NM_014231 | *Homo sapiens* vesicle-associated membrane protein 1 (synaptobrevin 1) (VAMP 1), transcript variant VAMP-1A, mRNA 745 |
| NM_014833 | *Homo sapiens* KIAA0618 gene product (KIAA0618), mRNA 607 |
| NM_005157 | *Homo sapiens* v-abl Abelson murine leukemia viral oncogene homolog 1 (ABL1), transcript variant a, mRNA 777 |
| NM_006325 | *Homo sapiens* RAN, member RAS oncogene family (RAN), mRNA 3100 |
| NM_007245 | *Homo sapiens* ataxin 2 related protein (A2LP), transcript variant 1, mRNA 564 |
| NM_007008 | *Homo sapiens* reticulon 4 (RTN4), mRNA 1267 |
| NM_006782 | *Homo sapiens* zinc finger protein-like 1 (ZFPL1), mRNA 712 |
| NM_006694 | *Homo sapiens* jumping translocation breakpoint (JTB), mRNA 2394 |
| NM_006703 | *Homo sapiens* nudix (nucleoside diphosphate linked moiety X)-type motif 3 (NUDT3), mRNA 566 |
| NM_006032 | *Homo sapiens* copine VI (neuronal) (CPNE6), mRNA 1540 |
| NM_012227 | *Homo sapiens* Pseudoautosomal GTP-binding protein-like (PGPL), mRNA 494 |
| NM_014604 | *Homo sapiens* Tax interaction protein 1 (TIP-1), mRNA 748 |
| NM_021642 | *Homo sapiens* Fc fragment of IgG, low affinity IIa, receptor for (CD32) (FCGR2A), mRNA 772 |
| NM_005354 | *Homo sapiens* jun D proto-oncogene (JUND), mRNA 4967 |

TABLE 1-continued

Housekeeping Genes.

| Accession No. | Description |
|---|---|
| NM_020529 | *Homo sapiens* nuclear factor of kappa light polypeptide gene enhancer in B-cells inhibitor, alpha (NFKBIA), mRNA 922 |
| NM_005561 | *Homo sapiens* lysosomal-associated membrane protein 1 (LAMP1), mRNA 2865 |
| NM_014774 | *Homo sapiens* KIAA0494 gene product (KIAA0494), mRNA 604 |
| NM_014390 | *Homo sapiens* EBNA-2 co-activator (100 kD) (p100), mRNA 867 |
| NM_014623 | *Homo sapiens* male-enhanced antigen (MEA), mRNA 548 |
| NM_014453 | *Homo sapiens* putative breast adenocarcinoma marker (32 kD) (BC-2), mRNA 597 |
| NM_012127 | *Homo sapiens* Cip1-interacting zinc finger protein (CIZ1), mRNA 1051 |
| NM_012099 | *Homo sapiens* CD3-epsilon-associated protein; antisense to ERCC-1 (ASE-1), mRNA 472 |
| NM_006888 | *Homo sapiens* calmodulin 1 (phosphorylase kinase, delta) (CALM1), mRNA 2161 |
| NM_006867 | *Homo sapiens* RNA-binding protein gene with multiple splicing (RBPMS), mRNA 1255 |
| NM_006743 | *Homo sapiens* RNA binding motif protein 3 (RBM3), mRNA 2949 |
| NM_006688 | *Homo sapiens* C1q-related factor (CRF), mRNA 3604 |
| NM_006295 | *Homo sapiens* valyl-tRNA synthetase 2 (VARS2), mRNA 721 |
| NM_006283 | *Homo sapiens* transforming, acidic coiled-coil containing protein 1 (TACC1), mRNA 867 |
| NM_006221 | *Homo sapiens* protein (peptidyl-prolyl cis/trans isomerase) NIMA-interacting 1 (PIN1), mRNA 561 |
| NM_006148 | *Homo sapiens* LIM and SH3 protein 1 (LASP1), mRNA 1067 |
| NM_005954 | *Homo sapiens* metallothionein 3 (growth inhibitory factor (neurotrophic)) (MT3), mRNA 2311 |
| NM_006003 | *Homo sapiens* ubiquinol-cytochrome c reductase, Rieske iron-sulfur polypeptide 1 (UQCRFS1), nuclear gene encoding mitochondrial protein, mRNA 951 |
| NM_005998 | *Homo sapiens* chaperonin containing TCP1, subunit 3 (gamma) (CCT3), mRNA 1098 |
| NM_005997 | *Homo sapiens* transcription factor-like 1 (TCFL1), mRNA 505 |
| NM_005629 | *Homo sapiens* solute carrier family 6 (neurotransmitter transporter, creatine), member 8 (SLC6A8), mRNA 628 |
| NM_005548 | *Homo sapiens* lysyl-tRNA synthetase (KARS), mRNA 1193 |
| NM_005545 | *Homo sapiens* immunoglobulin superfamily containing leucine-rich repeat (ISLR), mRNA 796 |
| NM_005507 | *Homo sapiens* cofilin 1 (non-muscle) (CFL1), mRNA 5155 |
| NM_005381 | *Homo sapiens* nucleolin (NCL), mRNA 2043 |
| NM_005439 | *Homo sapiens* myeloid leukemia factor 2 (MLF2), mRNA 697 |
| NM_006445 | *Homo sapiens* PRP8 pre-mRNA processing factor 8 homolog (yeast) (PRPF8), mRNA 1384 |
| NM_019059 | *Homo sapiens* homolog of Tom7 (*S. cerevisiae*) (TOM7), mRNA 2364 |
| NM_006039 | *Homo sapiens* mannose receptor, C type 2 (MRC2), mRNA 564 |
| NM_006066 | *Homo sapiens* aldo-keto reductase family 1, member A1 (aldehyde reductase) (AKR1A1), transcript variant 1, mRNA 879 |
| NM_013318 | *Homo sapiens* hypothetical protein LQFBS-1 (LQFBS-1), mRNA 485 |
| NM_006098 | *Homo sapiens* guanine nucleotide binding protein (G protein), beta polypeptide 2-like 1 (GNB2L1), mRNA 7556 |
| NM_007359 | *Homo sapiens* MLN51 protein (MLN51), mRNA 975 |
| NM_017510 | *Homo sapiens* gp25L2 protein (HSGP25L2G), mRNA 1032 |
| NM_015399 | *Homo sapiens* breast cancer metastasis-suppressor 1 (BRMS1), mRNA 476 |
| NM_014508 | *Homo sapiens* apolipoprotein B mRNA editing enzyme, catalytic polypeptide-like 3C (APOBEC3C), mRNA 816 |
| NM_018955 | *Homo sapiens* ubiquitin B (UBB), mRNA 6074 |
| NM_006368 | *Homo sapiens* cAMP responsive element binding protein 3 (luman) (CREB3), mRNA 533 |
| NM_015024 | *Homo sapiens* RAN binding protein 16 (RANBP16), mRNA 559 |
| NM_031420 | *Homo sapiens* mitochondrial ribosomal protein L9 (MRPL9), nuclear gene encoding mitochondrial protein, mRNA 476 |
| NM_013232 | *Homo sapiens* programmed cell death 6 (PDCD6), mRNA 816 |
| NM_005917 | *Homo sapiens* malate dehydrogenase 1, NAD (soluble) (MDH1), mRNA 1724 |
| NM_032801 | *Homo sapiens* junctional adhesion molecule 3 (JAM3), mRNA 624 |
| NM_030662 | *Homo sapiens* mitogen-activated protein kinase kinase 2 (MAP2K2), mRNA 663 |
| NM_006268 | *Homo sapiens* requiem, apoptosis response zinc finger gene (REQ), mRNA 784 |
| NM_006826 | *Homo sapiens* tyrosine 3-monooxygenase/tryptophan 5-monooxygenase activation protein, theta polypeptide (YWHAQ), mRNA 1917 |
| NM_144582 | *Homo sapiens* hypothetical protein MGC32043 (MGC32043), mRNA 712 |

TABLE 1-continued

Housekeeping Genes.

| Accession No. | Description |
| --- | --- |
| NM_144565 | *Homo sapiens* hypothetical protein FLJ32334 (FLJ32334), mRNA 5319 |
| NM_005984 | *Homo sapiens* solute carrier family 25 (mitochondrial carrier; citrate transporter), member 1 (SLC25A1), mRNA 620 |
| NM_017828 | *Homo sapiens* hypothetical protein FLJ20452 (FLJ20452), mRNA 546 |
| NM_020150 | *Homo sapiens* SAR1 protein (SAR1), mRNA 581 |
| NM_014610 | *Homo sapiens* alpha glucosidase II alpha subunit (G2AN), mRNA 1293 |
| NM_014225 | *Homo sapiens* protein phosphatase 2 (formerly 2A), regulatory subunit A (PR 65), alpha isoform (PPP2R1A), mRNA 1687 |
| NM_006937 | *Homo sapiens* SMT3 suppressor of mif two 3 homolog 2 (yeast) (SMT3H2), mRNA 2940 |
| NM_005726 | *Homo sapiens* Ts translation elongation factor, mitochondrial (TSFM), mRNA 408 |
| NM_005347 | *Homo sapiens* heat shock 70 kDa protein 5 (glucose-regulated protein, 78 kDa) (HSPA5), mRNA 1111 |
| NM_014255 | *Homo sapiens* transmembrane protein 4 (TMEM4), mRNA 505 |
| NM_006815 | *Homo sapiens* coated vesicle membrane protein (RNP24), mRNA 1642 |
| NM_005456 | *Homo sapiens* mitogen-activated protein kinase 8 interacting protein 1 (MAPK8IP1), mRNA 885 |
| NM_005273 | *Homo sapiens* guanine nucleotide binding protein (G protein), beta polypeptide 2 (GNB2), mRNA 1478 |
| NM_007260 | *Homo sapiens* lysophospholipase II (LYPLA2), mRNA 2000 |
| NM_007103 | *Homo sapiens* NADH dehydrogenase (ubiquinone) flavoprotein 1, 51 kDa (NDUFV1), mRNA 803 |
| NM_017797 | *Homo sapiens* BTB (POZ) domain containing 2 (BTBD2), mRNA 1030 |
| NM_016237 | *Homo sapiens* anaphase promoting complex subunit 5 (ANAPC5), mRNA 935 |
| NM_005801 | *Homo sapiens* putative translation initiation factor (SUI1), mRNA 1058 |
| NM_005216 | *Homo sapiens* dolichyl-diphosphooligosaccharide-protein glycosyltransferase (DDOST), mRNA 1421 |
| NM_016457 | *Homo sapiens* protein kinase D2 (PKD2), mRNA 662 |
| NM_006442 | *Homo sapiens* DR1-associated protein 1 (negative cofactor 2 alpha) (DRAP1), mRNA 561 |
| NM_021019 | *Homo sapiens* myosin, light polypeptide 6, alkali, smooth muscle and non-muscle (MYL6), transcript variant 1, mRNA 5933 |
| NM_005112 | *Homo sapiens* WD repeat domain 1 (WDR1), transcript variant 2, mRNA 809 |
| NM_005370 | *Homo sapiens* mel transforming oncogene (derived from cell line NK14)-RAB8 homolog (MEL), mRNA 682 |
| NM_006289 | *Homo sapiens* talin 1 (TLN1), mRNA 1811 |
| NM_005698 | *Homo sapiens* secretory carrier membrane protein 3 (SCAMP3), transcript variant 1, mRNA 602 |
| NM_024011 | *Homo sapiens* cell division cycle 2-like 2 (CDC2L2), transcript variant 1, mRNA 430 |
| NM_005105 | *Homo sapiens* RNA binding motif protein 8A (RBM8A), mRNA 785 |
| NM_006013 | *Homo sapiens* ribosomal protein L10 (RPL10), mRNA 10721 |
| NM_005786 | *Homo sapiens* serologically defined colon cancer antigen 33 (SDCCAG33), mRNA 1435 |
| NM_007104 | *Homo sapiens* ribosomal protein L10a (RPL10A), mRNA 3006 |
| NM_005762 | *Homo sapiens* tripartite motif-containing 28 (TRIM28), mRNA 1473 |
| NM_012138 | *Homo sapiens* apoptosis antagonizing transcription factor (AATF), mRNA 504 |
| NM_015318 | *Homo sapiens* Rho-specific guanine nucleotide exchange factor p114 (P114-RHO-GEF), mRNA 405 |
| NM_012423 | *Homo sapiens* ribosomal protein L13a (RPL13A), mRNA 9545 |
| NM_021128 | *Homo sapiens* polymerase (RNA) II (DNA directed) polypeptide L, 7.6 kDa (POLR2L), mRNA 1524 |
| NM_032635 | *Homo sapiens* seven transmembrane domain protein (NIFIE14), mRNA 1121 |
| NM_005080 | *Homo sapiens* X-box binding protein 1 (XBP1), mRNA 1772 |
| NM_006389 | *Homo sapiens* hypoxia up-regulated 1 (HYOU1), mRNA 1076 |
| NM_024112 | *Homo sapiens* chromosome 9 open reading frame 16 (C9orf16), mRNA 598 |
| NM_006817 | *Homo sapiens* chromosome 12 open reading frame 8 (C12orf8), mRNA 910 |
| NM_022830 | *Homo sapiens* hypothetical protein FLJ22347 (FLJ22347), mRNA 6021 |
| NM_019884 | *Homo sapiens* glycogen synthase kinase 3 alpha (GSK3A), mRNA 963 |
| NM_021107 | *Homo sapiens* mitochondrial ribosomal protein S12 (MRPS12), nuclear gene encoding mitochondrial protein, transcript variant 1, mRNA 828 |
| NM_021074 | *Homo sapiens* NADH dehydrogenase (ubiquinone) flavoprotein 2, 24 kDa (NDUFV2), mRNA 539 |
| NM_014944 | *Homo sapiens* calsyntenin 1 (CLSTN1), mRNA 1620 |

TABLE 1-continued

Housekeeping Genes.

| Accession No. | Description |
| --- | --- |
| NM_014764 | Homo sapiens DAZ associated protein 2 (DAZAP2), mRNA 1802 |
| NM_015343 | Homo sapiens likely ortholog of Xenopus dullard (HSA011916), mRNA 933 |
| NM_014420 | Homo sapiens dickkopf homolog 4 (Xenopus laevis) (DKK4), mRNA 426 |
| NM_005884 | Homo sapiens p21(CDKN1A)-activated kinase 4 (PAK4), mRNA 375 |
| NM_012407 | Homo sapiens protein kinase C, alpha binding protein (PRKCABP), mRNA 553 |
| NM_012111 | Homo sapiens chromosome 14 open reading frame 3 (C14orf3), mRNA 717 |
| NM_007144 | Homo sapiens zinc finger protein 144 (Mel-18) (ZNF144), mRNA 798 |
| NM_007108 | Homo sapiens transcription elongation factor B (SIII), polypeptide 2 (18 kDa, elongin B) (TCEB2), mRNA 1192 |
| NM_007278 | Homo sapiens GABA(A) receptor-associated protein (GABARAP), mRNA 2335 |
| NM_007100 | Homo sapiens ATP synthase, H+ transporting, mitochondrial F0 complex, subunit e (ATP5I), mRNA 2623 |
| NM_006936 | Homo sapiens SMT3 suppressor of mif two 3 homolog 1 (yeast) (SMT3H1), mRNA 1187 |
| NM_006899 | Homo sapiens isocitrate dehydrogenase 3 (NAD+) beta (IDH3B), mRNA 565 |
| NM_006801 | Homo sapiens KDEL (Lys-Asp-Glu-Leu) (SEQ ID NO: 1) endoplasmic reticulum protein retention receptor 1 (KDELR1), mRNA 1270 |
| NM_006612 | Homo sapiens kinesin family member 1C (KIF1C), mRNA 600 |
| NM_006659 | Homo sapiens tubulin, gamma complex associated protein 2 (TUBGCP2), mRNA 701 |
| NM_006595 | Homo sapiens apoptosis inhibitor 5 (APIS), mRNA 1173 |
| NM_006401 | Homo sapiens acidic (leucine-rich) nuclear phosphoprotein 32 family, member B (ANP32B), mRNA 2354 |
| NM_006423 | Homo sapiens Rab acceptor 1 (prenylated) (RABAC1), mRNA 1706 |
| NM_006460 | Homo sapiens HMBA-inducible (HIS1), mRNA 369 |
| NM_006356 | Homo sapiens ATP synthase, H+transporting, mitochondrial F0 complex, subunit d (ATP5H), mRNA 1047 |
| NM_005891 | Homo sapiens acetyl-Coenzyme A acetyltransferase 2 (acetoacetyl Coenzyme A thiolase) (ACAT2), mRNA 911 |
| NM_005839 | Homo sapiens serine/arginine repetitive matrix 1 (SRRM1), mRNA 745 |
| NM_005594 | Homo sapiens nascent-polypeptide-associated complex alpha polypeptide (NACA), mRNA 3678 |
| NM_005340 | Homo sapiens histidine triad nucleotide binding protein 1 (HINT1), mRNA 2270 |
| NM_005175 | Homo sapiens ATP synthase, H+ transporting, mitochondrial F0 complex, subunit c (subunit 9), isoform 1 (ATP5G1), mRNA 1266 |
| NM_005165 | Homo sapiens aldolase C, fructose-bisphosphate (ALDOC), mRNA 1052 |
| NM_005001 | Homo sapiens NADH dehydrogenase (ubiquinone) 1 alpha subcomplex, 7, 14.5 kDa (NDUFA7), mRNA 806 |
| NM_001402 | |
| NM_001958 | |
| NM_001961 | |
| NM_002714 | |
| NM_002808 | |
| NM_002809 | |
| NM_004898 | |
| NM_007182 | |
| NM_032378 | |

In various embodiments of the present invention, the reference value is chromosome 15 centromere copy number. In various embodiments, the reference value for chromosome 15q26 copy number is chromosome 15 centromere copy number.

The chromosome 15q26 copy number and chromosome 15 centromere copy number can be ascertained by various methods. For example, they can be ascertained through chip based measurements with or without a normal reference, or by using centromeric FISH probes, which is an assay for testing for copy number changes using microscopy.

In various embodiments, the number of chromosome 15 centromere probes is compared to the number of 15q26.1 probes, in each cell using a microscope. If the numbers match, there is no relative gain of 15q26. Increase in this context can be a numerical increase, e.g., 2→3 copies. In various embodiments, copy gain can be defined by the absolute copy number determined in an interphase FISH assay averaged by counting a minimum of 20 tumor cells. In various embodiments, copy gain can be defined as the ratio of 15q26/centromere 15 determined in an interphase FISH assay counting both spots (15q26 and cent15) in the same cells and averaging over a minimum of 20 cells. In various embodiments, copy gain can be determined using a normalized genome wide assay such as SNP array, genome sequencing and the like, wherein the normalization is done using the ASCAT algorithm or other appropriate algorithms. In various embodiments, the cutpoints can be anything above normal, which is 2 absolute copies of 15q26, or ratio>1 for 15q26/cent15. Due to the typical noise in these assays, in certain embodiments, the cutoff is defined by adding a standard error. Accordingly, copy>2.6 or ratio>1.3 signify copy number gain.

Thus, in various embodiments, a copy number gain of over 2.6 or a ratio of over 1.3 indicates a copy number gain in the sample.

In other embodiments, the reference value for chromosome 15q26 is determined from a non-cancer cell sample from the subject or a member of the same species to which the subject belongs. In certain embodiments, the reference value is determined from a non-cancerous cell or tissue sample that is the same type of cell or tissue as the cancer cell from the subject. In certain embodiments, the reference value is determined from a non-cancerous cell or tissue sample that is not the same type of cell or tissue as the cancer cell from the subject. In various embodiments, array-based or sequencing-based technologies can be used wherein the reference can be from patients' normal cells (e.g., blood), or it can be a collection of blood samples.

Copy number abnormalities can be detected using methods, such as, for example, array CGH using BAC, cDNA and/or oligonucleotide arrays; microsatellite markers; STRs, RFLPS; etc.

Additional methods for evaluating copy number of nucleic acid in a sample include, but are not limited to, hybridization-based assays. One method for evaluating the copy number of encoding nucleic acid in a sample involves a Southern Blot. In a Southern Blot, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid. Alternatively, a Northern blot may be utilized for evaluating the copy number of encoding nucleic acid in a sample. In a Northern blot, mRNA is hybridized to a probe specific for the target region. Comparison of the intensity of the hybridization signal from the probe for the target region with control probe signal from analysis of normal mRNA (e.g., a non-amplified portion of the same or related cell, tissue, organ, etc.) provides an estimate of the relative copy number of the target nucleic acid. Similar methods for determining copy number can be performed using transcriptional arrays, which are well-known in the art.

An alternative means for determining the copy number is in situ hybridization (e.g., Angerer (1987) *Meth. Enzymol* 152: 649). Generally, in situ hybridization comprises the following steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application.

Preferred hybridization-based assays include, but are not limited to, traditional "direct probe" methods such as Southern blots or in situ hybridization (e.g., FISH and FISH plus SKY), and "comparative probe" methods such as comparative genomic hybridization (CGH), e.g., cDNA-based or oligonucleotide-based CGH. The methods can be used in a wide variety of formats including, but not limited to, substrate (e.g. membrane or glass) bound methods or array-based approaches.

In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained.

The probes are typically labeled, e.g., with radioisotopes or fluorescent reporters. Preferred probes are sufficiently long so as to specifically hybridize with the target nucleic acid(s) under stringent conditions. The preferred size range is from about 200 bases to about 1000 bases.

In some applications it is necessary to block the hybridization capacity of repetitive sequences. Thus, in some embodiments, tRNA, human genomic DNA, or Cot-I DNA is used to block non-specific hybridization.

In CGH methods, a first collection of nucleic acids (e.g., from a sample, e.g., a possible tumor) is labeled with a first label, while a second collection of nucleic acids (e.g., a control, e.g., from a healthy cell/tissue) is labeled with a second label. The ratio of hybridization of the nucleic acids is determined by the ratio of the two (first and second) labels binding to each fiber in the array. Where there are chromosomal deletions or multiplications, differences in the ratio of the signals from the two labels will be detected and the ratio will provide a measure of the copy number. Array-based CGH may also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays. Hybridization protocols suitable for use with the methods of the invention are described, e.g., in Albertson (1984) *EMBO J.* 3: 1227-1234; Pinkel (1988) *Proc. Natl. Acad. Sci. USA* 85: 9138-9142; EPO Pub. No. 430,402; *Methods in Molecular Biology*, Vol. 33: In situ Hybridization Protocols, Choo, ed., Humana Press, Totowa, N.J. (1994), etc. In one embodiment, the hybridization protocol of Pinkel, et al. (1998) *Nature Genetics* 20: 207-211, or of Kallioniemi (1992) *Proc. Natl Acad Sci USA* 89:5321-5325 (1992) is used.

The methods of the invention are particularly well suited to array-based hybridization formats. Array-based CGH is described in U.S. Pat. No. 6,455,258, the contents of which are incorporated herein by reference. In still another embodiment, amplification-based assays can be used to measure copy number. In such amplification-based assays, the nucleic acid sequences act as a template in an amplification reaction (e.g., Polymerase Chain Reaction (PCR). In a quantitative amplification, the amount of amplification product will be proportional to the amount of template in the original sample. Comparison to appropriate controls, e.g. healthy tissue, provides a measure of the copy number.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR anlaysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the invention. In fluorogenic quantitative PCR, quantitation is based on amount of fluorescence signals, e.g., TaqMan and sybr green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

In still other embodiments of the methods provided herein, sequencing of individual nucleic molecules (or their amplification products) is performed, as an alternative to hybridization-based assays, using nucleic acid sequencing techniques. In one embodiment, a high throughput parallel sequencing technique that isolates single nucleic acid molecules of a population of nucleic acid molecules prior to sequencing may be used. Such strategies may use so-called "next generation sequencing systems" including, without limitation, sequencing machines and/or strategies well known in the art, such as those developed by Illumina/Solexa (the Genome Analyzer; Bennett et al. (2005) Pharmacogenomics, 6:373-20 382), by Applied Biosystems, Inc. (the SOLiD Sequencer; solid.appliedbiosystems.com), by Roche (e.g., the 454 GS FLX sequencer; Margulies et al. (2005) *Nature*, 437:376-380; U.S. Pat. Nos. 6,274,320; 6,258,568; 6,210,891), by Heliscope™ system from Helicos Biosciences (see, e.g., U.S. Patent App. Pub. No. 2007/0070349), and by others. Other sequencing strategies such as stochastic sequencing (e.g., as developed by Oxford Nanopore) may also be used, e.g., as described in International Application No. PCT/GB2009/001690 (pub. no. WO/2010/004273). All of the copy number determining strategies described herein can similarly be applied to any of other nucleic acid-based analysis described herein, such as for BLM, FANCI, or 15q26 the like described further below.

Therapies

These therapies can be selected, used, administered, etc., in accordance with various embodiment of the present invention.

Platinum-comprising therapy, include but are not limited platinum chemotherapeutic agents, such as cisplatin, carboplatin, oxaliplatin, nedaplatin, and iproplatin. Other antineoplastic platinum coordination compounds are well known in the art, can be modified according to well-known methods in the art, and include the compounds disclosed in U.S. Pat. Nos. 4,996,337, 4,946,954, 5,091,521, 5,434,256, 5,527,905, and 5,633,243, all of which are incorporated herein by reference. In various embodiments described herein, the platinum comprising cancer therapy comprises cisplatinum or cis-diamminedichloroplatinum, phenanthriplatin, carboplatin, oxaliplatin, or a platinum complex that is activated by ultraviolet A light.

In various embodiments, non-platinum comprising therapies include, non-platinum chemotherapy. Non-platinum chemotherapy may be, but is not limited to, those selected from among the following groups of compounds: cytotoxic antibiotics, antimetabolities, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: treosulfan, and trofosfamide; plant alkaloids: vinblastine, paclitaxel, docetaxol; DNA topoisomerase inhibitors: doxorubicin, epirubicin, etoposide, camptothecin, topotecan, irinotecan, teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2) inhibitors are used and such inhibitors are well known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. No. Re. 36,397); and NU1025 (Bowman et al.). The foregoing examples of non-platinum chemotherapeutic agents are illustrative, and are not intended to be limiting.

In various embodiments, non-platinum comprising therapies include, for example, radiation therapy. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In various embodiments, non-platinum comprising therapies include, for example, immunotherapy. Immunotherapy may comprise, for example, use of cancer vaccines and/or sensitized antigen presenting cells. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines.

In various embodiments, non-platinum comprising therapies include, for example, hormonal therapy, Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

In various embodiments described herein, the anthracycline is epirubincin or doxorubicin.

The duration and/or dose of treatment with anti-cancer therapies may vary according to the particular anti-cancer agent or combination thereof. An appropriate treatment time for a particular cancer therapeutic agent will be appreciated by the skilled artisan. The invention contemplates the continued assessment of optimal treatment schedules for each cancer therapeutic agent, where the genetic signature of the cancer of the subject as determined by the methods of the invention is a factor in determining optimal treatment doses and schedules.

Cancers for which the Genetic Signature can be Determined

The methods of the invention can be used to determine the genetic signature of many different cancers. Specific examples of types of cancers for which the genetic signature can be determined by the methods encompassed by the invention include, but are not limited to, human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

In some embodiments, the cancer whose genetic signature is determined by the method of the invention is an epithelial cancer such as, but not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, brenner, or undifferentiated. In still other embodiments, the cancer is breast cancer, ovarian cancer or lung cancer. In particular embodiments, the cancer is triple negative breast cancer.

Subjects

In various embodiments, the subject for whom predicted efficacy of an anti-cancer therapy is determined, is a mammal (e.g., mouse, rat, primate, non-human mammal, domestic animal such as dog, cat, cow, horse), and is preferably a human. In another embodiment of the methods of the invention, the subject has not undergone chemotherapy or radiation therapy. In alternative embodiments, the subject has undergone chemotherapy or radiation therapy (e.g., such as with cisplatin, carboplatin, and/or taxane). In related embodiments, the subject has not been exposed to levels of radiation or chemotoxic agents above those encountered generally or on average by the subjects of a species. In certain embodiments, the subject has had surgery to remove cancerous or precancerous tissue. In other embodiments, the cancerous tissue has not been removed, e.g., the cancerous tissue may be located in an inoperable region of the body, such as in a tissue that is essential for life, or in a region where a surgical procedure would cause considerable risk of harm to the patient, or e.g., the subject is given the anti-cancer therapy prior to removal of the cancerous tissue.

Nucleic Acid Sample Preparation

A. Nucleic Acid Isolation

Nucleic acid samples derived from cancerous and non-cancerous cells of a subject that can be used in the methods of the invention to determine the genetic signature of a cancer can be prepared by means well known in the art. For example, surgical procedures or needle biopsy aspiration can be used to collect cancerous samples from a subject. In some embodiments, it is important to enrich and/or purify the cancerous tissue and/or cell samples from the non-cancerous tissue and/or cell samples. In other embodiments, the cancerous tissue and/or cell samples can then be microdissected to reduce the amount of normal tissue contamination prior to extraction of genomic nucleic acid or pre-RNA for use in the methods of the invention. In still another embodiment, the cancerous tissue and/or cell samples are enriched for cancer cells by at least 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or any range in between, in cancer cell content. Such enrichment can be accomplished according to methods well-known in the art, such as needle microdissection, laser microdissection, fluorescence activated cell sorting, and immunological cell sorting. In one embodiment, an automated machine performs the hyperproliferative cell enrichment to thereby transform the biological sample into a purified form enriched for the presence of hyperproliferative cells.

Collecting nucleic acid samples from non-cancerous cells of a subject can also be accomplished with surgery or aspiration. In surgical procedures where cancerous tissue is removed, surgeons often remove non-cancerous tissue and/or cell samples of the same tissue type of the cancer patient for comparison. Nucleic acid samples can be isolated from such non-cancerous tissue of the subject for use in the methods of the invention. In certain embodiments of the methods of the invention, nucleic acid samples from non-cancerous tissues are not derived from the same tissue type as the cancerous tissue and/or cells sampled, and/or are not derived from the cancer patient. The nucleic acid samples from non-cancerous tissues may be derived from any non-cancerous and/or disease-free tissue and/or cells. Such non-cancerous samples can be collected by surgical or non-surgical procedures. In certain embodiments, non-cancerous nucleic acid samples are derived from tumor-free tissues. For example, non-cancerous samples may be collected from lymph nodes, peripheral blood lymphocytes, and/or mononuclear blood cells, or any subpopulation thereof. In a preferred embodiment, the non-cancerous tissue is not pre-cancerous tissue, e.g., it does not exhibit any indicia of a pre-neoplastic condition such as hyperplasia, metaplasia, or dysplasia.

In one embodiment, the nucleic acid samples used to compute a reference value are taken from at least 1, 2, 5, 10, 20, 30, 40, 50, 100, or 200 different organisms of that species. According to certain aspects of the invention, nucleic acid "derived from" genomic DNA, as used in the methods of the invention, e.g., in hybridization experiments to determine BLM expression, FANCI expression, or 15q26 copy number, chromosome 15 centromere copy number can be fragments of genomic nucleic acid generated by restriction enzyme digestion and/or ligation to other nucleic acid, and/or amplification products of genomic nucleic acids, or pre-messenger RNA (pre-mRNA), amplification products of pre-mRNA, or genomic DNA fragments grown up in cloning vectors generated, e.g., by "shotgun" cloning methods. In certain embodiments, genomic nucleic acid samples are digested with restriction enzymes.

B. Amplification of Nucleic Acids

Though the nucleic acid sample need not comprise amplified nucleic acid, in some embodiments, the isolated nucleic acids can be processed in manners requiring and/or taking advantage of amplification. The genomic DNA samples of a subject optionally can be fragmented using restriction endonucleases and/or amplified prior to determining analysis. In one embodiment, the DNA fragments are amplified using polymerase chain reaction (PCR). Methods for practicing PCR are well known to those of skill in the art. One advantage of PCR is that small quantities of DNA can be used. For example, genomic DNA from a subject may be about 150 ng, 175, ng, 200 ng, 225 ng, 250 ng, 275 ng, or 300 ng of DNA.

In certain embodiments of the methods of the invention, the nucleic acid from a subject is amplified using a single primer pair. For example, genomic DNA samples can be digested with restriction endonucleases to generate fragments of genomic DNA that are then ligated to an adaptor DNA sequence which the primer pair recognizes In other embodiments of the methods of the invention, the nucleic acid of a subject is amplified using sets of primer pairs specific to BLM, FANCI, 15q26, or chromosome 15 centromere copy and in instances wherein BRCA1, BRCA2, ER, PgR and/or HER2 receptor expression is also to be assessed, sets of primer pairs specific to BRCA1, BRCA2, ER, PgR and/or HER2 receptor. Such sets of primer pairs each recognize genomic DNA sequences flanking BLM, FANCI, 15q26, or chromosome 15 centromere and BRCA1, BRCA2, ER, PgR and/or HER2 receptor wherein the expression is also to be assessed. A DNA sample suitable for hybridization can be obtained, e.g., by polymerase chain reaction (PCR) amplification of genomic DNA, fragments of genomic DNA, fragments of genomic DNA ligated to adaptor sequences or cloned sequences. Computer programs that are well known in the art can be used in the design of primers with the desired specificity and optimal amplification properties, such as Oligo version 5.0 (National Biosciences). PCR methods are well known in the art, and are described, for example, in Innis et al., eds., 1990, PCR Protocols: A Guide to Methods And Applications, Academic Press Inc., San Diego, Calif. It will be apparent to one skilled in the art that controlled robotic systems are useful for isolating and amplifying nucleic acids and can be used.

In other embodiments, where genomic DNA of a subject is fragmented using restriction endonucleases and amplified prior to analysis, the amplification can comprise cloning regions of genomic DNA of the subject. In such methods, amplification of the DNA regions is achieved through the cloning process. For example, expression vectors can be engineered to express large quantities of particular fragments of genomic DNA of the subject (Sambrook, J. et al., eds., 1989, Molecular Cloning: A Laboratory Manual, 2nd Ed., Cold Spring Harbor Laboratory Press, Cold Spring Harbor, N.Y., at pp. 9.47-9.51).

In yet other embodiments, where the DNA of a subject is fragmented using restriction endonucleases and amplified prior to analysis, the amplification comprises expressing a nucleic acid encoding a gene, or a gene and flanking genomic regions of nucleic acids, from the subject. RNA (pre-messenger RNA) that comprises the entire transcript including introns is then isolated and used in the methods of the invention to analyze and provide a genetic signature of a cancer. In certain embodiments, no amplification is required. In such embodiments, the genomic DNA, or pre-RNA, of a subject may be fragmented using restriction endonucleases or other methods. The resulting fragments may be hybridized to SNP probes. Typically, greater quantities of DNA are needed to be isolated in comparison to the quantity of DNA or pre-mRNA needed where fragments are amplified. For example, where the nucleic acid of a subject is not amplified, a DNA sample of a subject for use in hybridization may be about 400 ng, 500 ng, 600 ng, 700 ng, 800 ng, 900 ng, or 1000 ng of DNA or greater. Alternatively, in other embodiments, methods are used that require very small amounts of nucleic acids for analysis, such as less than 400 ng, 300 ng, 200 ng, 100 ng, 90 ng, 85 ng, 80 ng, 75 ng, 70 ng, 65 ng, 60 ng, 55 ng, 50 ng, or less, such as is used for molecular inversion probe (MIP) assays. These techniques are particularly useful for analyzing clinical samples, such as paraffin embedded formalin-fixed material or small core needle biopsies, characterized as being readily available but generally having reduced DNA quality (e.g., small, fragmented DNA) and/or not providing large amounts of nucleic acids.

C. Hybridization

The nucleic acid samples derived from a subject used in the methods of the invention can be hybridized to arrays comprising probes (e.g., oligonucleotide probes) in order to identify BLM, FANCI, 15q26, or chromosome 15 centromere and in instances wherein BRCA1, BRCA2, ER, PgR and/or HER2 receptor expression is also to be assessed, comprising probes in order to identify BRCA1, BRCA2, ER, PgR and/or HER2 receptor. Hybridization can also be used to determine whether the BLM, FANCI, 15q26, or chromosome 15 centromere identified exhibit total copy number change, copy number gain, and copy number loss in nucleic acid samples from cancerous tissues and/or cells of the subject. In preferred embodiments, the probes used in the methods of the invention comprise an array of probes that can be tiled on a DNA chip (e.g., SNP oligonucleotide probes). In some embodiments, BLM expression, FANCI expression, 15q26 copy number, or chromosome 15 centromere copy number is determined by a method that does not comprise detecting a change in size of restriction enzyme-digested nucleic acid fragments. In other embodiments, SNPs are analyzed to identify BLM expression or FANCI expression, 15q26 copy number or chromosome 15 centromere copy number. Hybridization and wash conditions used in the methods of the invention are chosen so that the nucleic acid samples to be analyzed by the invention specifically bind or specifically hybridize to the complementary oligonucleotide sequences of the array, preferably to a specific array site, wherein its complementary DNA is located. In some embodiments, the complementary DNA can be completely matched or mismatched to some degree as used, for example, in Affymetrix oligonucleotide arrays such as those used to analyze SNPs in MIP assays. The single-stranded synthetic oligodeoxyribonucleic acid DNA probes of an array may need to be denatured prior to contact with the nucleic acid samples from a subject, e.g., to remove hairpins or dimers which form due to self-complementary sequences.

Optimal hybridization conditions will depend on the length of the probes and type of nucleic acid samples from a subject. General parameters for specific (i.e., stringent) hybridization conditions for nucleic acids are described in Sambrook, J. et al., eds., 1989, Molecular Cloning: A Laboratory Manual, 2nd Ed., Cold Spring Harbor Laboratory Press, Cold Spring Harbor, N.Y., at pp. 9.47-9.51 and 11.55-11.61; Ausubel et al., eds., 1989, Current Protocols in Molecules Biology, Vol. 1, Green Publishing Associates, Inc., John Wiley & Sons, Inc., New York, at pp. 2.10.1-2.10.16. Exemplary useful hybridization conditions are provided in, e.g., Tijessen, 1993, Hybridization with Nucleic Acid Probes, Elsevier Science Publishers B. V. and Kricka, 1992, Nonisotopic DNA Probe Techniques, Academic Press, San Diego, Calif.

D. Oligonucleotide Nucleic Acid Arrays

In some embodiments of the methods of the present invention, DNA arrays can be used to determine total copy number change, copy number gain, and copy number loss by measuring the level of hybridization of the nucleic acid sequence to oligonucleotide probes that comprise complementary sequences. Hybridization can be used to determine the presence or absence of heterozygosity. Various formats of DNA arrays that employ oligonucleotide "probes," (i.e., nucleic acid molecules having defined sequences) are well known to those of skill in the art. Typically, a set of nucleic acid probes, each of which has a defined sequence, is immobilized on a solid support in such a manner that each different probe is immobilized to a predetermined region. In certain embodiments, the set of probes forms an array of positionally-addressable binding (e.g., hybridization) sites on a support. Each of such binding sites comprises a plurality of oligonucleotide molecules of a probe bound to the predetermined region on the support. More specifically, each probe of the array is preferably located at a known, predetermined position on the solid support such that the identity (i.e., the sequence) of each probe can be determined from its position on the array (i.e., on the support or surface). Microarrays can be made in a number of ways, of which several are described herein. However produced, microarrays share certain characteristics, they are reproducible, allowing multiple copies of a given array to be produced and easily compared with each other.

Preferably, the microarrays are made from materials that are stable under binding (e.g., nucleic acid hybridization) conditions. The microarrays are preferably small, e.g., between about 1 $cm^2$ and 25 $cm^2$, preferably about 1 to 3 $cm^2$. However, both larger and smaller arrays are also contemplated and may be preferable, e.g., for simultaneously evaluating a very large number of different probes. Oligonucleotide probes can be synthesized directly on a support to form the array. The probes can be attached to a solid support or surface, which may be made, e.g., from glass, plastic (e.g., polypropylene, nylon), polyacrylamide, nitrocellulose, gel, or other porous or nonporous material. The set of immobilized probes or the array of immobilized probes is contacted with a sample containing labeled nucleic acid species so that nucleic acids having sequences complementary to an immobilized probe hybridize or bind to the probe. After separation of, e.g., by washing off, any unbound material, the bound, labeled sequences are detected and measured. The measurement is typically conducted with computer assistance. Using DNA array assays, complex mixtures of labeled nucleic acids, e.g., nucleic acid fragments derived a restriction digestion of genomic DNA from non-cancerous tissue, can be analyzed. DNA array technologies have made it possible to determine the expression level or copy number BLM, FANCI, 15q26, or chromosome 15 centromere, or BRCA1, BRCA2, ER, PgR and/or HER2 receptor expression in instances where BRCA1, BRCA2, ER, PgR and/or HER2 receptor expression is also assessed.

In certain embodiments, high-density oligonucleotide arrays are used in the methods of the invention. These arrays containing thousands of oligonucleotides complementary to defined sequences, at defined locations on a surface can be synthesized in situ on the surface by, for example, photolithographic techniques (see, e.g., Fodor et al., 1991, Science 251:767-773; Pease et al., 1994, Proc. Natl. Acad. Sci. U.S.A. 91:5022-5026; Lockhart et al., 1996, Nature Biotechnology 14:1675; U.S. Pat. Nos. 5,578,832; 5,556,752; 5,510,270; 5,445,934; 5,744,305; and 6,040,138). Methods for generating arrays using inkjet technology for in situ oligonucleotide synthesis are also known in the art (see, e.g., Blanchard, International Patent Publication WO 98/41531, published Sep. 24, 1998; Blanchard et al., 1996, Biosensors And Bioelectronics 11:687-690; Blanchard, 1998, in Synthetic DNA Arrays in Genetic Engineering, Vol. 20, J. K. Setlow, Ed., Plenum Press, New York at pages 111-123). Another method for attaching the nucleic acids to a surface is by printing on glass plates, as is described generally by Schena et al. (1995, Science 270:467-470). Other methods for making microarrays, e.g., by masking (Maskos and Southern, 1992, Nucl. Acids. Res. 20:1679-1684), may also be used. When these methods are used, oligonucleotides (e.g., 15 to 60-mers) of known sequence are synthesized directly on a surface such as a derivatized glass slide. The array produced can be redundant, with several oligonucleotide molecules corresponding to each informative locus of interest (e.g., SNPs, RFLPs, STRs, etc.).

One exemplary means for generating the oligonucleotide probes of the DNA array is by synthesis of synthetic polynucleotides or oligonucleotides, e.g., using N-phosphonate or phosphoramidite chemistries (Froehler et al., 1986, Nucleic Acid Res. 14:5399-5407; McBride et al., 1983, Tetrahedron Lett. 24:246-248). Synthetic sequences are typically between about 15 and about 600 bases in length, more typically between about 20 and about 100 bases, most preferably between about 40 and about 70 bases in length. In some embodiments, synthetic nucleic acids include non-natural bases, such as, but by no means limited to, inosine.

As noted above, nucleic acid analogues may be used as binding sites for hybridization. An example of a suitable nucleic acid analogue is peptide nucleic acid (see, e.g., Egholm et al., 1993, Nature 363:566-568; U.S. Pat. No. 5,539,083). In alternative embodiments, the hybridization sites (i.e., the probes) are made from plasmid or phage clones of regions of genomic DNA corresponding to SNPs or the complement thereof. The size of the oligonucleotide probes used in the methods of the invention can be at least 10, 20, 25, 30, 35, 40, 45, or 50 nucleotides in length. It is well known in the art that although hybridization is selective for complementary sequences, other sequences which are not perfectly complementary may also hybridize to a given probe at some level. Thus, multiple oligonucleotide probes with slight variations can be used, to optimize hybridization of samples. To further optimize hybridization, hybridization stringency condition, e.g., the hybridization temperature and the salt concentrations, may be altered by methods that are well known in the art.

In preferred embodiments, the high-density oligonucleotide arrays used in the methods of the invention comprise oligonucleotides corresponding to BLM, FANCI, 15q26, or chromosome 15 centromere or in instances wherein BRCA1, BRCA2, ER, PgR and/or HER2 receptor expression is also assessed, the arrays also comprise oligonucleotides corresponding to BRCA1, BRCA2, ER, PgR and/or HER2 receptor. The oligonucleotide probes may comprise DNA or DNA "mimics" (e.g., derivatives and analogues) corresponding to a portion of each informative locus of interest (e.g., SNPs, RFLPs, STRs, etc.) in a subject's genome. The oligonucleotide probes can be modified at the base moiety, at the sugar moiety, or at the phosphate backbone. Exemplary DNA mimics include, e.g., phosphorothioates. For each SNP locus, a plurality of different oligonucleotides may be used that are complementary to the sequences of sample nucleic acids. For example, for a single informative locus of interest (e.g., SNPs, RFLPs, STRs, etc.) about 2, 3, 4, 5, 6, 7, 8,9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more different oligonucleotides can be used. Each of the oligonucleotides for a particular informative locus of interest may have a slight variation in perfect matches, mismatches, and flanking sequence around the SNP. In certain embodiments, the probes are generated such that the probes for a particular informative locus of interest comprise overlapping and/or successive overlapping sequences which span or are tiled across a genomic region containing the target site, where all the probes contain the target site. By way of example, overlapping probe sequences can be tiled at steps of a predetermined base interval, e. g. at steps of 1, 2, 3, 4, 5, 6, 7, 8, 9, or 10 bases intervals. In certain embodiments, the assays can be performed using arrays suitable for use with molecular inversion probe protocols such as described by Wang et al. (2007) Genome Biol. 8, R246. For oligonucleotide probes targeted at nucleic acid species of closely resembled (i.e., homologous) sequences, "cross-hybridization" among similar probes can significantly contaminate and confuse the results of hybridization measurements. Cross-hybridization is a particularly significant concern in the detection of SNPs since the sequence to be detected (i.e., the particular SNP) must be distinguished from other sequences that differ by only a single nucleotide. Cross-hybridization can be minimized by regulating either the hybridization stringency condition and/or during post-hybridization washings. Highly stringent conditions allow detection of allelic variants of a nucleotide sequence, e.g., about 1 mismatch per 10-30 nucleotides. There is no single hybridization or washing condition which is optimal for all different nucleic acid sequences. For particular arrays of BLM, FANCI, 15q26, or chromosome 15 centromere, or of BRCA1, BRCA2, ER, PgR and/or HER2 receptor these conditions can be identical to those suggested by the manufacturer or can be adjusted by one of skill in the art. In preferred embodiments, the probes used in the methods of the invention are immobilized (i.e., tiled) on a glass slide called a chip. For example, a DNA microarray can comprises a chip on which oligonucleotides (purified single-stranded DNA sequences in solution) have been robotically printed in an (approximately) rectangular array with each spot on the array corresponds to a single DNA sample which encodes an oligonucleotide. In summary the process comprises, flooding the DNA microarray chip with a labeled sample under conditions suitable for hybridization to occur between the slide sequences and the labeled sample, then the array is washed and dried, and the array is scanned with a laser microscope to detect hybridization. In certain embodiments there are at least 250, 500, 1,000, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, 30,000, 31,000, 32,000, 33,000,34,000, 35,000, 36,000, 37,000, 38,000, 39,000, 40,000, 41,000, 42,000, 43,000, 44,000, 45,000, 50,000, 60,000, 70,000, 80,000, 90,000, 100,000 or more or any range in between, of BLM, FANCI, 15q26, or chromosome 15 centromere, or of BRCA1, BRCA2, ER, PgR and/or HER2 receptor for which probes appear on the array (with match/mismatch probes for a single locus of interest or probes tiled across a single locus of interest counting as one locus of interest). The maximum number of BLM, FANCI, 15q26, or chromosome 15 centromere, or of BRCA1, BRCA2, ER, PgR and/or HER2 receptor being probed per array is determined by the size of the genome and genetic diversity of the subjects species. DNA chips are well known in the art and can be purchased in pre-5 fabricated form with sequences specific to particular species. In some embodiments, the Genome-Wide Human SNP Array 6.0™ and/or the 50K XbaI arrays (Affymetrix, Santa Clara, Calif.) are used in the methods of the invention. In other embodiments, SNPs and/or DNA copy number can be detected and quantitated using sequencing methods, such as "next-generation sequencing methods" as described further above.

E. Signal Detection

In some embodiments, nucleic acid samples derived from a subject are hybridized to the binding sites of an array described herein. In certain embodiments, nucleic acid samples derived from each of the two sample types of a subject (i.e., cancerous and non-cancerous) are hybridized to separate, though identical, arrays. In certain embodiments, nucleic acid samples derived from one of the two sample types of a subject (i.e., cancerous and non-cancerous) is hybridized to such an array, then following signal detection the chip is washed to remove the first labeled sample and reused to hybridize the remaining sample. In other embodiments, the array is not reused more than once. In certain embodiments, the nucleic acid samples derived from each of the two sample types of a subject (i.e., cancerous and non-cancerous) are differently labeled so that they can be distinguished. When the two samples are mixed and hybridized to the same array, the relative intensity of signal from each sample is determined for each site on the array, and any relative difference in abundance of an allele of BLM, FANCI, 15q26, or chromosome 15 centromere, or of BRCA1, BRCA2, ER, PgR and/or HER2 receptor. Signals can be recorded and, in some embodiments, analyzed by computer. In one embodiment, the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the array, a ratio of the emission of the two fluorophores can be calculated, which may help in eliminating cross hybridization signals to more accurately determining whether a particular SNP locus is heterozygous or homozygous.

F. Labeling

In some embodiments, the nucleic acids samples, fragments thereof, or fragments thereof ligated to adaptor regions used in the methods of the invention are detectably labeled. For example, the detectable label can be a fluorescent label, e.g., by incorporation of nucleotide analogues. Other labels suitable for use in the present invention include, but are not limited to, biotin, iminobiotin, antigens, cofactors, dinitrophenol, lipoic acid, olefinic compounds, detectable polypeptides, electron rich molecules, enzymes capable of generating a detectable signal by action upon a substrate, and radioactive isotopes.

Radioactive isotopes include that can be used in conjunction with the methods of the invention, but are not limited to, 32P and 14C. Fluorescent molecules suitable for the present invention include, but are not limited to, fluorescein and its derivatives, rhodamine and its derivatives, texas red, 5'carboxy-fluorescein ("FAM"), 2',7'-dimethoxy-4',5'-dichloro-6-carboxy-fluorescein ("JOE"), N,N,N',N'-tetramethyl-6-carboxy-rhodamine ("TAMRA"), 6-carboxy-X-rhodamine ("ROX"), HEX, TET, IRD40, and IRD41.

Fluorescent molecules which are suitable for use according to the invention further include: cyamine dyes, including but not limited to Cy2, Cy3, Cy3.5, CY5, Cy5.5, Cy7 and FLUORX; BODIPY dyes including but not limited to BODIPY-FL, BODIPY-TR, BODIPY-TMR, BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes which will be known to those who are skilled in the art. Electron rich indicator molecules suitable for the present invention include, but are not limited to, ferritin, hemocyanin, and colloidal gold.

Two-color fluorescence labeling and detection schemes may also be used (Shena et al., 1995, Science 270:467-470). Use of two or more labels can be useful in detecting variations due to minor differences in experimental conditions (e.g., hybridization conditions). In some embodiments of the invention, at least 5, 10, 20, or 100 dyes of different colors can be used for labeling. Such labeling would also permit analysis of multiple samples simultaneously which is encompassed by the invention.

The labeled nucleic acid samples, fragments thereof, or fragments thereof ligated to adaptor regions that can be used in the methods of the invention are contacted to a plurality of oligonucleotide probes under conditions that allow sample nucleic acids having sequences complementary to the probes to hybridize thereto. Depending on the type of label used, the hybridization signals can be detected using methods well known to those of skill in the art including, but not limited to, X-Ray film, phosphor imager, or CCD camera. When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al. (1996) Genome Res. 6, 639-645). In a preferred embodiment, the arrays are scanned with a laser fluorescence scanner with a computer controlled X-Y stage and a microscope objective. Sequential excitation of the two fluorophores is achieved with a multi-line, mixed gas laser, and the emitted light is split by wavelength and detected with two photomultiplier tubes. Such fluorescence laser scanning devices are described, e.g., in Schena et al. (1996) Genome Res. 6, 639-645. Alternatively, a fiber-optic bundle can be used such as that described by Ferguson et al. (1996) Nat. Biotech. 14, 1681-1684. The resulting signals can then be analyzed to determine the BLM expression, FANCI expression, 15q26 copy number, or chromosome 15 centromere copy number, using computer software.

G. Algorithms for Analyzing BLM, FANCI, 15q26, or Chromosome 15 Centromere

Once the hybridization signal has been detected the resulting data can be analyzed using algorithms. In certain embodiments, the algorithm for determining the expression of BLM or FANCI, or copy number 15q26 or chromosome 15 centromere is based on well-known methods. Additional representative illustrations of such well known algorithms are provided in the Examples section below.

H. Computer Implementation Systems and Methods

In certain embodiments, the methods of the invention implement a computer program to calculate a copy number, copy number gain, copy number loss, and expression levels. For example, a computer program can be used to perform the algorithms described herein. A computer system can also store and manipulate data generated by the methods of the present invention which comprises a plurality of hybridization signal changes/profiles during approach to equilibrium in different hybridization measurements and which can be used by a computer system in implementing the methods of this invention. In certain embodiments, a computer system receives probe hybridization data; (ii) stores probe hybridization data; and (iii) compares probe hybridization data to determine the state of BLM, FANCI, 15q26, or, chromosome 15 centromere, and/or of BRCA1, BRCA2, ER, PgR and/or HER2 receptor in said nucleic acid sample from cancerous or pre-cancerous tissue. The copy number, copy number gain, copy number loss, or expression levels is then calculated. In some embodiments, a computer system (i) compares the determined copy number, copy number gain, copy number loss, and expression levels to a threshold value or reference value; and (ii) outputs an indication of whether said copy number, copy number gain, copy number loss, and expression levels is above or below a threshold value, or a genetic signature based on said indication. In certain embodiments, such computer systems are also considered part of the present invention.

Numerous types of computer systems can be used to implement the analytic methods of this invention according to knowledge possessed by a skilled artisan in the bioinformatics and/or computer arts.

Several software components can be loaded into memory during operation of such a computer system. The software components can comprise both software components that are standard in the art and components that are special to the present invention (e.g., dCHIP software described in Lin et al. (2004) *Bioinformatics* 20, 1233-1240; CRLMM software described in Silver et al. (2007) *Cell* 128, 991-1002; Aroma Affymetrix software described in Richardson et al. (2006) *Cancer Cell* 9, 121-132. The methods of the invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.). In certain embodiments, the computer comprises a database for storage of hybridization signal profiles. Such stored profiles can be accessed and used to calculate a copy number, copy number gain, copy number loss, or expression level. For example, of the hybridization signal profile of a sample derived from the non-cancerous tissue of a subject and/or profiles generated from population-based distributions of BLM, FANCI, 15q26, or chromosome 15 centromere, and/or of BRCA1, BRCA2, ER, PgR and/or HER2 receptor in relevant populations of the same species were stored, it could then be compared to the hybridization signal profile of a sample derived from the cancerous tissue of the subject.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

Once a laboratory technician or laboratory professional or group of laboratory technicians or laboratory professionals determines whether a sample has a copy number, copy number gain, copy number loss, or expression level as described above (e.g., step (1) in many of the methods above), the same or a different laboratory technician or laboratory professional (or group) can analyze a plurality of test BLM, FANCI, 15q26, or chromosome 15 centromere to determine whether there is a copy number, copy number gain, copy number loss, or expression level (e.g., step (2) in many of the methods above). Next, the same or a different laboratory technician or laboratory professional (or group) can combine the a copy number, copy number gain, copy number loss, or expression level data from the test BLM, FANCI, 15q26, or chromosome 15 centromere to derive a copy number, copy number gain, copy number loss, or expression level (e.g., step (3) in many of the methods above). Optionally, the same or a different laboratory technician or laboratory professional (or group) can correlate the copy number, copy number gain, copy number loss, or expression level to an increased or decreased likelihood of response to a particular therapy (e.g., those mentioned above).

In various embodiments, provided herein is a computer readable storage medium comprising: a storing data module containing data from a sample comprising a cancer cell obtained from a subject that represents an expression level from an assay for BLM and/or FANCI, or copy number of 15q26; a comparison module that compares the data stored on the storing data module with a reference data and/or control data, and to provide a comparison content, and an output module displaying the comparison content for the user, wherein the increased expression of BLM and/or FANCI, or copy number gain of 15q26 indicates that the subject is susceptible to platinum-comprising, or anthracycline-comprising cancer therapy.

In various embodiments, the control data comprises data from a population of non-cancerous healthy individuals. In various embodiments, the control data comprises data BRAC1 expression, and/or a housekeeping gene expression.

Embodiments of the invention can be described through functional modules, which are defined by computer executable instructions recorded on computer readable media and which cause a computer to perform method steps when executed. The modules are segregated by function, for the sake of clarity. However, it should be understood that the modules/systems need not correspond to discreet blocks of code and the described functions can be carried out by the execution of various code portions stored on various media and executed at various times. Furthermore, it should be appreciated that the modules may perform other functions, thus the modules are not limited to having any particular functions or set of functions.

The computer readable storage media 30 can be any available tangible media that can be accessed by a computer. Computer readable storage media includes volatile and nonvolatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (eraseable programmable read only memory), EEPROM (electrically eraseable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing.

Computer-readable data embodied on one or more computer-readable media may define instructions, for example, as part of one or more programs that, as a result of being executed by a computer, instruct the computer to perform one or more of the functions described herein, and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied may reside on one or more of the components of either of a system, or a computer readable storage medium described herein, may be distributed across one or more of such components.

The computer-readable media may be transportable such that the instructions stored thereon can be loaded onto any computer resource to implement the aspects of the present invention discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a computer to implement aspects of the present invention. The computer executable instructions may be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

Figure 12:
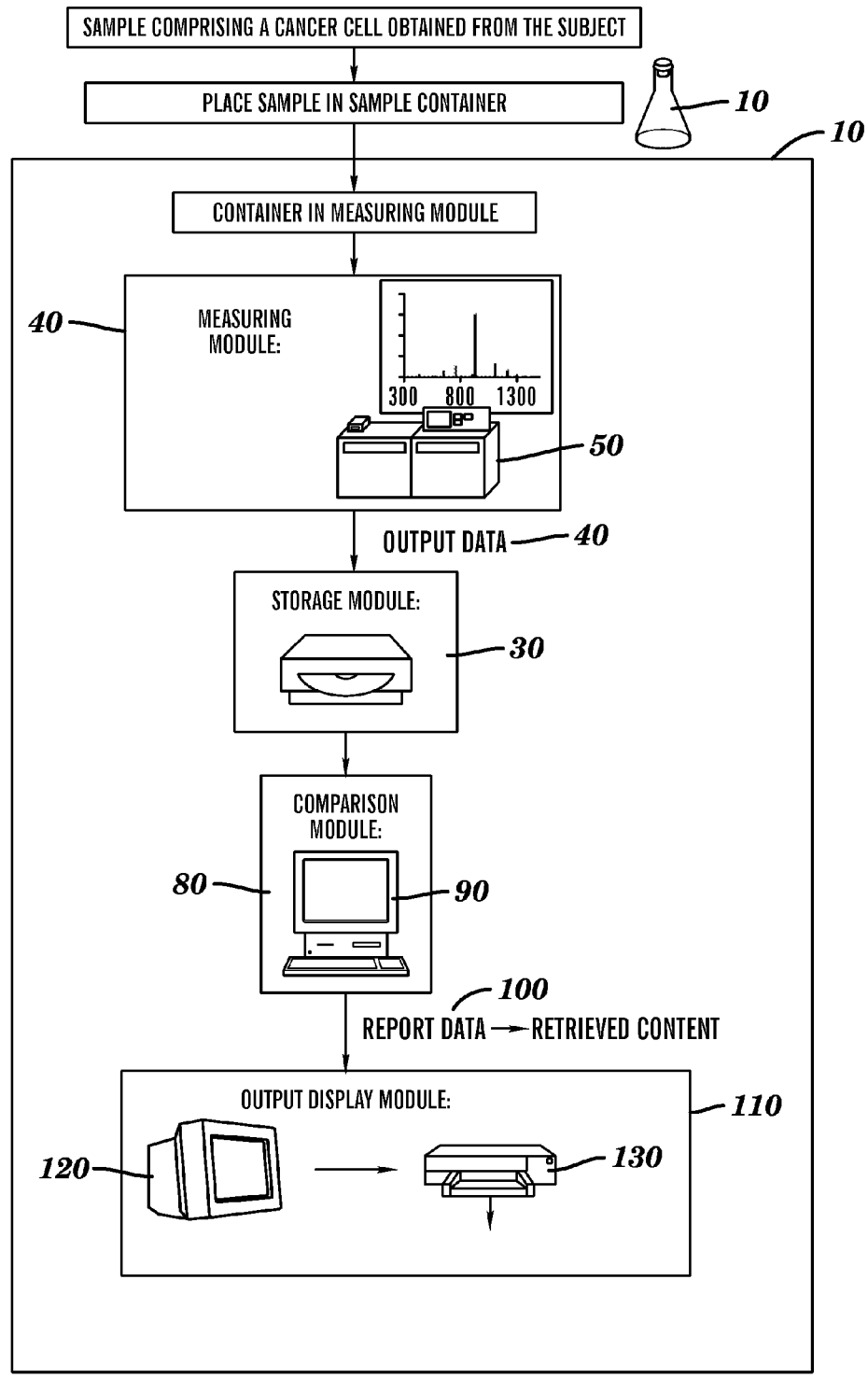
FIG. 12 depicts functional modules of various embodiments of the invention.
Figure 13:
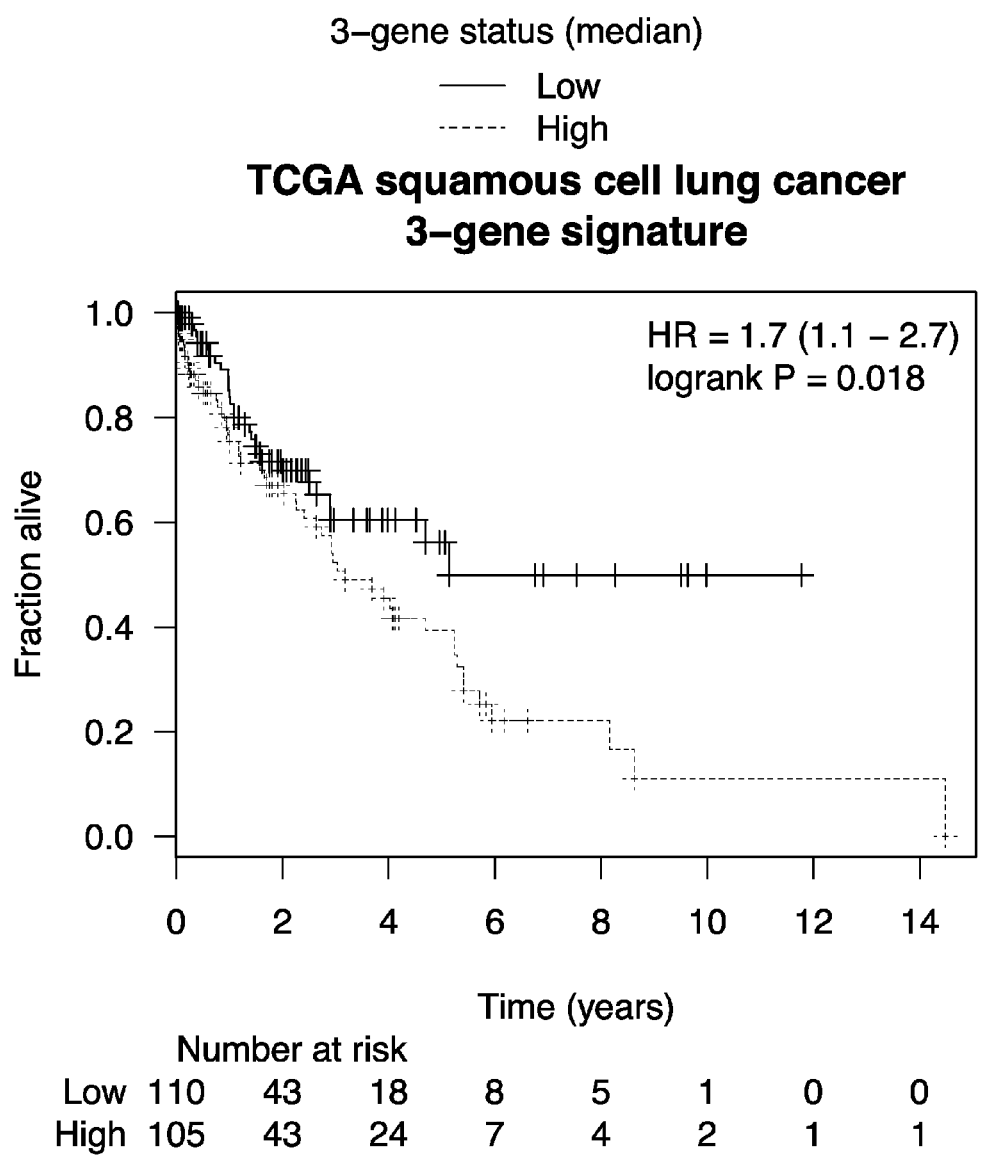
FIG. 13 depicts survival time with Kaplan-Meier plot, showing over-all survival of patients from the TCGA squamous cell lung cancer cohort, split by the median of the three gene signature calculated as the ratio of BRCA1 expression over the mean of FANI and BLM expression.
Figure 14:
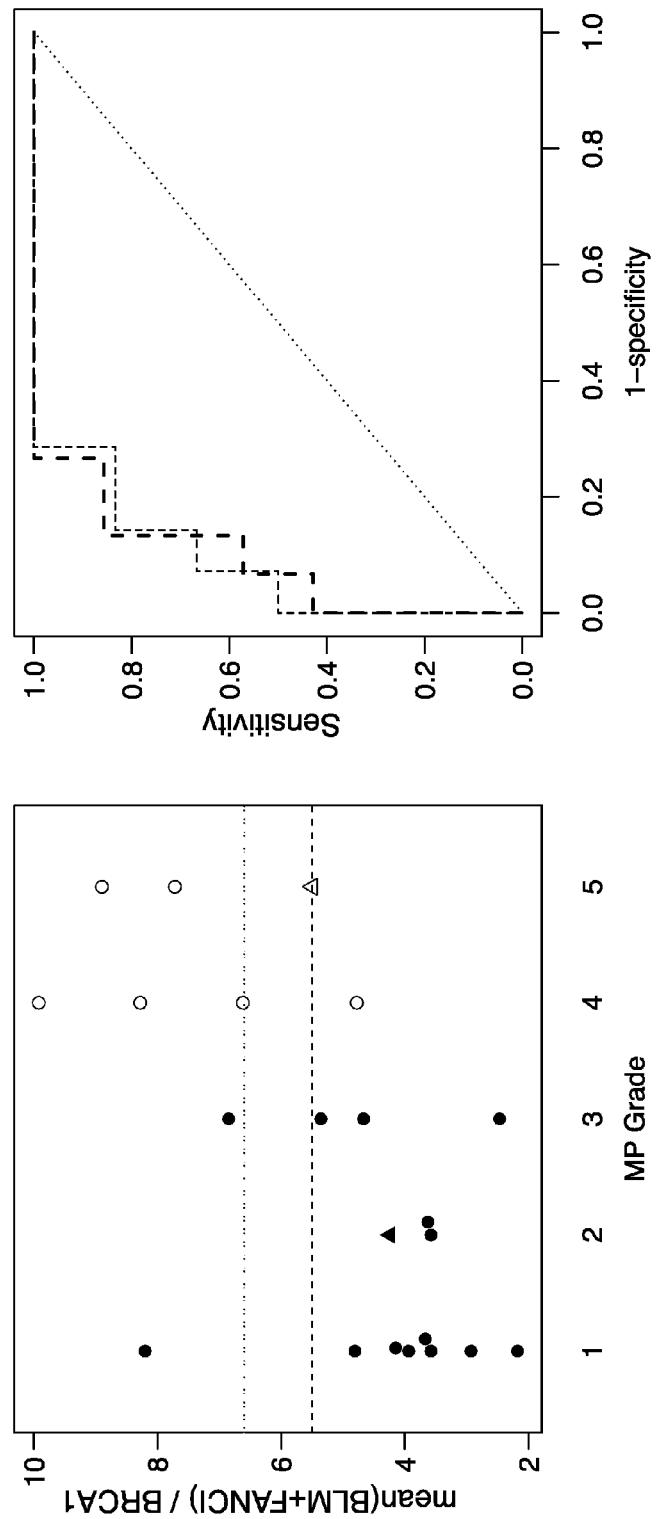
FIG. 14 shows the BLM+FANCI/BRCA1 signature. The Cisplatin-2 trial, separating resistant (MP 1-2-3) from sensitive (MP 4-5) cases is optimized for qPCR data. Blue line is based on all samples, while red is based on wtBRCA1. The optimum ratio is calculated by ROC curve, and shows an optimum ratio of 5.5 for all cases, on a log2 scale. In un-logged values, this is equivalent of 45 fold.
Figure 15:
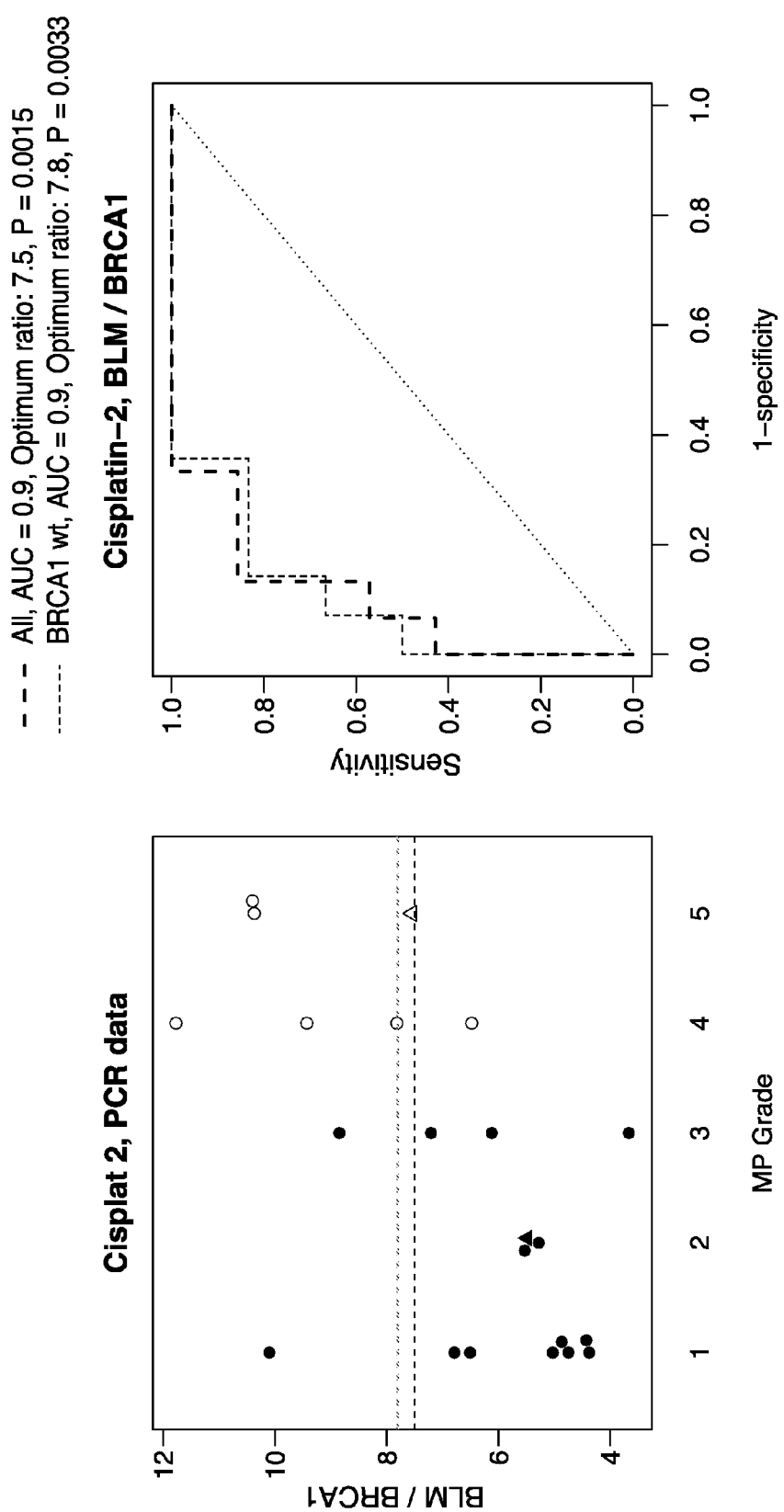
FIG. 15 shows BLM/BRCA1 signature. The Cisplatin-2 trial, separating resistant (MP 1-2-3) from sensitive (MP 4-5) cases is optimized for qPCR data. The optimum ratio is 7.5 for all cases, on a log2 scale, which is equivalent of 180 fold or 7.5 cycles on a PCR machine. This is a very large difference.
Figure 16:
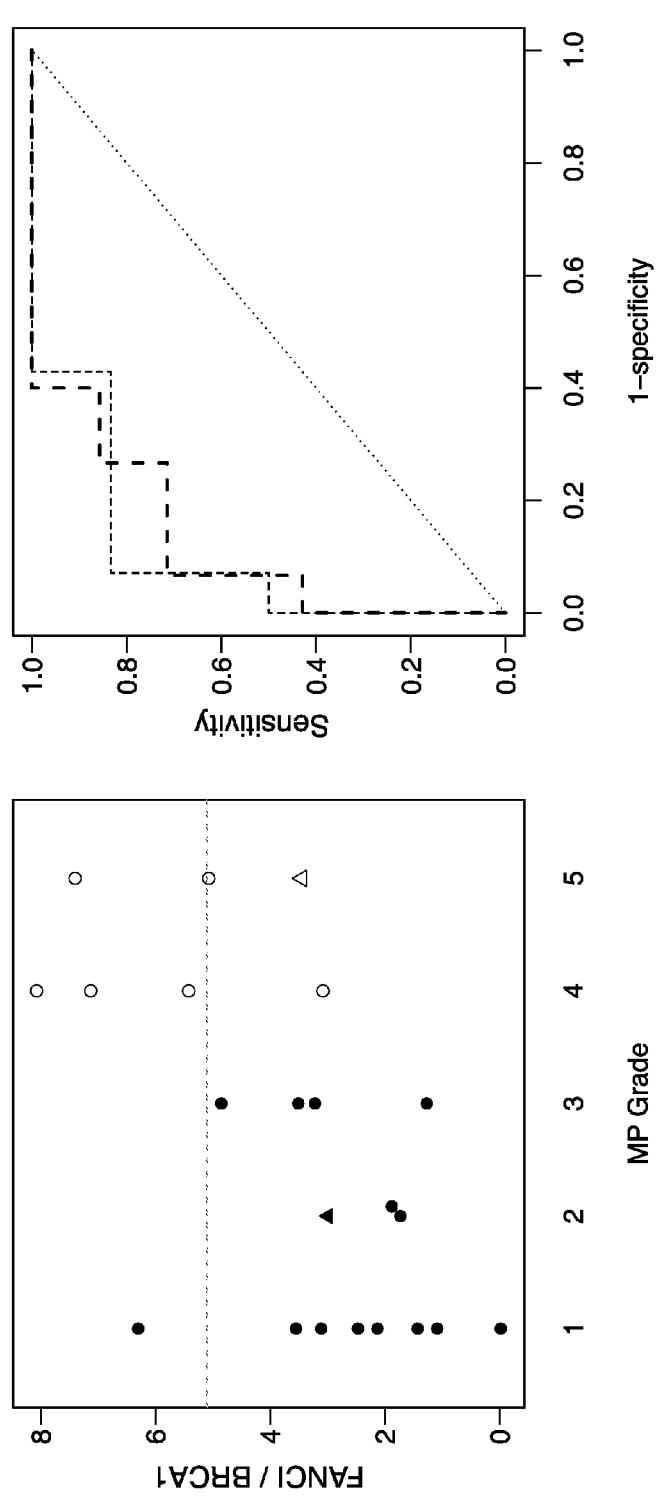
FIG. 16 shows FANCI/BRCA1 signature. The Cisplatin-2 trial, separating resistant (MP 1-2-3) from sensitive (MP 4-5) cases is optimized for qPCR data. The optimum ratio is 5.1 for all cases, on a log2 scale, which is equivalent of 34 fold.
Figure 17:
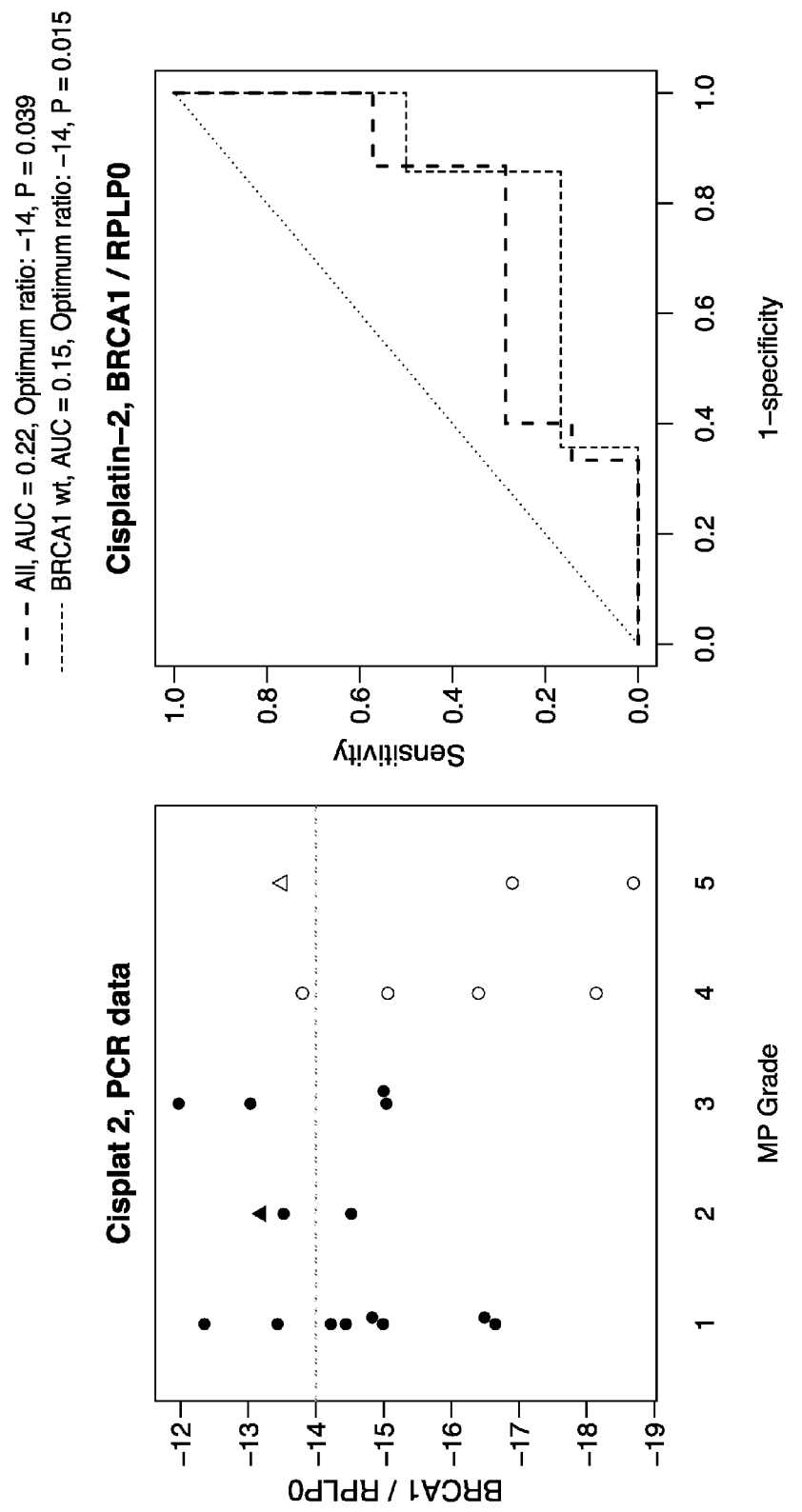
FIG. 17 shows the BRCA1/RPLP0 signature. BRCA1 is compared to a housekeeping gene, RPLP0. The optimum ratio here is −14 for all cases, on a log2 scale, which is approximately equivalent to $1/1600$, or 14 cycles on a PCR machine. This is a very large difference, but HK genes are expressed in very high numbers.
Figure 18:
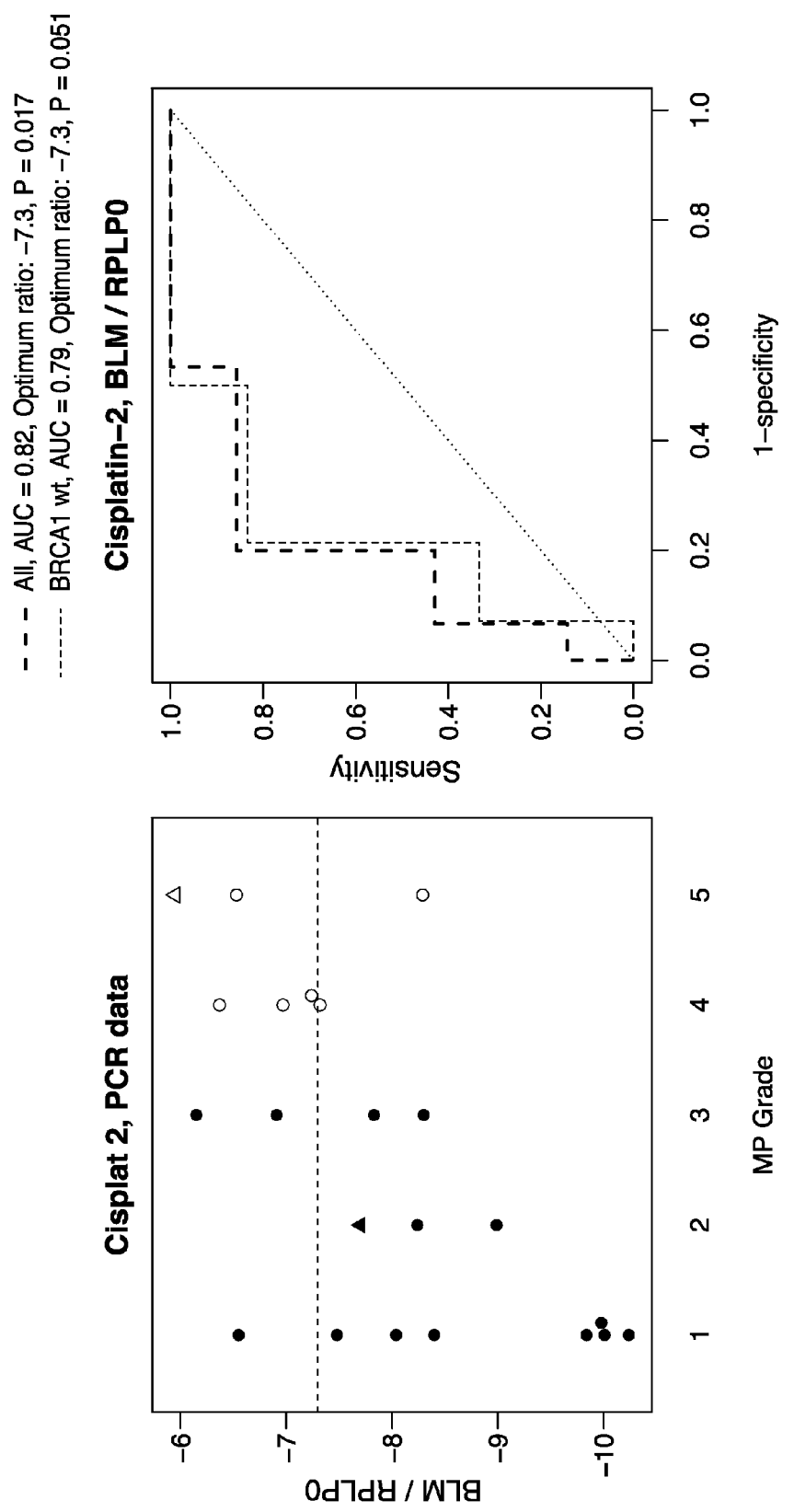
FIG. 18 shows BLM/RPLP0 signature. BLM is compared to a housekeeping gene, RPLP0 The optimum ratio is higher, and separation of sensitive/resistant cases is good.
Figure 20A:
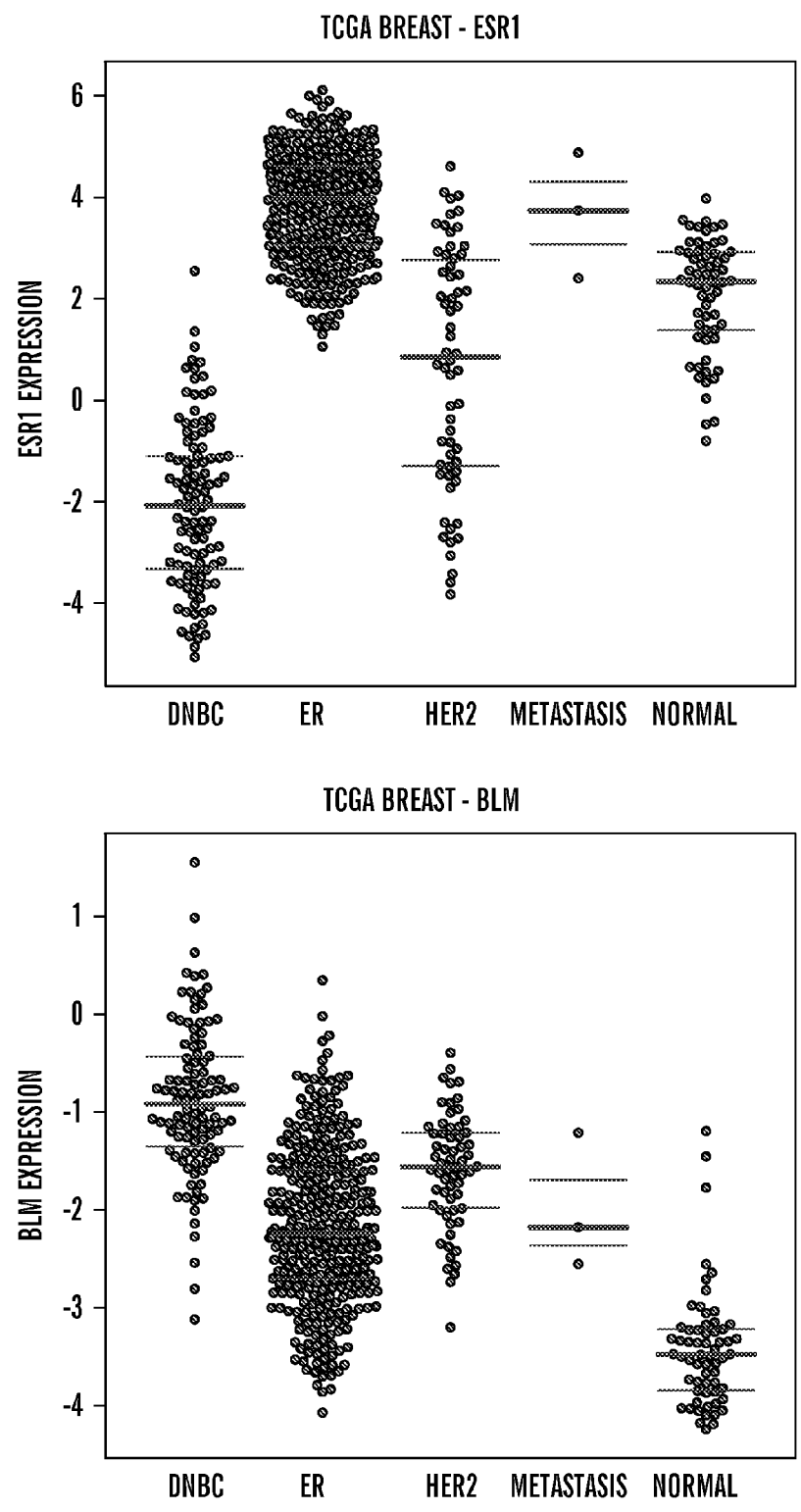
FIGS. 20A and 20B show how the expression of each of the three genes looks like in a large cohort of breast cancer patients from the TCGA, and how their ratios is to RPLP0 and BRCA1. These patients were not treated with platinum. This was focused on DNBC cases (ER/HER2 negative), and the normal breast samples. The ratio is much lower than using PCR data, yet there still appear to be a clear increase in some cases. The normal samples have lower BLM and BRCA1 expression, but that the ratio between these is inversed, with higher BRCA1 than BLM, probably reflecting the normal balance between these genes.
Figure 20A:
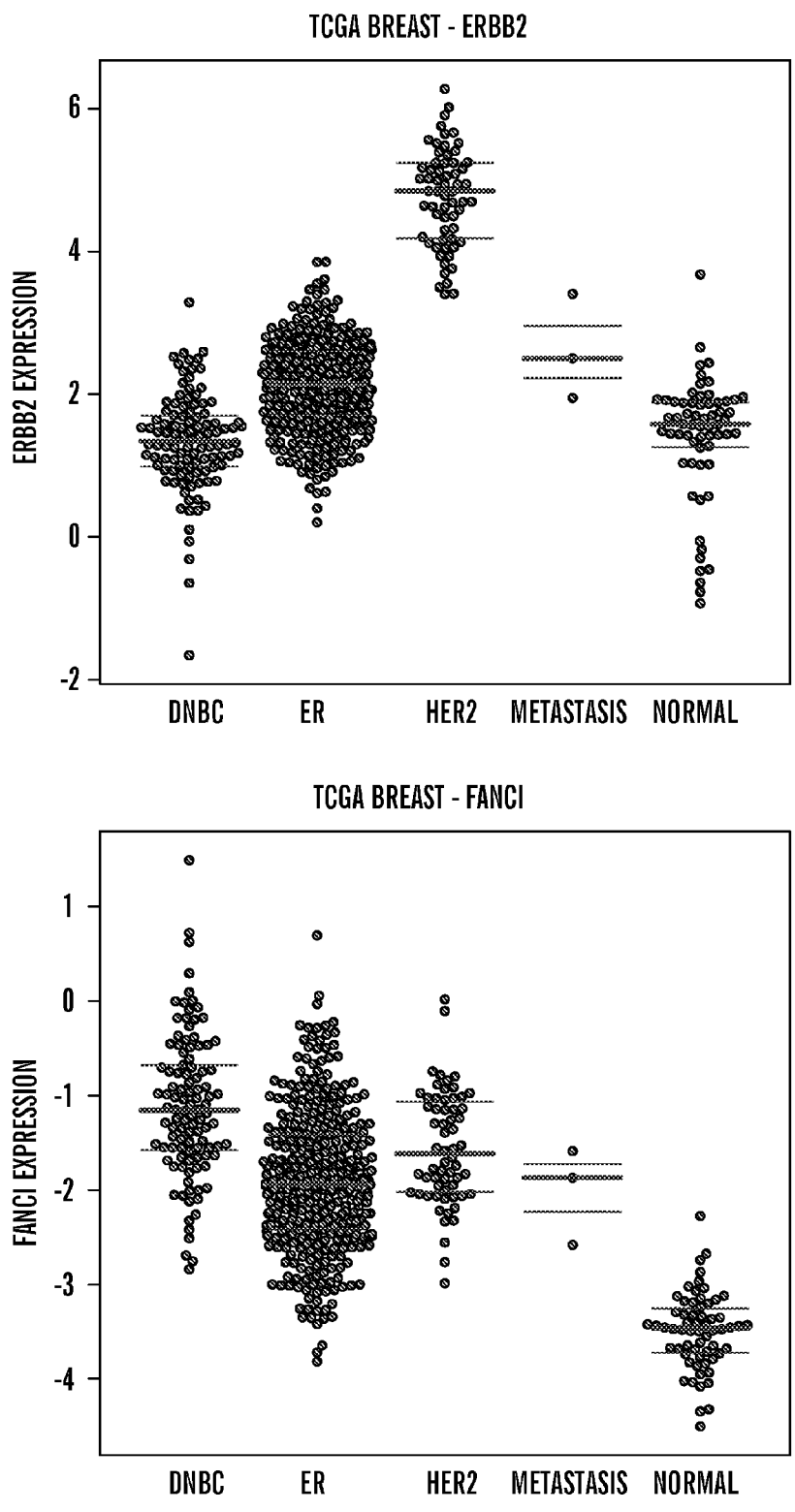
Figure 20A:
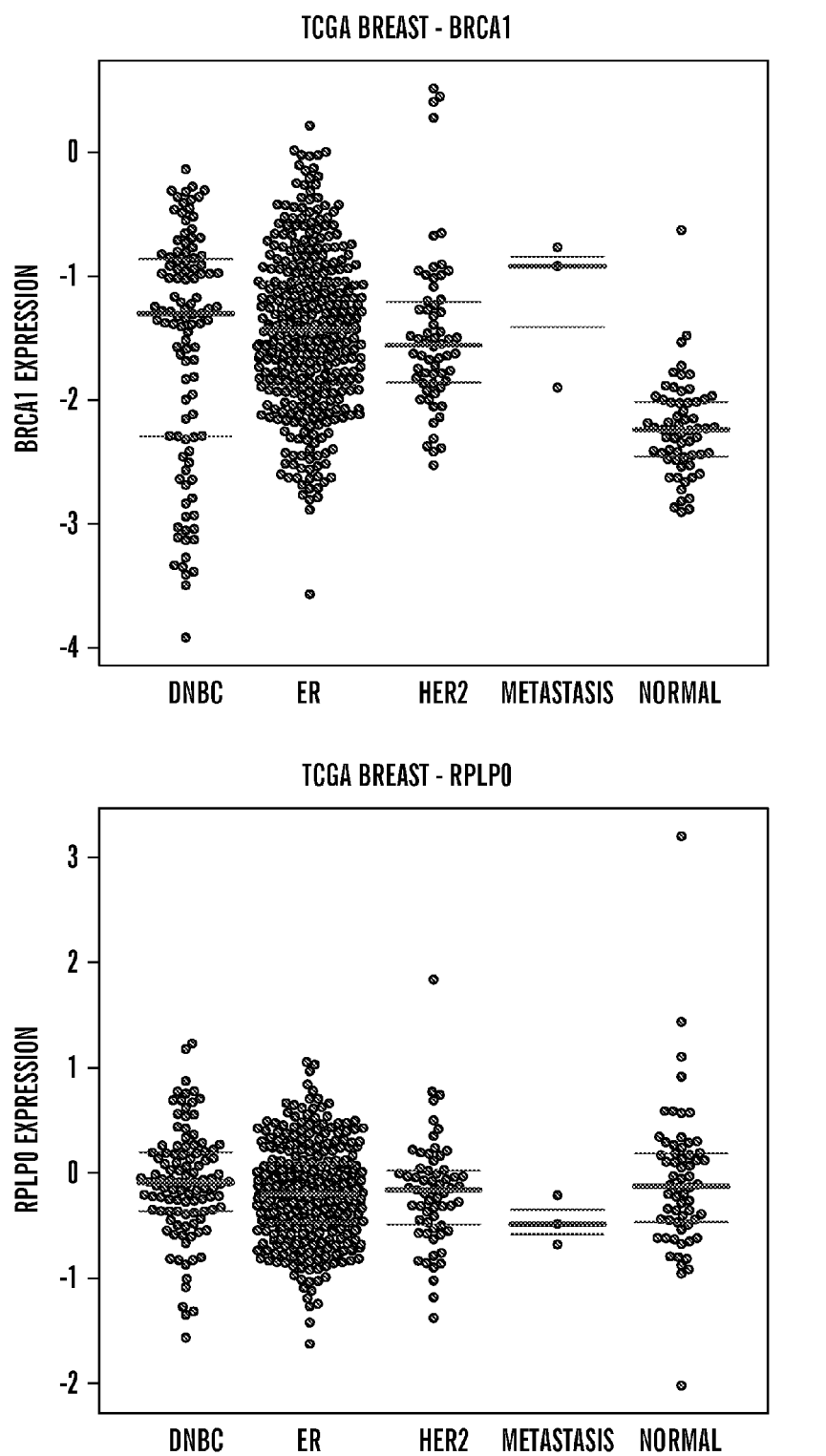
Figure 20B:
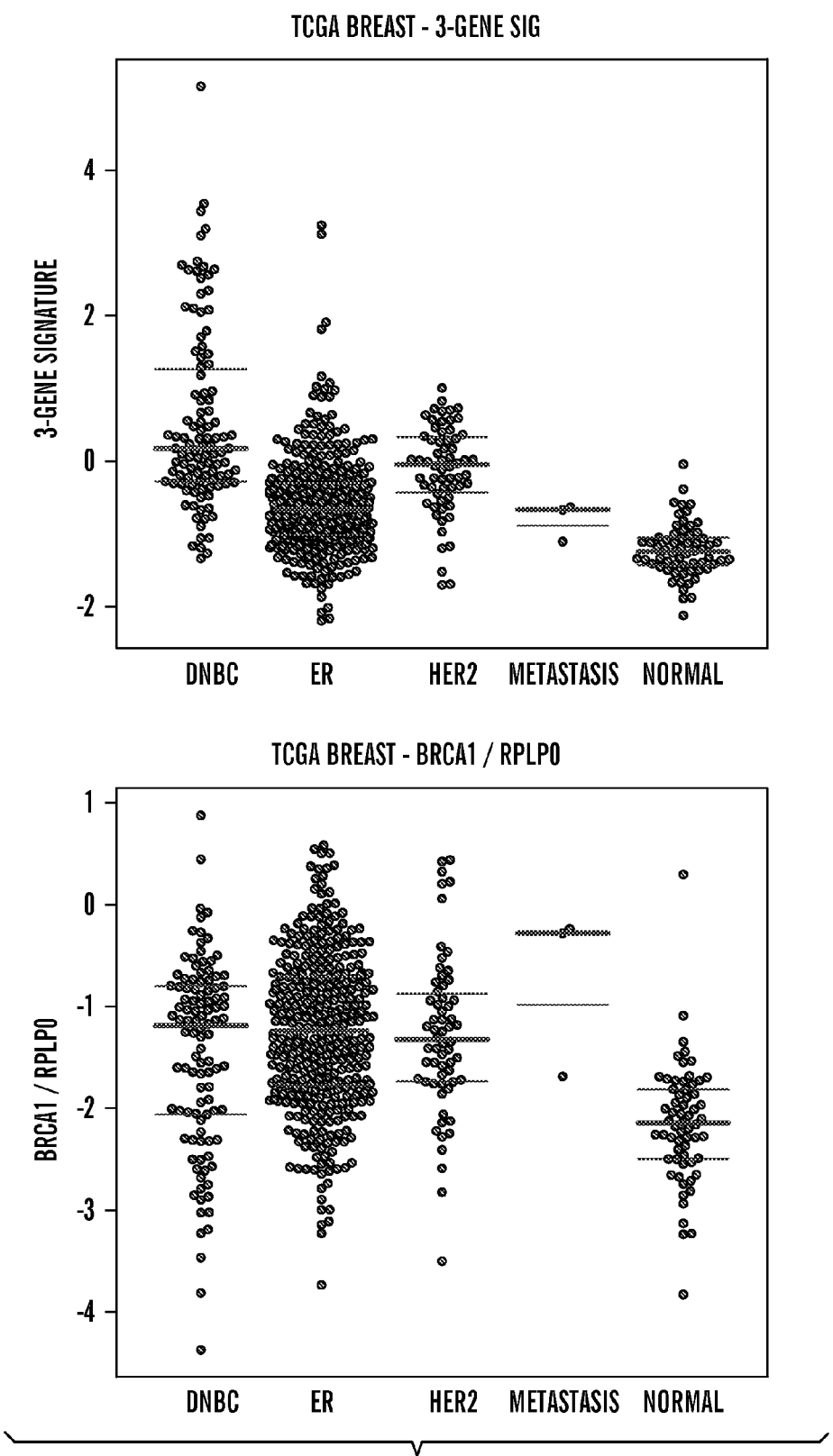
Figure 20B:
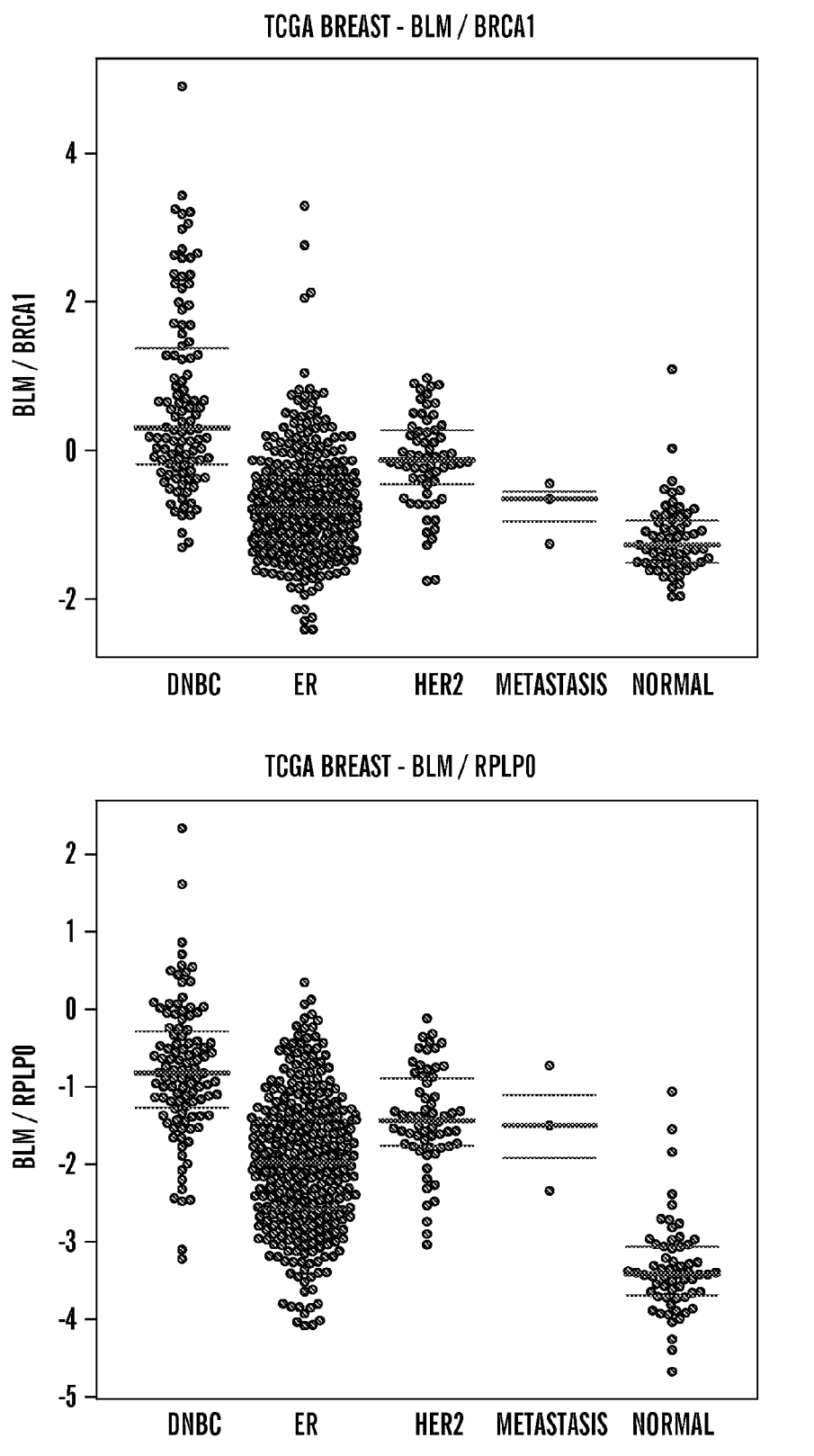
Figure 20B:
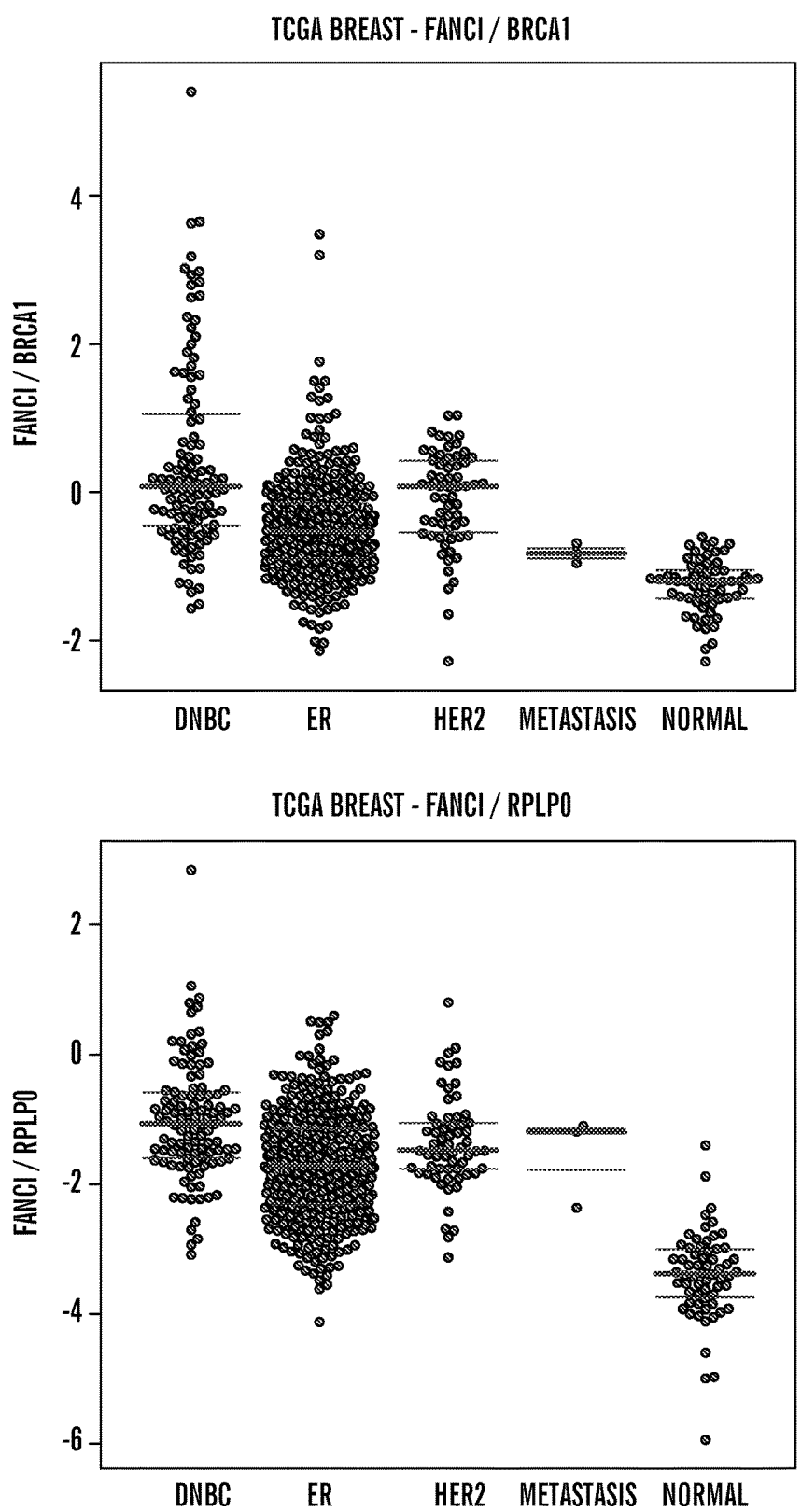

The functional modules of certain embodiments of the invention; for example, as depicted in FIG. 12, include for example, at a measuring module 40, a storage module 30, a comparison module 80, and an output module 110. The functional modules can be executed on one, or multiple, computers, or by using one, or multiple, computer networks. The measuring module has computer executable instructions to provide e.g., expression information in computer readable form.

The measuring module 40, can comprise any system for detecting the expression of BLM and/or FANCI, the 15Q26 copy number. Such systems can include DNA microarrays, RNA expression arrays, any ELISA detection system and/or any Western blotting detection system.

The information determined in the determination system can be read by the storage module 30. As used herein the "storage module" is intended to include any suitable computing or processing apparatus or other device configured or adapted for storing data or information. Examples of electronic apparatus suitable for use with the present invention include stand-alone computing apparatus, data telecommunications networks, including local area networks (LAN), wide area networks (WAN), Internet, Intranet, and Extranet, and local and distributed computer processing systems. Storage modules also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage module is adapted or configured for having recorded thereon expression level or protein level information. Such information may be provided in digital form that can be transmitted and read electronically, e.g., via the Internet, on diskette, via USB (universal serial bus) or via any other suitable mode of communication.

As used herein, "stored" refers to a process for encoding information on the storage module. Those skilled in the art can readily adopt any of the presently known methods for recording information on known media to generate manufactures comprising expression level information.

In one embodiment the reference data stored in the storage module to be read by the comparison module is e.g., expression data obtained from a population of non-cancer subjects, a population of cancer subjects or expression data obtained from the same subject at a prior time point using the measuring module 40.

The "comparison module" 80 can use a variety of available software programs and formats for the comparison operative to compare expression data determined in the measuring module to reference samples and/or stored reference data. In one embodiment, the comparison module is configured to use pattern recognition techniques to compare information from one or more entries to one or more reference data patterns. The comparison module may be configured using existing commercially-available or freely-available software for comparing patterns, and may be optimized for particular data comparisons that are conducted. The comparison module provides computer readable information related to normalized expression of BLM and/or FANCI, the 15Q26 copy number in an individual, efficacy of treatment in an individual, and/or method for treating an individual.

The comparison module, or any other module of the invention, may include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets. An advantage of such Intranets is that they allow easy communication with public domain databases residing on the World Wide Web (e.g., the GenBank or Swiss Pro World Wide Web site). Thus, in a particular preferred embodiment of the present invention, users can directly access data (via Hypertext links for example) residing on Internet databases using a HTML interface provided by Web browsers and Web servers.

The comparison module provides a computer readable comparison result that can be processed in computer readable form by predefined criteria, or criteria defined by a user, to provide a content-based in part on the comparison result that may be stored and output as requested by a user using an output module 110.

The content based on the comparison result, may be an expression value compared to a reference showing the susceptibility or nonsusceptibility of treatment with platinum-comprising therapy or anthracycline-comprising therapy.

In various embodiments of the invention, the content based on the comparison result is displayed on a computer monitor 120. In various embodiments of the invention, the content based on the comparison result is displayed through printable media 130. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content based on the comparison result. It should be understood that other modules of the invention can be adapted to have a web browser interface. Through the Web browser, a user may construct requests for retrieving data from the comparison module. Thus, the user will typically point and click to user interface elements such as buttons, pull down menus, scroll bars and the like conventionally employed in graphical user interfaces.

The present invention therefore provides for systems (and computer readable media for causing computer systems) to perform methods for selecting treatment of cancer in an individual.

Systems and computer readable media described herein are merely illustrative embodiments of the invention for detecting BLM and/or FANCI expression, or 15Q26 copy number in an individual, and are not intended to limit the scope of the invention. Variations of the systems and computer readable media described herein are possible and are intended to fall within the scope of the invention.

The modules of the machine, or those used in the computer readable medium, may assume numerous configurations. For example, function may be provided on a single machine or distributed over multiple machines.

In some cases, a computing system provided herein can include computer-executable instructions or a computer program (e.g., software) containing computer-executable instructions for formatting an output providing an indication BLM and/or FANCI expression, 15q26 copy number, or a likelihood that a cancer patient will respond to a particular cancer treatment regimen (e.g., a regimen as described above), or a combination of these items. In some cases, a computing system provided herein can include computer-executable instructions or a computer program (e.g., software) containing computer-executable instructions for determining a desired cancer treatment regimen for a particular patient based at least in part on increased expression of BLM and/or FANCI, or 15q26 copy number gain.

In some cases, a computing system provided herein can include a pre-processing device configured to process a sample (e.g., cancer cells) such that a SNP array-based assay or sequencing-based assay can be performed. Examples of pre-processing devices include, without limitation, devices configured to enrich cell populations for cancer cells as opposed to non-cancer cells, devices configured to lyse cells and/or extract genomic nucleic acid, and devices configured to enrich a sample for particular genomic DNA fragments.

The following numbered paragraphs provide some embodiments and aspects of the invention.

1. An assay for selecting a therapy for a subject having cancer, and optionally administering the therapy, the assay comprising:
    subjecting a sample comprising a cancer cell taken from the subject to an analysis for BLM and FANCI expression;
    comparing the BLM and FANCI expression to a reference value; and
    selecting a platinum-comprising cancer therapy for the subject when the BLM and FANCI expression is increased compared to the reference value based on the recognition that platinum-comprising cancer therapy is effective in subjects whose cancer has increased expression of BLM and FANCI, or selecting a non-platinum-comprising cancer therapy for the subject when the BLM and FANCI expression is not increased compared to the reference value based on the recognition that platinum-comprising cancer therapy is not effective in subjects whose cancer does not have increased BLM and FANCI expression compared to the reference value.
2. The assay of paragraph 1, further comprising:
    assaying the BRCA1 and/or BRCA2 status of the subject; and
    selecting the platinum-comprising cancer therapy for the subject when the subject is negative for BRCA1 and/or BRCA2 mutations, and the BLM and FANCI expression is increased compared to the reference value based on the recognition that platinum-comprising cancer therapy is effective in subjects whose cancer has increased expression of BLM and FANCI and who are negative for BRCA1 and/or BRCA2 mutations.
3. The assay of paragraph 1, the subject is known to be or is determined to be negative for BRCA1 and/or BRCA2 mutations.
4. The assay of paragraph 1, further comprising:
    assaying the estrogen receptor (ER), progesterone receptor (PgR), and HER2 receptor status of the subject's cancer; and
    selecting the platinum-comprising cancer therapy for the subject when the subject's cancer does not express a detectable quantity of ER, PgR, and HER2 receptor, and when the BLM and FANCI expression is increased compared to the reference value based on the recognition that platinum-comprising cancer therapy is effective in subjects whose cancer has increased expression of BLM and FANCI and whose cancer does not express a detectable quantity of ER, PgR, and HER2 receptor.
5. The assay of paragraph 1, wherein the subject's cancer or cancer cell is known to not or is determined to not express a detectable quantity of ER, PgR, and HER2 receptor.
6. The assay of paragraphs 1-5, further comprising administering the selected therapy to the subject.
7. The assay of any one of the paragraphs 1-6, wherein the cancer is selected from breast cancer, ovarian cancer and lung cancer.
8. The assay of paragraphs 1-6, wherein the reference value is BRCA1 expression in the sample and the BLM and/or FANCI expression is increased by at least two-fold compared to BRCA1 expression.
9. The assay of paragraphs 1-6, wherein the reference value is based on at least BRCA1 gene expression in the cancer cell.
10. The assay paragraphs 1-6, wherein the reference value is based on at least one housekeeping gene expression in the cancer cell.
11. A method for selecting platinum-comprising therapy for a subject having cancer, and optionally administering the platinum-comprising therapy, the method comprising:
    subjecting a sample comprising a cancer cell taken from the subject to an analysis for BLM and FANCI expression;
    detecting the BLM and FANCI expression in the sample compared to a reference value; and
    selecting a platinum-comprising cancer therapy for the subject when the BLM and FANCI expression compared to a reference value is increased based on the recognition that platinum-comprising cancer therapy is effective in patients whose cancer has increased BLM and FANCI expression compared to the reference value.
12. The method of paragraph 11, further comprising administering to the subject the platinum-comprising cancer therapy when the platinum-comprising cancer therapy is selected.

13. The method of paragraph 11, wherein the subject is known to be or is determined to be negative for BRCA1 and/or BRCA2 mutations.
14. The method of paragraph 11, wherein the subject's cancer or cancer cell is known to not or determined to not express a detectable quantity of ER, PgR, and HER2 receptor.
15. The method of any one of the paragraphs 11-14, wherein the cancer is selected from breast cancer, ovarian cancer and lung cancer.
16. The method of paragraph 11-15, wherein the reference value is BRCA1 expression in the sample, and the BLM and/or FANCI expression is increased by at least two-fold compared to BRCA1 expression.
17. The method of any one of the paragraphs 11-15, wherein the reference value is based on at least BRCA1 gene expression in the cancer cell.
18. The method of any one of the paragraphs 11-15, wherein the reference value is based on at least one housekeeping gene expression in the cancer cell.
19. The method of paragraph 18, wherein the housekeeping gene is selected from beta-actin, GAPDH, RPLP0, GUS, TFRC and any combination thereof.
20. The method of paragraph 19, wherein the housekeeping gene is RPLP0, and the BLM and/or FANCI expression is increased by at least six-fold.
21. A method for selecting a non-platinum-comprising therapy, and optionally administering the non-platinum-comprising therapy, for a subject having cancer comprising:
    subjecting a sample comprising a cancer cell taken from the subject to an analysis for BLM and FANCI expression;
    detecting the BLM and FANCI expression in the sample compared to a reference value; and
    selecting the non-platinum-comprising cancer therapy for the subject when the BLM and FANCI expression compared to the reference value is not increased based on the recognition that non-platinum-comprising cancer therapy is effective in patients whose cancer does not have increased gene expression of BLM and FANCI compared to the reference value.
22. The method of paragraph 21, further comprising administering to the subject the non-platinum-comprising cancer therapy when non-platinum-comprising cancer therapy is selected.
23. The method of any one of the paragraphs 21-22, wherein the cancer is selected from breast cancer, ovarian cancer and lung cancer.
24. The method of paragraph 21-23, wherein the reference value is BRCA1 expression in the sample, and the BLM and/or FANCI expression is increased by at least two-fold compared to BRCA1 expression.
25. The method of any one of the paragraphs 21-24, wherein the reference value is based on at least BRCA1 gene expression in the cancer cell.
26. The method of any one of the paragraphs 21-22, wherein the reference value is based on at least one housekeeping gene expression in the cancer cell.
27. An assay for selecting a therapy for a subject having cancer, comprising:
    subjecting a sample comprising a cancer cell taken from the subject to an analysis for BLM and FANCI expression;
    comparing the BLM and FANCI expression to a reference value; and
    selecting an anthracycline-comprising cancer therapy for the subject when the BLM and FANCI expression is increased compared to a reference value based on the recognition that anthracycline-comprising cancer therapy is effective in subjects whose cancer has increased expression of BLM and FANCI, or
    selecting a non-anthracycline-comprising cancer therapy for the subject when the BLM and FANCI expression is not increased compared to a reference value based on the recognition that anthracycline-comprising cancer therapy is not effective in subjects whose cancer does not have increased BLM expression compared to a reference value.
28. The assay of paragraph 27, wherein the reference value is BRCA1 expression in the sample, and the BLM and/or FANCI expression is increased by at least two-fold compared to BRCA1 expression.
29. A method for selecting an anthracycline-comprising cancer therapy for a subject having cancer and determined to be negative for BRCA1 and/or BRCA2 mutations, comprising:
    subjecting a sample comprising a cancer cell taken from the subject to an analysis for BLM and FANCI expression;
    comparing the BLM and FANCI expression to a reference value; and
    selecting the anthracycline-comprising cancer therapy for the subject when the BLM and FANCI expression compared to the reference value is increased based on the recognition that anthracycline-comprising cancer therapy is effective in patients whose cancer has increased expression of BLM and FANCI compared to the reference value.
30. The method of paragraph 29, wherein the reference value is BRCA1 expression in the sample, and the BLM and/or FANCI expression is increased by at least two-fold compared to BRCA1 expression.
31. A method of treating cancer in a human subject, comprising:
    detecting BLM and FANCI expression in a sample comprising a cancer cell taken from the human subject; and
    comparing the BLM and FANCI expression to a reference value; and
    administering a platinum-comprising cancer therapy to the human subject wherein an increase of BLM and FANCI expression compared to the reference value is detected.
32. The method of paragraph 31, wherein the human subject's cancer or cancer cell is known to not or is determined to not express detectable quantities of estrogen receptor (ER), progesterone receptor (PgR) and HER2 receptor.
33. The method of paragraph 31, wherein the cancer is selected from breast, ovarian, and lung cancers.
34. The method of paragraph 31-33, wherein the reference value is BRCA1 expression in the sample, and the BLM and/or FANCI expression is increased by at least two-fold compared to BRCA1 expression.
35. The method of any one of the paragraphs 31-33, wherein the reference value is based on BRCA1 gene expression in the cancer cell.
36. The method of any one of the paragraphs 31-33, wherein the reference value is based on a housekeeping gene expression in the cancer cell.

37. A method of treating cancer in a human subject, comprising:
  detecting BLM and FANCI expression in a sample comprising a cancer cell taken from the human subject; and
  comparing the BLM and FANCI expression to a reference value; and
  administering an anthracycline-comprising cancer therapy to the human subject wherein an increase of BLM and FANCI expression compared to the reference value is detected.
38. The method of paragraph 37, wherein the human subject's cancer or cancer cell is known to not or is determined to not to express detectable quantities of estrogen receptor (ER), progesterone receptor (PgR) and HER2 receptor.
39. The method of paragraph 37, wherein the cancer is selected from breast, ovarian, and lung cancers.
40. The method of paragraph 37-39, wherein the reference value is BRCA1 expression in the sample, and the BLM and/or FANCI expression is increased by at least two-fold compared to BRCA1 expression.
41. The method of any one of the paragraphs 37-39, wherein the reference value is based on BRCA1 gene expression in the cancer cell.
42. The method of any one of the paragraphs 37-39, wherein the reference value is based on a housekeeping gene expression in the cancer cell.
43. A method for assessing responsiveness of a cancer cell to cancer therapy, comprising:
  assaying, in a cancer cell or mRNA derived therefrom, BLM and FANCI expression; and
  comparing said BLM and FANCI expression to a reference value, wherein the cancer cell is assessed as responsive to a platinum-comprising therapy if the BLM and FANCI expression is increased compared to the reference value, or wherein the cancer cell is assessed as poorly or not responsive to platinum-comprising cancer therapy cancer if the BLM and FANCI expression is not increased.
44. The method of paragraph 43, wherein the step of assaying comprises:
  contacting the cancer cell or mRNA derived therefrom with at least one detectably labeled probe capable of specifically binding to BLM mRNA, at least one detectably probe capable of specifically binding to FANCI, at least one detectably labeled probe capable of specifically binding to BRCA1 and/or at least one housekeeping gene; and
  measuring the expression of BLM and FANCI compared to the BRCA1 and/or the at least one housekeeping gene.
45. The method of paragraph 43-44, wherein the reference value is BRCA1 expression in the sample, and the BLM and/or FANCI expression is increased by at least two-fold compared to BRCA1 expression.
46. A method of predicting a cancer patient's response to a cancer treatment regimen comprising platinum or anthracycline, comprising:
  determining, in a cancer cell from the cancer patient, BLM and FANCI expression; and
  correlating the expression to a reference value, wherein when the expression is increased the patient is predicted to respond well to a cancer treatment regimen comprising platinum or anthracycline.
47. The method of paragraph 46, wherein the reference value is BRCA1 expression in the sample, and the BLM and/or FANCI expression is increased by at least two-fold compared to BRCA1 expression.
48. A method of predicting a cancer patient's response to a cancer treatment regimen comprising platinum or anthracycline, comprising:
  determining, in a cancer cell or mRNA derived therefrom from said cancer patient, BLM and FANCI expression; and
  correlating the expression to a reference value, wherein when the expression is not increased the patient is predicted to respond poorly to a cancer treatment regimen comprising platinum or anthracycline.
49. The method of paragraph 48, wherein the reference value is BRCA1 expression in the sample, and the BLM and/or FANCI expression is increased by at least two-fold compared to BRCA1 expression.
50. A method of treating cancer, comprising:
  assaying, in a cancer cell from a cancer patient or mRNA obtained therefrom, the BLM and FANCI expression compared to a reference value; and
  administering to the cancer patient a cancer treatment regimen comprising platinum or anthracycline if the BLM and FANCI expression is increased compared to the reference value.
51. The method of paragraph 50, wherein the reference value is BRCA1 expression in the sample, and the BLM and/or FANCI expression is increased by at least two-fold compared to BRCA1 expression.
52. Use of platinum comprising cancer therapy for treating a cancer patient that has been determined to have a tumor comprising cancer cells wherein BLM and FANCI expression is increased compared to a reference value.
53. The use of paragraph 52, wherein the cancer patient has been determined to be negative for BRCA1 and/or BRCA2 mutations.
54. The use of paragraph 52, wherein the cancer patient's cancer or cancer cell is known to not or is determined to not express detectable quantities of estrogen receptor (ER), progesterone receptor (PgR) and HER2 receptor.
55. The use of paragraph 52-54, wherein the reference value is BRCA1 expression in the sample, and the BLM and/or FANCI expression is increased by at least two-fold compared to BRCA1 expression.
56. A system for determining responsiveness of a cancer cell to platinum-comprising therapy from a cancer cell of a cancer patient, comprising:
  a sample analyzer configured to produce a signal for the mRNA from each one of BLM and FANCI from a cancer cell sample of a cancer patient; and
  a computer sub-system programmed to calculate, based on the mRNA whether the signal is greater or not than a reference value.
57. The system of paragraph 56, wherein said computer sub-system is programmed to compare the mRNA to determine
  a likelihood of responsiveness of said cancer cell to platinum-comprising cancer therapy based on an algorithm that classifies the patient as likely to respond to a platinum-comprising therapy if the BLM and FANCI expression is increased and as unlikely to respond to the platinum-comprising therapy if the BLM and FANCI expression is not increased; or
  a likelihood of responsiveness of said cancer cell to anthracycline-comprising cancer therapy based on an algorithm that classifies the patient as likely to respond to a anthracycline-comprising therapy if the BLM and FANCI expression is increased and as unlikely to respond to the anthracycline-comprising therapy if the BLM and FANCI expression is not increased.
58. The system of paragraph 56-57, wherein the reference value is BRCA1 expression, and the BLM and/or FANCI expression is increased by at least two-fold compared to BRCA1 expression.
59. A computer program product embodied in a computer readable medium that, when executing on a computer, performs steps comprising:
    detecting the BLM and FANCI gene expression in sample comprising a cancer cell from a cancer patient; and
    comparing the BLM and FANCI expression to a reference value.
60. The computer program of paragraph 59, wherein the reference value is BRCA1 expression, and the BLM and/or FANCI expression is increased by at least two-fold compared to BRCA1 expression.
61. A diagnostic kit for detecting a likelihood of a cancer patient to respond to platinum- or anthracycline-comprising comprising cancer therapy, comprising:
    no more than 10 probes comprising a combination of detectably labeled probes or primers for BLM and FANCI, and optionally for BRCA1 and/or at least one housekeeping gene; and
    the computer program product of Paragraph 59.
62. Use of a plurality of oligonucleotides comprising no more than 10 oligonucleotides capable of hybridizing to BLM and FANCI, and optionally to BRCA1 and/or at least one housekeeping gene, in a diagnostic kit for determining an increased likelihood that a cancer patient will respond to cancer treatment regimen comprising a platinum and/or anthracycline.
63. The use, method or assay of any one of the preceding paragraphs, wherein said anthracycline is epirubincin or doxorubicin.
64. The use, method or assay of any one of the preceding paragraphs, wherein said platinum comprising cancer therapy comprises cisplatinum or cis-diamminedichloroplatinum, phenanthriplatin, carboplatin, oxaliplatin, or a platinum complex that is activated by ultraviolet A light.
65. An assay for selecting a therapy for a subject having cancer, and optionally administering the therapy, the assay comprising:
    assaying a sample comprising a cancer cell taken from the subject for a chromosome 15q26 copy number;
    comparing the chromosome 15q26 copy number to a reference value; and
    selecting a platinum-comprising cancer therapy for the subject if there is a chromosome 15q26 copy number gain compared to the reference value, or selecting a non-platinum-comprising cancer therapy for the subject if there is not a chromosome 15q26 copy number gain, or if there is a chromosome 15q26 copy number loss.
66. The assay of paragraph 65, further comprising:
    assaying the BRCA1 and/or BRCA2 status of the subject; and
    selecting the platinum-comprising cancer therapy for the subject when the subject is negative for BRCA1 and/or BRCA2 mutations, and there is a chromosome 15q26 copy number gain based on the recognition that platinum-comprising cancer therapy is effective in subjects who have a chromosome 15q26 copy number gain who are negative for BRCA1 and/or BRCA2 mutations.
67. The assay of paragraph 65, the subject is known to be or is determined to be negative for BRCA1 and/or BRCA2 mutations.
68. The assay of paragraph 65, further comprising:
    assaying the estrogen receptor (ER), progesterone receptor (PgR), and HER2 receptor status of the subject's cancer; and
    selecting the platinum-comprising cancer therapy for the subject when the subject's cancer does not express a detectable quantity of ER, PgR, and HER2 receptor, and when there is a chromosome 15q26 copy number gain based on the recognition that platinum-comprising cancer therapy is effective in subjects who have a chromosome 15q26 copy number gain and whose cancer does not express a detectable quantity of ER, PgR, and HER2 receptor.
69. The assay of paragraph 65, wherein the subject's cancer or cancer cell is known to not or is determined to not express a detectable quantity of ER, PgR, and HER2 receptor.
70. The assay of paragraphs 65-69, further comprising administering the selected therapy to the subject.
71. The assay of paragraphs 65-71, wherein the cancer is selected from breast cancer, ovarian cancer and lung cancer.
72. The assay of paragraphs 65-71, wherein the reference value is chromosome 15 centromere copy number in the sample.
73. An assay for selecting a therapy for a subject having cancer, and optionally administering the therapy, the assay comprising:
    assaying a sample comprising a cancer cell taken from the subject for a chromosome 15q26 copy number;
    comparing the chromosome 15q26 copy number to a reference value; and
    selecting an anthracycline-comprising cancer therapy for the subject if there is a chromosome 15q26 copy number gain compared to the reference value, or selecting a non-anthracycline-comprising cancer therapy for the subject if there is not a chromosome 15q26 copy number gain, or if there is a chromosome 15q26 copy number loss.
74. The assay of paragraph 73, further comprising:
    assaying the BRCA1 and/or BRCA2 status of the subject; and
    selecting the anthracycline-comprising cancer therapy for the subject when the subject is negative for BRCA1 and/or BRCA2 mutations, and there is a chromosome 15q26 copy number gain based on the recognition that anthracycline-comprising cancer therapy is effective in subjects who have a chromosome 15q26 copy number gain who are negative for BRCA1 and/or BRCA2 mutations.
75. The assay of paragraph 73, the subject is known to be or is determined to be negative for BRCA1 and/or BRCA2 mutations.
76. The assay of paragraph 73, further comprising:
    assaying the estrogen receptor (ER), progesterone receptor (PgR), and HER2 receptor status of the subject's cancer; and
    selecting the anthracycline-comprising cancer therapy for the subject when the subject's cancer does not express a detectable quantity of ER, PgR, and HER2 receptor, and when there is a chromosome 15q26 copy number gain based on the recognition that anthracycline-comprising cancer therapy is effective in subjects who have a chromosome 15q26 copy number gain and whose cancer does not express a detectable quantity of ER, PgR, and HER2 receptor.

77. The assay of paragraph 73, wherein the subject's cancer or cancer cell is known to not or is determined to not express a detectable quantity of ER, PgR, and HER2 receptor.

78. The assay of paragraphs 73-77, further comprising administering the selected therapy to the subject.

79. The assay of paragraphs 73-78, wherein the cancer is selected from breast cancer, ovarian cancer and lung cancer.

80. The assay of paragraphs 73-79, wherein the reference value is chromosome 15 centromere copy number in the sample.

81. A method of treating cancer in a human subject, comprising:
    detecting a chromosome 15q26 copy number in a sample comprising a cancer cell taken from the subject;
    comparing the chromosome 15q26 copy number to a reference value; and
    administering an platinum-comprising cancer therapy for the subject if there is a chromosome 15q26 copy number gain compared to the reference value, or administering a non-platinum-comprising cancer therapy for the subject if there is not a chromosome 15q26 copy number gain, or if there is a chromosome 15q26 copy number loss.

82. The method of paragraphs 81, wherein the cancer is selected from breast cancer, ovarian cancer and lung cancer.

83. The method of paragraphs 81-82, wherein the reference value is chromosome 15 centromere copy number in the sample.

84. The method of paragraph 81-83, wherein the subject's cancer is known to not express a detectable quantity of ER, PgR, and HER2 receptor.

85. A method of treating cancer in a human subject, comprising:
    detecting a chromosome 15q26 copy number in a sample comprising a cancer cell taken from the subject;
    comparing the chromosome 15q26 copy number to a reference value; and
    administering an anthracycline-comprising cancer therapy for the subject if there is a chromosome 15q26 copy number gain compared to the reference value, or administering a non-anthracycline-comprising cancer therapy for the subject if there is not a chromosome 15q26 copy number gain, or if there is a chromosome 15q26 copy number loss.

86. The method of paragraphs 85, wherein the cancer is selected from breast cancer, ovarian cancer and lung cancer.

87. The method of paragraphs 85-86, wherein the reference value is chromosome 15 centromere copy number in the sample.

88. The method of paragraph 85-88, wherein the subject's cancer or cancer cell is known to not or is determined to not express a detectable quantity of ER, PgR, and HER2 receptor.

89. A method for assessing responsiveness of a cancer cell to a cancer therapy, and optionally administering the cancer therapy, comprising:
    assaying a sample comprising a cancer cell taken from the subject for a chromosome 15q26 copy number;
    and comparing the chromosome 15q26 copy number to a reference value, wherein the cancer cell is assessed as responsive to a platinum-comprising therapy if there is a chromosome 15q26 copy number gain compared to the reference value, or wherein the cancer cell is assessed as poorly or not responsive to platinum-comprising cancer therapy cancer if there is not a chromosome 15q26 copy number gain or if there is a chromosome 15q26 copy number loss.

90. The method of paragraph 89, wherein the reference value is copy number of chromosome 15.

91. The method of paragraph 89, wherein the cancer is selected from breast cancer, ovarian cancer and lung cancer.

92. The method of paragraph 89, further comprising administering the platinum-comprising therapy if there is a chromosome 15q26 copy number gain.

93. A method of predicting a cancer patient's response to a cancer treatment regimen comprising platinum or anthracycline, comprising:
    determining, in a cancer cell from the cancer patient, chromosome 15q26 copy number; and
    correlating the chromosome 15q26 copy number to a reference value,
    wherein when there is a chromosome 15q26 copy number gain, the patient is predicted to respond well to a cancer treatment comprising platinum or anthracycline, or wherein when there is not a chromosome 15q26 copy number gain or a chromosome 15q26 copy number loss, the patient is predicted respond poorly to a cancer treatment comprising platinum or anthracycline.

94. The method of paragraph 93, wherein the reference value is chromosome 15 centromere copy number in the sample.

95. Use of platinum comprising cancer therapy for treating a cancer patient that has been determined to have a tumor comprising cancer cells wherein a chromosome 15q26 copy gain is detected compared to a reference value.

96. The use of paragraph 95, wherein the cancer patient is known to be or is determined to be negative for BRCA1 and/or BRCA2 mutations.

97. The use of paragraph 95, wherein the cancer patient's cancer or cancer cell is known to not or is determined to not express detectable quantities of estrogen receptor (ER), progesterone receptor (PgR) and HER2 receptor.

98. The use of paragraph 95-97, wherein the reference value is chromosome 15 centromere copy number in the sample.

99. A system for determining responsiveness of a cancer cell to platinum-comprising therapy from a cancer cell of a cancer patient, comprising:
    a sample analyzer configured to produce a signal for chromosome 15q26 copy number from a cancer cell sample of a cancer patient; and
    a computer sub-system programmed to calculate, based on the mRNA whether the signal is greater or not than a reference value.

100. The system of paragraph 99, wherein said computer sub-system is programmed to compare the mRNA to determine
    a likelihood of responsiveness of said cancer cell to platinum-comprising cancer therapy and/or or a anthracycline-comprising cancer therapy based on an algorithm that classifies the patient as likely to respond to a platinum-comprising therapy if there is a chromosome 15q26 copy number gain and as unlikely to respond to the platinum-comprising therapy if there is not a chromosome 15q26 copy number gain or if there is a chromosome 15q26 copy number loss.

101. The system of paragraph 99-100, wherein the reference value is chromosome 15 centromere copy number in the sample.

102. A computer program product embodied in a computer readable medium that, when executing on a computer, performs steps comprising:
detecting chromosome 15q26 copy number in sample comprising a cancer cell from a cancer patient; and
comparing the chromosome 15q26 copy number to a reference value.

103. The computer program of paragraph 102, wherein the reference value is chromosome 15 centromere copy number in the sample.

104. A diagnostic kit for detecting a likelihood of a cancer patient to respond to platinum- or anthracycline-comprising cancer therapy, comprising:
no more than 10 probes comprising a combination of detectably labeled probes or primers for chromosome 15q26, and optionally for chromosome 15 centromere; and
the computer program product of Paragraph 102.

105. Use of a plurality of oligonucleotides comprising no more than 10 oligonucleotides capable of hybridizing to chromosome 15q26, and optionally for chromosome 15 centromere, in a diagnostic kit for determining an increased likelihood that a cancer patient will respond to cancer treatment regimen comprising a platinum and/or anthracycline.

106. The use, method or assay of paragraphs 65-105, wherein said anthracycline is epirubincin or doxorubicin.

107. The use, method or assay paragraphs 65-105, wherein said platinum comprising cancer therapy comprises cisplatinum or cis-diamminedichloroplatinum, phenanthriplatin, carboplatin, oxaliplatin, or a platinum complex that is activated by ultraviolet A light.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

EXAMPLE 1

Two clinical trials with cisplatin given to women with triple negative breast cancer were evaluated.

Cisplatin-1 (DFHCC 04-183; Silver et al., JCO 2010): 28 TNBC patients received neoadjuvant cisplatin as single agent. 10 (36%) achieved at least 90% reduction in tumor size. Good quality RNA and DNA were acquired from 21 tumors. Copy number and gene expression were assayed using AFFYMETRIX arrays.

Cisplatin-2 (DFHCC 06-202; Ryan et al., JCO 2009): 51 TNBC patients received neoadjuvant cisplatin in combination with the angiogenesis inhibitor bevacizumab. 44 patients completed therapy. 17 (39%) achieved at least 90% reduction in tumor size. Frozen DNA samples were acquired from 24 tumors, mRNA from 21. Copy number and gene expression assayed using AFFYMETRIX arrays.

EXAMPLE 2

Figure 2:
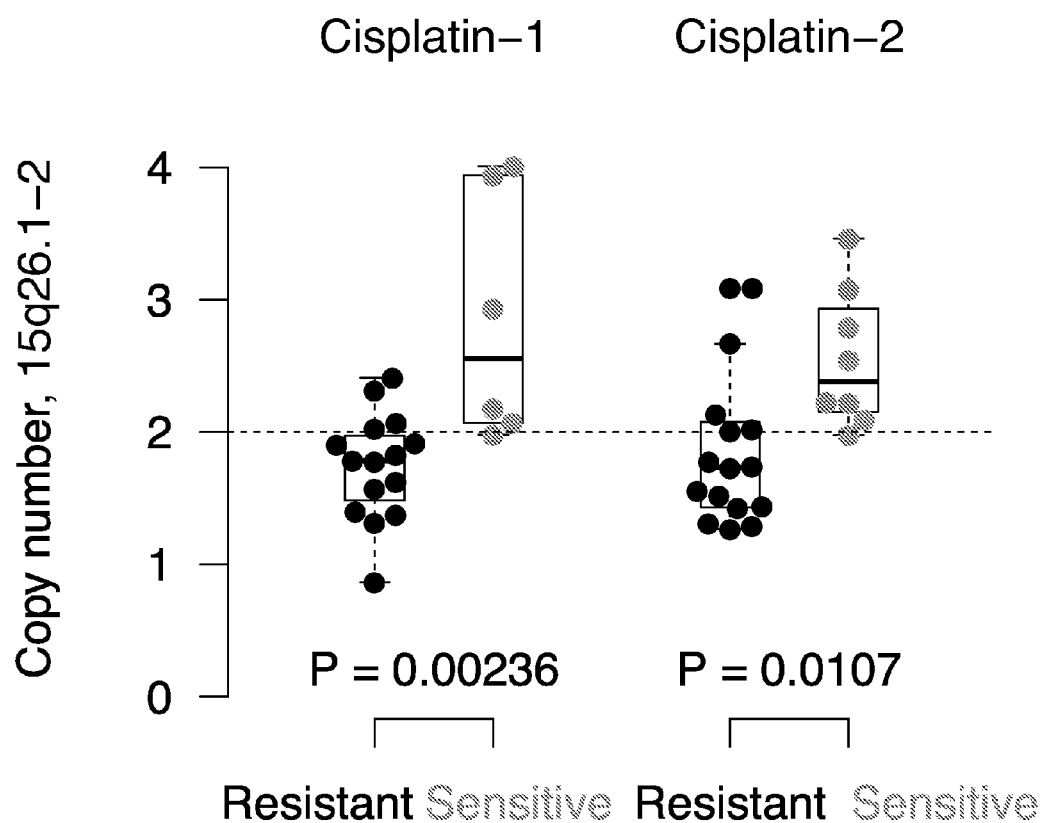
FIG. 2 shows a 10 MB region with 59 genes on chr. 15q26.1-2 showed significant gain in sensitive samples.
Figure 3:
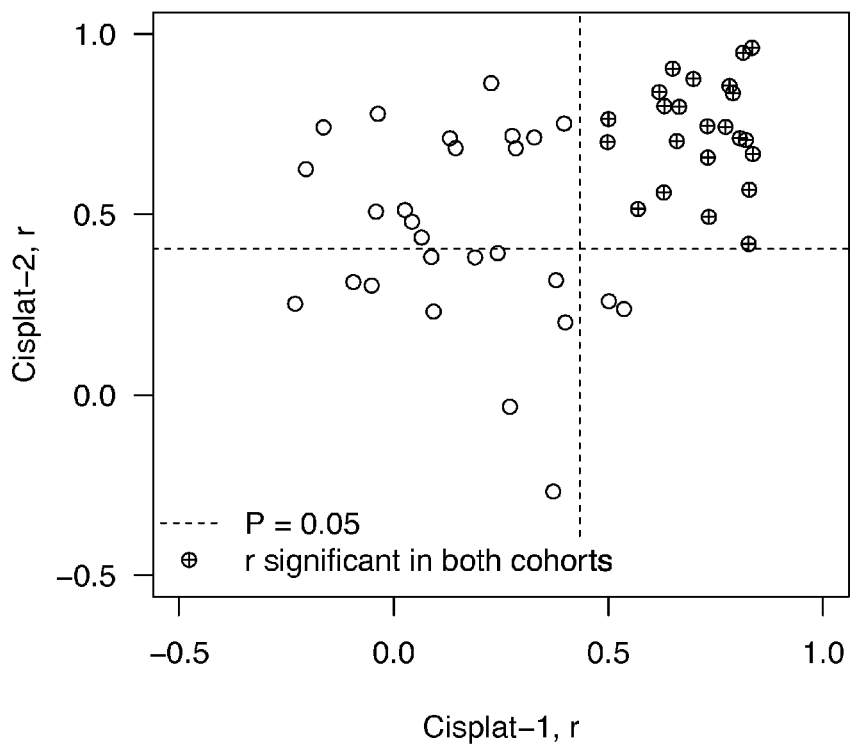
FIG. 3 shows correlation between copy number and mRNA expression, Genes on 15q26.1-2. 23 genes show significant correlation.

In order to find regions or genes where gain or loss were significantly associated with sensitivity of resistance cisplatin, ~40,000 SNP probes were used in Cisplatin-1 trial and ~330,000 SNP probes were used in Cisplatin-2 trial to determine sensitivity and resistance. GISTIC identified chromosomal regions that were significantly enriched in either group. Gene copy number comparison showed that genes significantly gained or lost between sensitive and resistant cases, in both cohorts. Comparison to gene expression showed overlap with genes showing differential expression between sensitive and resistant cancers. See e.g., FIGS. 1-3.

EXAMPLE 3

Figure 4:
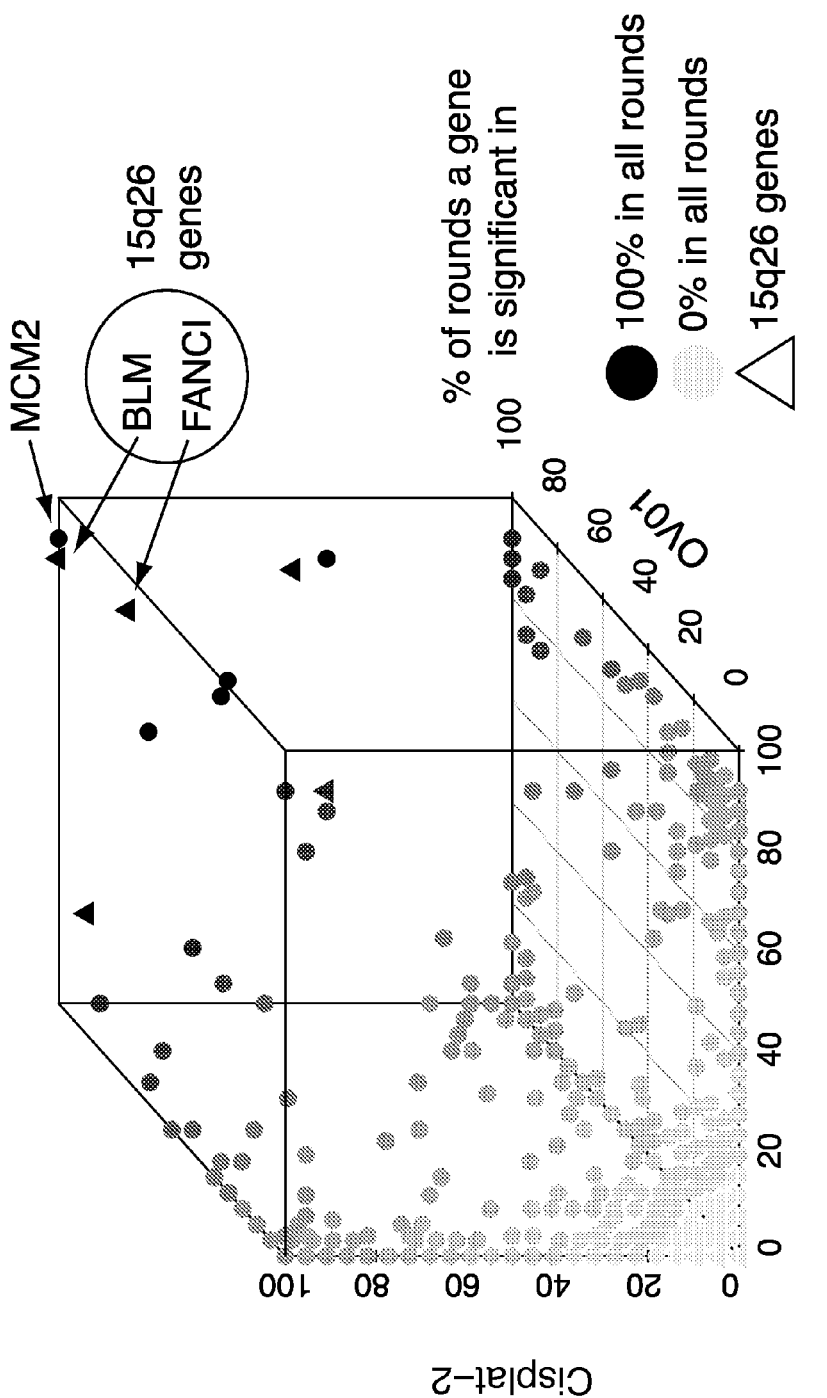
FIG. 4 depicts leave-one-out analysis of gene expression data.
Figure 5A:
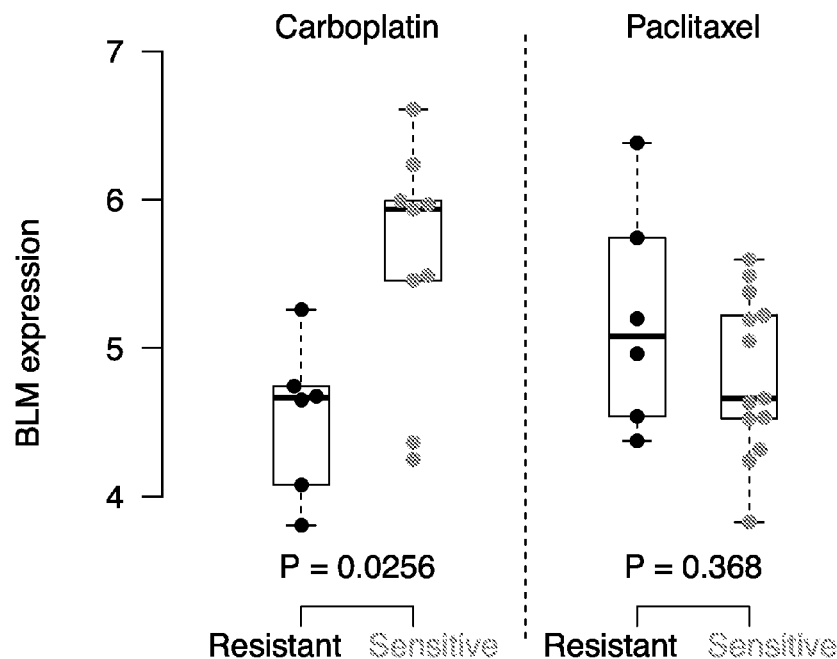
FIG. 5 shows that expression of BLM and FANCI is only associated with response to carboplatin, but not paclitaxel in OV01. (A) BLM expression; (B) FANCI Expression. Ahmed et al., Cancer Cell 2007.
Figure 5B:
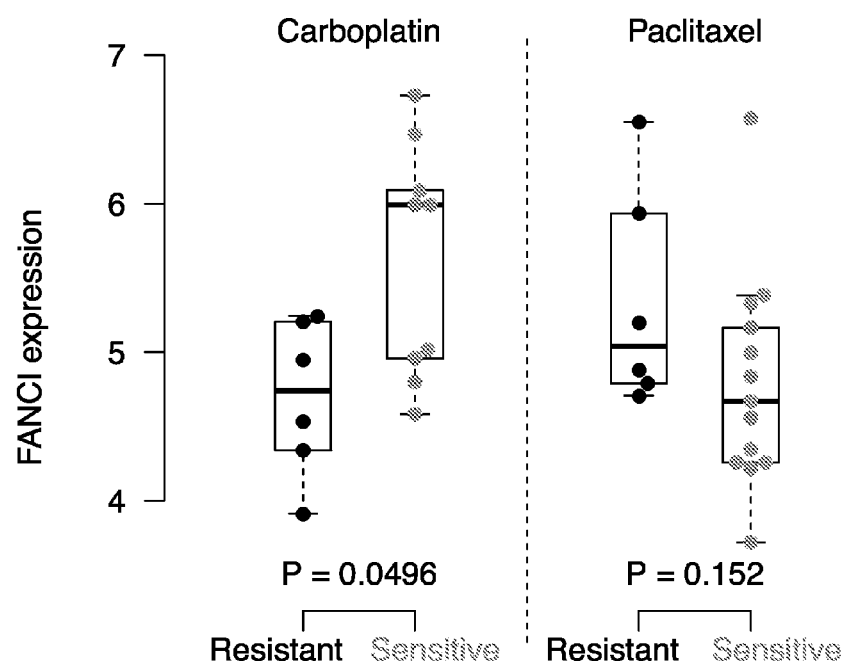

In a comparison to gene expression data, the inventors found genes that show both significant gain and higher expression in sensitive sample. In Cisplatin-1 trial, there were 21 cases; Cisplatin-2 trial, there were 21 cases. In an ovarian cancer trial (OV-01 trial; Ahmed et al., Cancer Cell 2007), the two arm carboplatinum had 15 cases and paclitaxel had 19 cases. A leave-one-out analysis of the gene expression data was performed from both platinum breast cancer trials and the carboplatinum arm of OV01. See e.g., FIGS. 4-5.

EXAMPLE 4

Figure 6A:
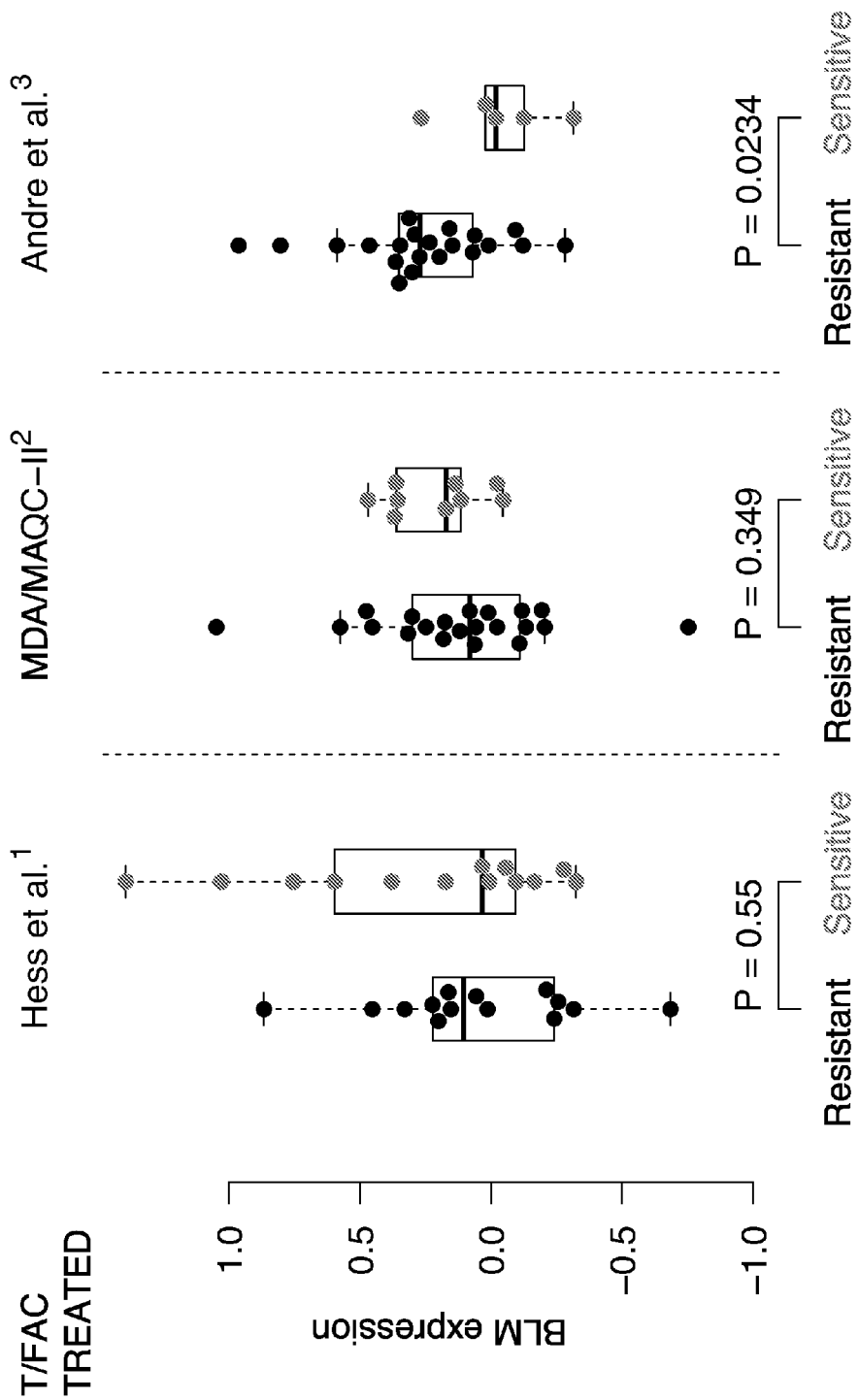
FIG. 6 depicts expression of BLM or FANCI is not associated with response to multi-agent chemotherapy regimens in triple negative breast cancer (TNBC). (A) BLM expression; (B) FANCI Expression. [1]Hess et al., JCO 2006; Popovici et al.,; [2]Breast Cancer Res 2010; [3]André et al., Clin Cancer Res 2009.
Figure 6B:
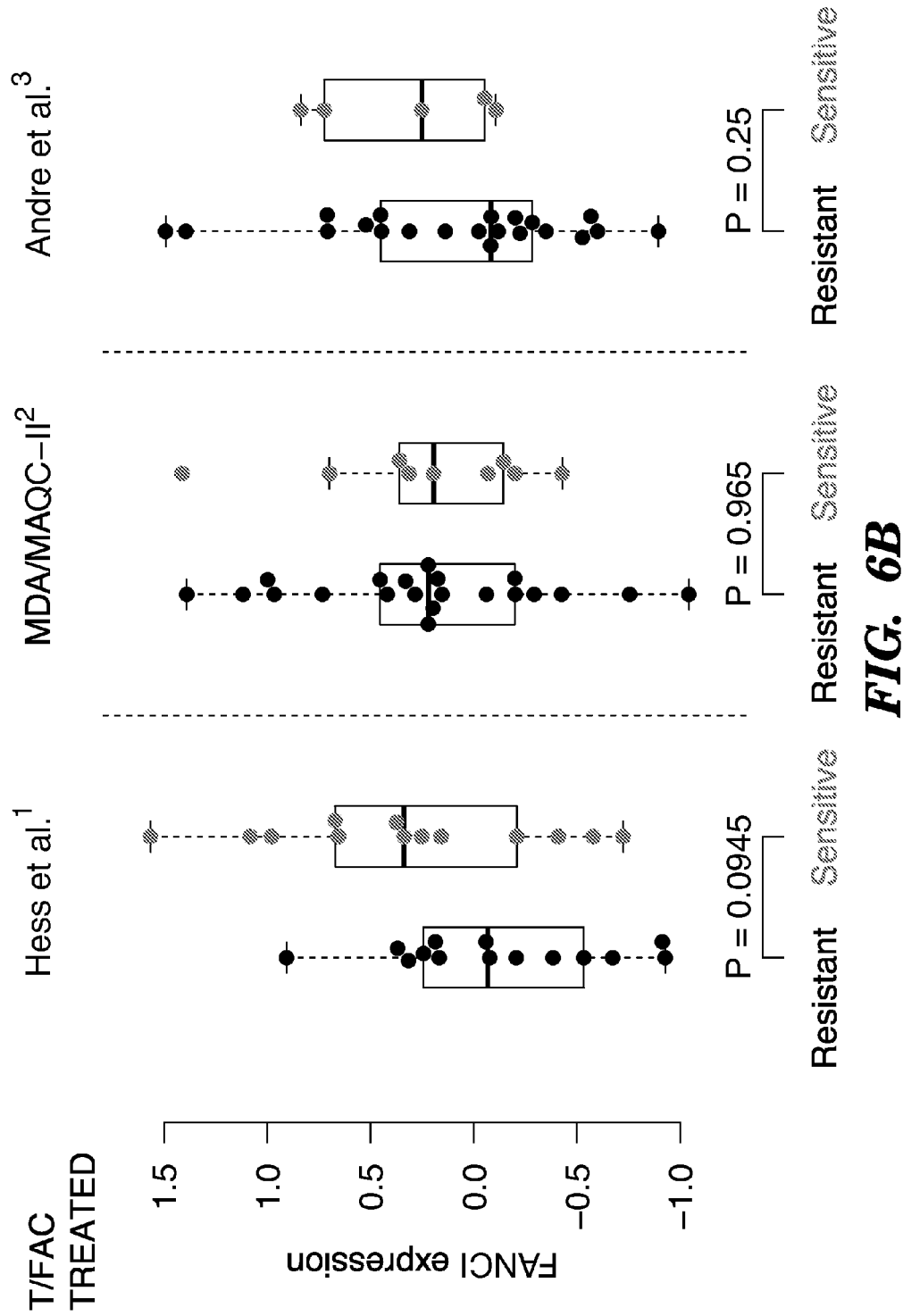

In evaluating Hess et al., JCO 2006; Popovici et al., Breast Cancer Res 2010; and André et al., Clin Cancer Res 2009, expression of BLM or FANCI is not found to be associated with response to multi-agent chemotherapy regimens in TNBC. See e.g., FIG. 6.

EXAMPLE 5

Figure 7:
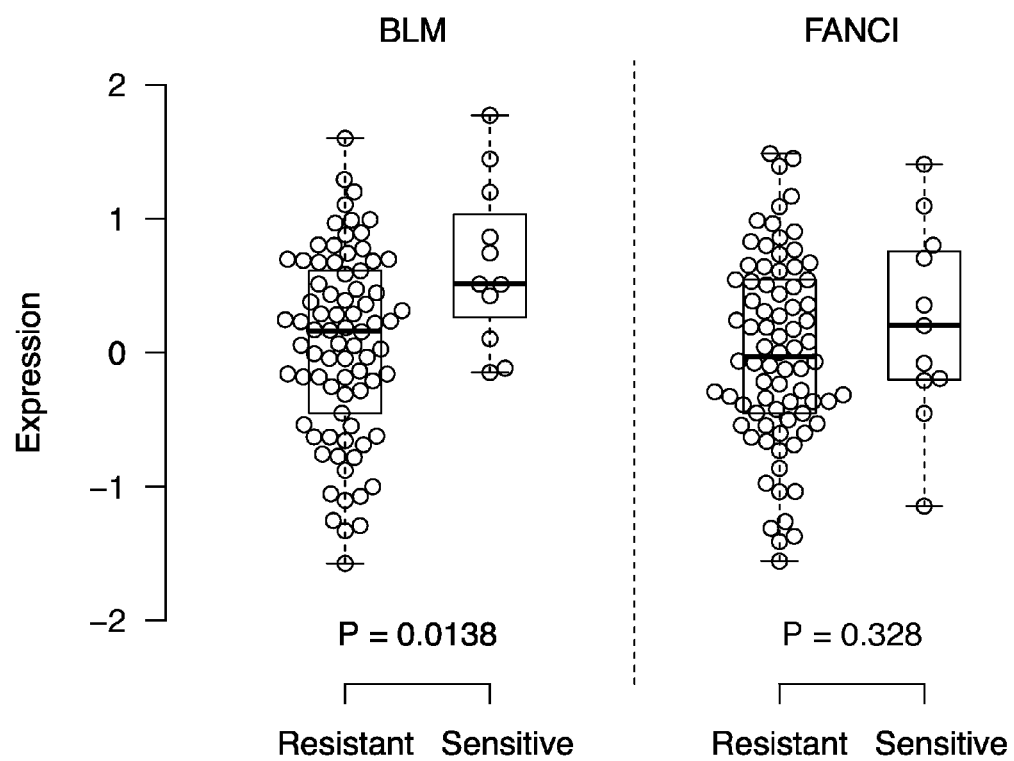
FIG. 7 shows that BLM is also associated with response to single agent epirubicin. TOP trial, single agent epirubicin in ER-negative breast cancer. [1]Desmedt et al., JCO 2011.
Figure 8:
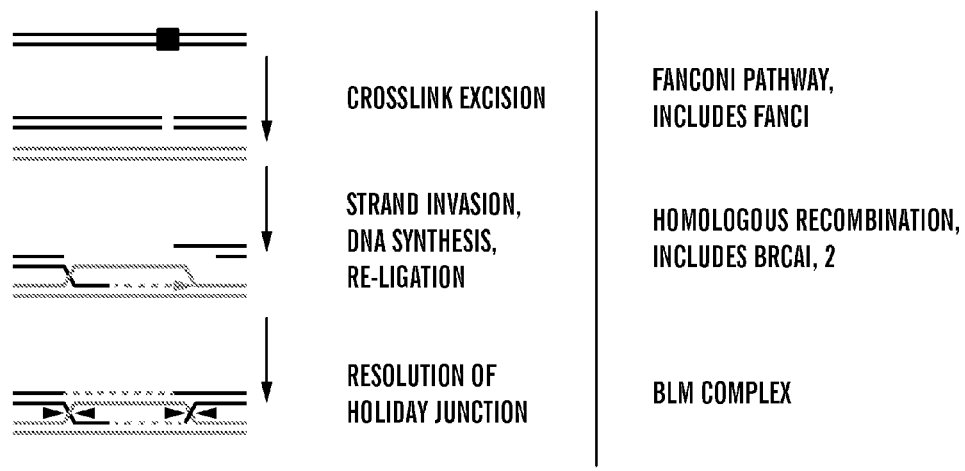
FIG. 8 depicts repair of cisplatin induced damage.
Figure 9:
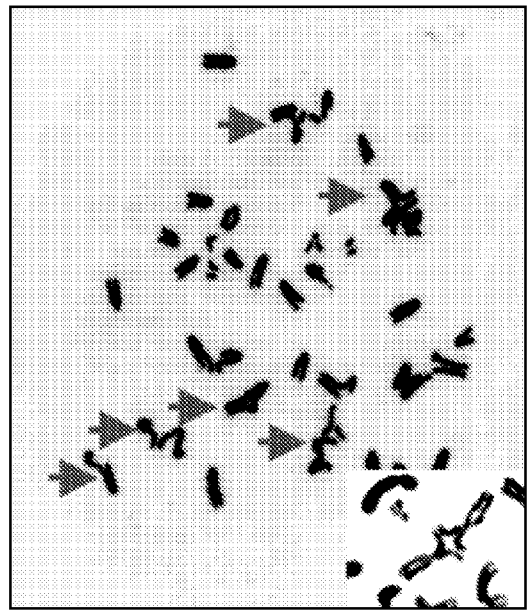
FIG. 9 depicts the metaphase spread, BRCA1 knock-out in MEFs. BRCA1 is an essential part of the homologous repair system. BRCA1 knock out cause high levels of quadrahelical chromosomes, which is a prime substrate for the Bloom helicase. Gain of BLM is a possible compensation mechanism for deficient HR. Silver DP et al, Cell 2007.

In evaluating Desmedt et al., JCO 2011, BLM is associated with response to single agent epirubicin. See e.g., FIG. 7.

EXAMPLE 6

Chromosome 15q26 Copy Number and Overexpression of BLM and FANCI Predict for Cisplatin Sensitivity To elucidate if particular genomic aberrations may affect cancer cells sensitivity to cisplatin, we compared the tumor DNA copy number profiles in sensitive versus resistant TN breast tumors in the two separate cisplatin clinical trials. We identified several sites of DNA copy number change in each trial, but only a short 15 megabase (MB) region on chromosome 15q26 was significantly different between responders and nonresponders in both trials. In addition to SNP profiles, we have analyzed the pretreatment tumor samples for both Cisplatin1 and Cisplatin2 for mRNA expression profiles on Affymetrix microarrays. In addition, gene expression array data was publically available from the carboplatin arm of a previously published two-arm trial of carboplatin and paclitaxel in serous ovarian cancer[31]. To determine if any specific genes were consistently differentially expressed in platinum sensitive compared to resistant tumors, we performed a leave-one-out analysis in each trial, where we in each round compared the sensitive to the resistant tumors, and scored how many genes showed a significant association. We found that only 3 genes were consistently significantly different in all three platinum-based trials: MCM2, BLM, and FANCI. Interestingly, FANCI and BLM are both located on 15q26.1 and the proteins have been shown to localize to sites of DNA damage. This shows that using two different methods measuring two different biomolecules, high levels of BLM and FANCI DNA and mRNA is associated with greater sensitivity to platinum-based chemotherapy.

To investigate if higher expression of BLM and FANCI were specifically associated with platinum chemotherapy response, we analyzed the gene expression in the paclitaxel arm of the ovarian trial[31], and across the TN breast cancer subset of three neoadjuvant cohorts that received taxane-containing combination chemotherapy[32-34].

In the ovarian paclitaxel trial and in the TN subset of the taxane-containing multidrug trials there was no association between either BLM or FANCI and therapy response. These data suggests that high expression of BLM and FANCI are possibly specifically associated with sensitivity to DNA damaging agents like the platinum salts, but not with response to chemotherapeutics that alter microtubules such as taxanes.

Figure 10:
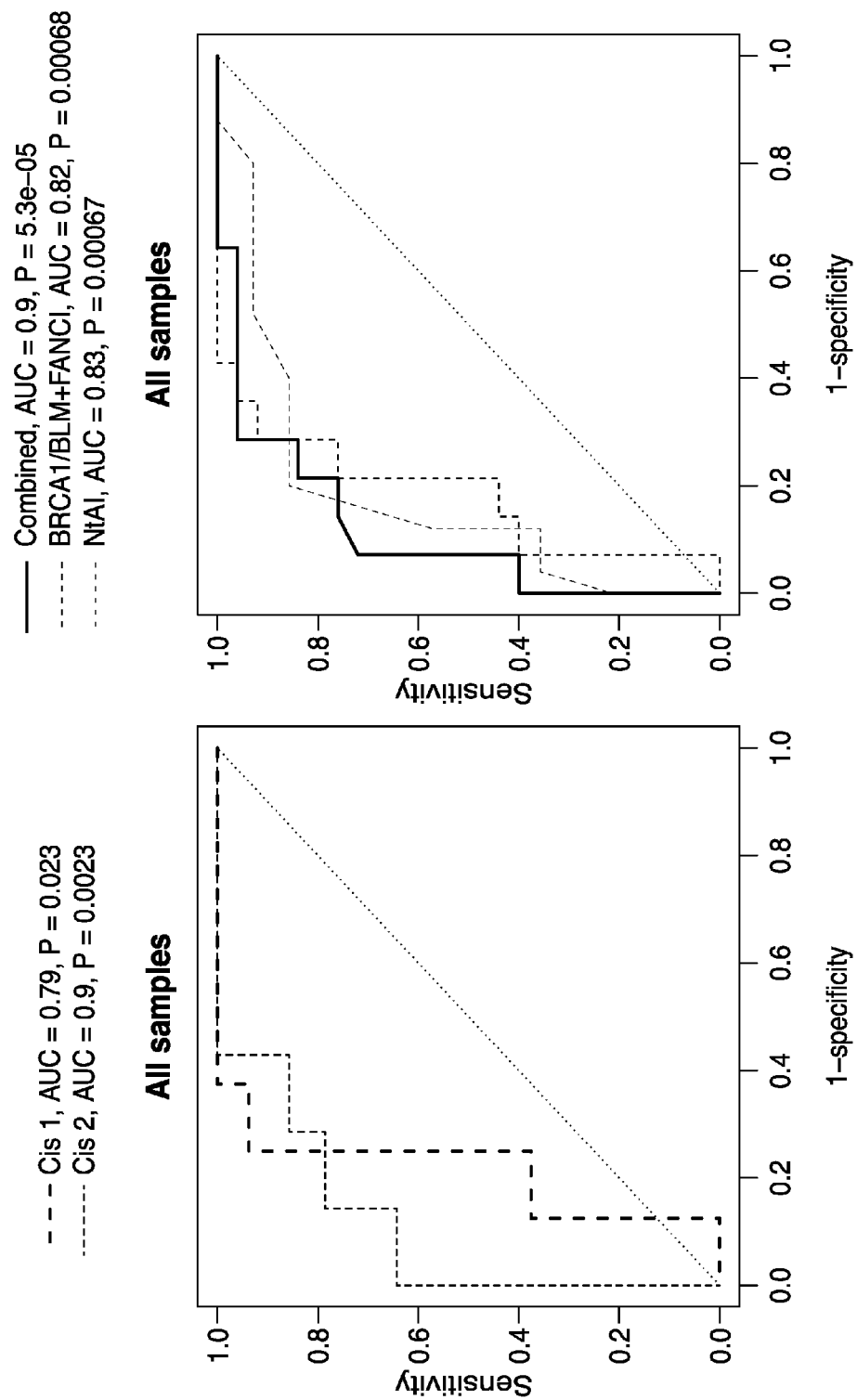
FIGS. 10A-10B show gene signatures.

We combined the mRNA results into a predictive gene signature: (BRCA1 mRNA)/(average of FANCI and BLM mRNA). ROC analysis demonstrates that this 3 gene mRNA signature is significantly associated with cisplatin response in both TN cisplatin trials (FIG. 10A). A prediction model combining NtAI and the 3 gene signature improved the prediction of cisplatin sensitivity (FIG. 10B). Based on the combined model, 25% of cases are "biomarker positive" with predictive accuracy of 0.86, a positive predictive value of 0.89, a negative predictive value of 0.85, sensitivity of 0.67, and specificity of 0.96 with a p-value of 0.00016.

EXAMPLE 7

Optimization of BRCA1-BLM-FANCI mRNA Measurement

Figure 11:
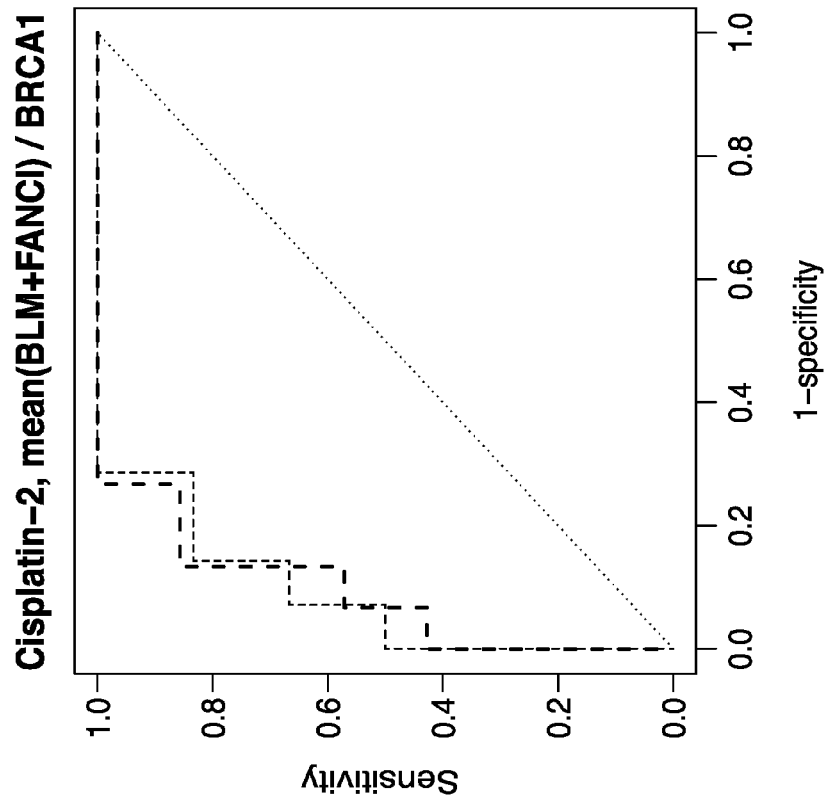
FIG. 11 depicts ROC analysis of 3 gene signature to determine cisplatin sensitivity in cisplatin 2 trial. Blue: all cases; red; BRCA normal cases only.

Several different RT-PCR primer pair assays will be designed to measure mRNA expression for each of the three genes. Data from the Cisplatin2 trial comparing the BRCA1, BLM, and FANCI mRNA levels on microarray to mRNA levels as measured by quantitative real-time PCR and found good correlation. The 3-gene predictive model of BRCA1/(avg of BLM+FANCI) using the RT-PCR measurements performed very well for prediction of cisplatin response (FIG. 11).

EXAMPLE 8

Platinum salts are effective treatment and standard therapy for a number of cancer types including serous ovarian carcinoma, high grade urothelial carcinoma, pancreatic adenocarcinoma, glioblastoma multiforme, and lung squamous cell carcinoma. Breast adenocarcinomas arising in women carrying BRCA1 or BRCA2 mutations are also sensitive to cisplatin chemotherapy (Byrski, 2008). BRCA1 is a tumor suppressor that plays important roles in several aspects of maintenance of genome integrity. Complete absence of functional BRCA1, as occurs in tumors of BRCA1 mutation carriers with loss of the wild-type allele, leads to defective error-free homologous recombination-type double strand break repair. These BRCA1−/− tumors are sensitive to inhibitors of PARP1 (ref) whereas, so far, few or no sporadic BRCA wild-type breast cancers have responded to these agents. Recent studies have shown that in addition to double strand break repair, BRCA1 also plays an important role in response to replication stress and repair of stalled or collapsed replication forks (Pathania, 2011). Preliminary evidence suggests the replication repair functions of BRCA1 may be haploinsufficient in BRCA1 heterozygous cells (Pathania, unpublished data). The platinum salts generate interstrand and intrastrand crosslinks that distort DNA and lead to stalled replication forks. If these stalled forks collapse, double strand breaks will results. It is possible that several BRCA1-dependent pathways are involved in platinum-induced DNA damage response including damage recognition and lesion excision, suppression of translesion synthesis, checkpoint activation, and repair of DS breaks after fork collapse.

The activity of cisplatin has recently been extended to estrogen, progesterone, and HER2 receptor negative sporadic breast cancers (triple-negative breast cancers, TNBC) (Silver, 2010; Birkbak, 2012; Ryan, 2009). When carboplatin was added to anthracycline and taxane chemotherapy for treatment of TNBC, the response rate was higher but resulted in notably greater toxicity. Predictors of tumor response to platinum salts are needed to determine which patients may derive the greatest benefit from the addition of platinum. Previous molecular studies have shown the platinum-sensitive TNBC and serous ovarian cancers carry high levels of genomic rearrangements and chromosomal allelic imbalance, suggesting these cancers may share similar defects in DNA repair, which may make them particularly sensitive to platinum chemotherapy (Birkbak, 2012). Many of the platinum-sensitive sporadic TNBCs have promoter methylation and reduction in the expression of BRCA1 (Birkbak, 2012; Silver, 2010). These result suggests that platinum sensitivity may be related to a functional defect that occurs when there is insufficient BRCA1 levels, raising the possibility that defects in a haploinsufficient function of BRCA1, such as replication-dependent stalled fork repair, may be indicative of sensitivity to interstrand cross-linkers such as the platinum salts.

To further explore and define other specific molecular alterations that might be associated with cisplatin sensitivity, we took and integrated genomic approach combining differential analysis of gene expression and DNA copy number in cisplatin sensitive compared to cisplatin resistant triple negative breast cancers. We identify two genes, the Bloom helicase (BLM) and Fanconi anemia complementation group I (FANCI), that have both increased DNA copy number at chr 15q26 and concordant mRNA overexpression in the TNBC with increased sensitivity to cisplatin therapy. In vitro modulation of BLM and FANCI expression suggest these two genes play a functional role and promote DNA damage and sensitivity to platinum salts, but have no effect on taxane sensitivity.

Identification of genes critical for tumor response to specific chemotherapy drugs is a challenge, but important for tailoring therapy and avoiding unnecessary toxicity in patients. Integrated genomic approaches that combine DNA copy number analysis with gene expression profile analysis has successfully indicated genomic alterations associated with chemotherapy resistance and tumor response (Li, 2010). We have previously published the results of two trials of cisplatin chemotherapy in TNBC in which presurgical treatment with cisplatin resulted in greater than 90% reduction in tumor volume in 36% and 39% of patients respectively (Silver, 2010; Ryan, 2009). Molecular inversion probe SNP copy number profiles of pretreatment tumors from both cisplatin TNBC trials were reported previously (Birkbak, 2012). Gene expression profiles from the pretreatment tumor samples from the first cisplatin TNBC trial were also reported previously (Silver, 2010). For this study, we generated gene expression profiles from the pretreatment tumor biopsies from the second cisplatin TNBC trial.

To determine genes whose expression is significantly and robustly associated with response to cisplatin, we performed a leave-one-out differential gene expression analysis in each trial, comparing the gene expression of tumors resistant to cisplatin to tumors that were sensitive to cisplatin. For each leave-one-out round, one sample was removed and all genes significantly associated with response were determined. The direction of association for each gene (higher in sensitive vs. lower in sensitive) was also noted. Permutation testing of this gene expression comparison exercise indicated that a gene must be present in 85% or more rounds to be significant. This analysis identified only 12 genes whose expression was significantly associated with platinum response, in the same direction, in at least 85% of all rounds in both cisplatin TNBC cohorts.

We performed next a similar leave one out comparison analysis of the DNA copy numbers of cisplatin sensitive vs. cisplatin resistant TNBC tumors in the two trials. Permutation testing of the DNA copy number LOO analysis indicated that a gene must be present in 50% or more LOO rounds to be significant. This analysis identified 234 genes from four different chromosomes with differential copy number associated with cisplatin response in at least 50% of all rounds in both cisplatin TNBC cohorts.

Figure 1B:
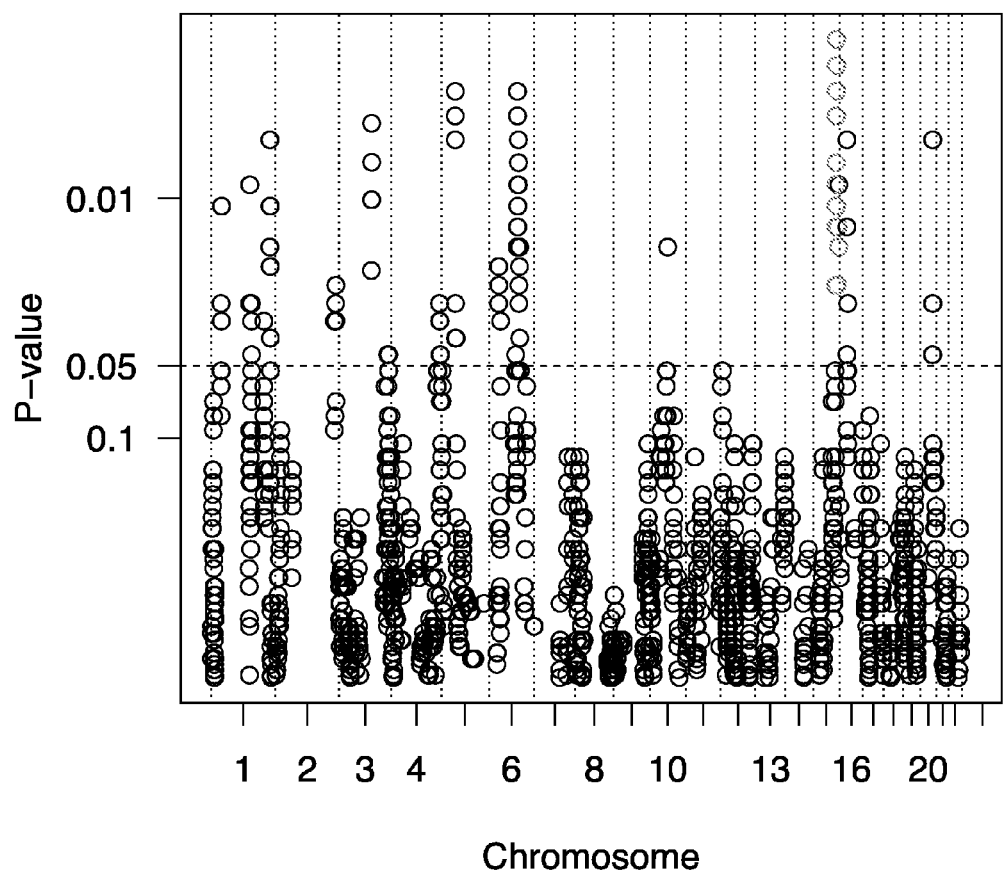

Only two genes were identified in both the DNA copy number and gene expression leave-one-out analyses for association with platinum sensitivity, Bloom helicase (BLM) and Fanconi anemia complementation group I (FANCI), both located at chromosome 15q26. The DNA copy number of the 15q26 region containing these two genes was significantly higher in the cisplatin-sensitive tumors in both TNBC cohorts ($p=0.00236$ and $p=0.0107$, respectively. Similarly, cisplatin sensitive tumors had significantly higher BLM expression in both TNBC cohorts (cisplatin-1, mean log2 expression, 8.26 versus 7.54, $p=0.00278$; cisplatin-2, mean log2 expression, 10.67 versus 9.41, $p=0.00745$; FIG. 1C-D). FANCI expression was higher in the cisplatin-sensitive TNBCs in both cohorts (cisplatin-1, mean log2 expression 7.87 versus 6.80, $p=0.00356$; cisplatin-2, mean log2 expression 10.74 versus 9.77, $p=0.0125$).

The gene expression of BLM and FANCI as measured by Affymetrix U133 array was validated by RT-PCR in the same samples and the results showed good correlation (BLM, $r=0.866$; FANCI, $r=0.733$). BLM (and FANCI) are reported to have post-translational mechanisms of protein regulation. To determine if overexpression of BLM and FANCI mRNA also results in increased expression of the protein, we measured BLM (and FANCI) protein by western blot analysis in protein extracts from a series of frozen breast tumor samples for which mRNA gene array expression levels were known (Lu, 2008). BLM normalized to actin (and FANCI) showed good correlation between mRNA expression levels and protein expression levels ($r=0.70$).

BRCA1 as measured by RT-PCR was identified in our previous studies as significantly associated with cisplatin resistance (Birkbak, 2012; Silver, 2010). In contrast to BLM and FANCI, BRCA1 expression as measured by microarray was poorly correlated with expression as measured by RT-PCR ($r=xxx$); the microarray BRCA1 probe performance was especially poor in the data from first cisplatin TNBC cohort. Therefore, we used the RT-PCR expression data to test the association of the ratio of BRCA1/average (BLM+FANCI) expression and cisplatin response. The ratio was significantly higher in the cisplatin sensitive tumors in both cohorts (cisplatin-1, median x vs y, $p=0.023$; cisplatin-2, median 7.69 vs 4.07, $p=0.0016$).

To validate these specific gene associations with platinum response, we tested a publically available gene expression data set from a serous ovarian cancer trial of either carboplatin monotherapy or paclitaxel monotherapy and sought associations with response to the therapy received. The average expression of BLM and FANCI was significantly higher in the carboplatin-sensitive ovarian cancers (median 5.46 versus 4.50, $p=0.026$). The ratio of BLM+FANCI/BRCA1 was also significantly higher in carboplatin sensitive ovarian cancers (median 1.29 vs 0.42, $p=0.026$). Interestingly, the association of BLM and FANCI with paclitaxel response was not significant and the trend was in the opposite direction (median 5.17 versus 4.79, $p=0.27$).

We also showed protein abundance of BRCA1, BLM, FANCI, and Cyclin A was measured by Western blot analysis in protein extracts from a panel of breast cancer cell lines. The bands were quantitated by densitometry and displayed in bar plots. We showed the quantitation of BLM to Actin and BRCA1 to BLM ratio. Three cell lines (BT549, HCC1143, and HCC38) are normal genotype for BRCA1 and have high BLM/Actin and low ratio of BRCA1/BLM. Two cell lines (MDA231 and MDA453) are also normal genotype for BRCA1 but have relatively higher expression of BRCA1/BLM and lower BLM/actin. HCC1937 and MDA436 have homozygous mutation in BRCA1 and undetectable BRCA1/BLM, and higher expression of BLM/Actin.

A panel of cell lines was evaluated for sensitivity to various treatments as indicated by colony formation assay and calculation of IC50 values. We showed a pattern of sensitivity to cisplatin, UV radiation treatment, and Parp inhibitor Olaparib across the panel of cell lines is associated with the pattern of relative expression of BRCA1/BLM and BLM/Actin. The two BRCA1 mutated cell lines and the three cell lines with low BRCA1/BLM and high BLM/actin have greater sensitivity to DNA strand cross-linker cisplatin, PARP inhibitor Olaparib, and UV irradiation. The two cell lines with low BLM and high BRCA1/BLM (MDA231, MDA453) are relatively resistant to these treatments. In contrast, there is no apparent association between BLM and BRCA1 expression with the pattern of sensitivity to the microtubule stabilizer Paclitaxel.

We also treated U2OS cells treated shRNA to BRCA1. After 1 week, the expression of BRCA1 and BLM were measured by Western blot analysis. Cells treated with the BRCA1 specific shRNA showed increased expression of BLM compared to control cells treated with shRNA to luciferase.

We further treated BT549 breast cancer cells, with inherent high levels of BLM and FANCI were treated with gene-specific siRNAs to BLM or FANCI or with a scramble control. Gene specific siRNA treatment resulted in reduced mRNA expression as determined by RT-PCR. Sensitivity to cisplatin and to paclitaxel was determined by colony formation assay to calculate the IC50. siRNA knockdown of either BLM or FANCI resulted in increased IC50 (greater resistance) to cisplatin treatment but no significant effect on sensitivity to paclitaxel.

MDA231 cells have low levels of BLM and relative resistance to cisplatin. These cells were used in experiments to assess the effect of increasing the expression of BLM. A lentivirus expression vector for HA-tagged BLM cDNA or a control vector was transfected into MDA231 cells. BLM expression was assessed by Western blot analysis for endogenous BLM or for the HA-tag in cells treated with control vector, BLM cDNA, BLM cDNA and a small molecule inhibitor of BLM helicase (BLMi), or BLM cDNA and BLM siRNA. We showed that siRNA for BLM reduced the expression of endogeneous and HA-tagged BLM whereas the small molecule inhibitor (BLMi) had no effect on protein expression of BLM.

IC50 for cisplatin was determined by colony formation assay in MDA231 breast cancer cells treated with control vector, BLM cDNA vector, BLM cDNA plus the BLM small molecule inhibitor, and BLM cDNA plus BLM siRNA. Overexpression of BLM resulted in decrease in the IC50 (greater sensitivity) to cisplatin. Consistent with the other findings, this effect was reversed by treatment with the BLM helicase inhibitor and by siRNA knockdown of BLM.

We also performed an immunofluorescence assay for markers of DNA damage (H2Ax-p and 53BP1-p) in MDA231 cells treated with control vector, BLM cDNA, BLM cDNA+BLM inhibitor, or BLM cDNA+BLM siRNA. Overexpression of BLM results in increased H2AX and 53BP1 foci in the absence of any cisplatin treatment indicating spontaneous DNA damage. This effect is even greater in cells treated with cisplatin after 4 hours. The quantitation of foci is shown in the lower bar graphs. The addition of a small molecule BLM helicase inhibitor (Bi) or siRNA to BLM (si) blocks the effect of BLM overexpression on DNA damage foci.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web and/or the National Center for Biotechnology Information (NCBI) on the world wide web.

EQUIVALENTS

Those skilled in the art will recognize, or be able to ascertain using no more than routine experimentation, many equivalents to the specific embodiments of the invention described herein. Such equivalents are intended to be encompassed by the following claims.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method for treating cancer having increased expression of BLM and FANCI of at least two-fold compared to BRCA1 expression in a human subject in need thereof, said method comprising the step of administering a platinum-comprising cancer chemotherapy to the human subject.

2. A method of treating cancer having cancer cells with a chromosome 15q26 copy number gain compared to the cancer cells' chromosome 15centromere copy number in a human subject in need thereof, said method comprising the step of administering a platinum-comprising cancer chemotherapy to the human subject.

3. The method of claim 2, wherein the cancer is selected from breast cancer, ovarian cancer and lung cancer.

4. The method of claim 2, wherein the subject's cancer is known to not express a detectable quantity of ER, PgR, and HER2 receptor.

* * * * *